(12) United States Patent
Funkner et al.

(10) Patent No.: US 11,760,992 B2
(45) Date of Patent: *Sep. 19, 2023

(54) METHOD FOR PRODUCING AND PURIFYING RNA, COMPRISING AT LEAST ONE STEP OF TANGENTIAL FLOW FILTRATION

(71) Applicant: CureVac Manufacturing GmbH, Tübingen (DE)

(72) Inventors: Andreas Funkner, Tübingen (DE); Stefanie Dorner, Tübingen (DE); Stefanie Sewing, Tübingen (DE); Johannes Kamm, Tübingen (DE); Norbert Broghammer, Tübingen (DE); Thomas Ketterer, Gomaringen (DE); Thorsten Mutzke, Reutlingen (DE)

(73) Assignee: CureVac Manufacturing GmbH, Tübingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/820,242

(22) Filed: Aug. 16, 2022

(65) Prior Publication Data

US 2023/0151352 A1    May 18, 2023

Related U.S. Application Data

(63) Continuation of application No. 17/591,978, filed on Feb. 3, 2022, which is a continuation of application No. 16/934,279, filed on Jul. 21, 2020, now Pat. No. 11,274,293, which is a continuation of application No. 15/580,092, filed as application No. PCT/EP2016/062152 on May 30, 2016, now Pat. No. 10,760,070.

(30) Foreign Application Priority Data

May 29, 2015 (WO) ................. PCT/EP2015/062002

(51) Int. Cl.
| | | |
|---|---|---|
| *C12N 15/10* | (2006.01) | |
| *C12P 19/34* | (2006.01) | |
| *B01D 61/14* | (2006.01) | |
| *B01D 71/12* | (2006.01) | |
| *G01N 30/02* | (2006.01) | |

(52) U.S. Cl.
CPC ....... *C12N 15/1017* (2013.01); *B01D 61/145* (2013.01); *B01D 71/12* (2013.01); *C12P 19/34* (2013.01); *G01N 30/02* (2013.01); *G01N 2030/027* (2013.01)

(58) Field of Classification Search
CPC ... B01D 61/145; B01D 71/12; C12N 15/1017
See application file for complete search history.

(56) References Cited

U.S. PATENT DOCUMENTS

| | | | |
|---|---|---|---|
| 4,839,295 | A | 6/1989 | Smith |
| 5,057,426 | A | 10/1991 | Henco et al. |
| 5,298,392 | A | 3/1994 | Atlas et al. |
| 5,447,922 | A | 9/1995 | Lawrence et al. |
| 5,700,667 | A | 12/1997 | Marble et al. |
| 5,786,464 | A | 7/1998 | Seed |
| 6,011,148 | A | 1/2000 | Bussey et al. |
| 6,114,148 | A | 9/2000 | Seed |
| 6,586,218 | B2 | 7/2003 | Milburn et al. |
| 6,773,885 | B1 | 8/2004 | Walder et al. |
| 6,794,140 | B1 | 9/2004 | Goldsborough |
| 6,989,442 | B2 | 1/2006 | Vargeese |
| 7,767,399 | B2 | 8/2010 | Murphy et al. |
| 7,807,822 | B2 | 10/2010 | Bridenbaugh et al. |
| 8,075,780 | B2 | 12/2011 | Pearce |
| 8,217,016 | B2 | 7/2012 | Hoerr et al. |
| 8,383,340 | B2 | 2/2013 | Ketterer et al. |
| 8,703,906 | B2 | 4/2014 | Baumhof |
| 8,859,229 | B2 | 10/2014 | Rabinovich et al. |
| 8,859,275 | B2 | 10/2014 | Notka et al. |
| 8,968,746 | B2 | 3/2015 | Baumhof et al. |
| 9,155,788 | B2 | 10/2015 | Hoerr et al. |
| 9,226,959 | B2 | 1/2016 | Kramps et al. |
| 9,234,013 | B2 | 1/2016 | Thess et al. |
| 9,314,535 | B2 | 4/2016 | Baumhof |
| 9,352,028 | B2 | 5/2016 | Barner et al. |
| 9,402,887 | B2 | 8/2016 | Probst et al. |
| 9,421,255 | B2 | 8/2016 | Baumhof et al. |
| 9,433,669 | B2 | 9/2016 | Hoerr et al. |
| 9,433,670 | B2 | 9/2016 | Hoerr et al. |

(Continued)

FOREIGN PATENT DOCUMENTS

| | | |
|---|---|---|
| CA | 2468048 | 8/1995 |
| CA | 2 277 165 | 7/1998 |

(Continued)

OTHER PUBLICATIONS

Eckmann et al., "Control of poly(A) tail length," WIREs RNA, 2:348-361, 2011.
Office Communication issued in U.S. Appl. No. 17/591,978, dated Jan. 25, 2023.
Peng et al., "In vivo and in vitro analysis of poly(A) length effects on mRNA translation," Meth. Mol. Biol., 419:215-230, 2008.
Poly(A) Tail-Length Assay Kit, Affymetrix, pp. 1-23 (2010).
Anderson et al., "HPLC purification of RNA for crystallography and NMR", RNA, 2(2): 110-117, 1996.
Azarani and Hecker, "RNA chromatography under thermally denaturing conditions: analysis and quality determination of RNA," Transgenomic, Application Note 116, 2000.

(Continued)

*Primary Examiner* — Pancham Bakshi
(74) *Attorney, Agent, or Firm* — Parker Highlander PLLC

(57) ABSTRACT

The present invention relates to method for producing and purifying RNA comprising the steps of providing DNA encoding the RNA; transcription of the DNA into RNA; and conditioning and/or purifying of the solution comprising transcribed RNA by one or more steps of tangential flow filtration (TFF).

30 Claims, 17 Drawing Sheets

(56) References Cited

U.S. PATENT DOCUMENTS

| | | |
|---|---|---|
| 9,439,956 B2 | 9/2016 | Hoerr et al. |
| 9,447,431 B2 | 9/2016 | Thess et al. |
| 9,463,228 B2 | 10/2016 | Hoerr et al. |
| 9,572,874 B2 | 2/2017 | Fotin-Mleczek et al. |
| 9,616,084 B2 | 4/2017 | Mutzke |
| 9,623,095 B2 | 4/2017 | Kallen et al. |
| 9,655,955 B2 | 5/2017 | Hoerr et al. |
| 9,669,089 B2 | 6/2017 | Thess et al. |
| 9,683,233 B2 | 6/2017 | Thess |
| 9,688,729 B2 | 6/2017 | Kramps et al. |
| 9,737,595 B2 | 8/2017 | Lorenz et al. |
| 9,839,697 B2 | 12/2017 | Thess et al. |
| 9,890,391 B2 | 2/2018 | Thess et al. |
| 9,907,862 B2 | 3/2018 | Baumhof |
| 9,957,499 B2 | 5/2018 | Heartlein |
| 9,974,845 B2 | 5/2018 | Fotin-Mleczek et al. |
| 10,010,592 B2 | 7/2018 | Thess et al. |
| 10,017,826 B2 | 7/2018 | von der Mülbe et al. |
| 10,047,375 B2 | 8/2018 | Thess |
| 10,080,809 B2 | 9/2018 | Thess |
| 10,111,967 B2 | 10/2018 | Fotin-Mleczek et al. |
| 10,111,968 B2 | 10/2018 | Thess et al. |
| 10,117,920 B2 | 11/2018 | Fotin-Mleczek et al. |
| 10,138,507 B2 | 11/2018 | Bancel et al. |
| 10,150,797 B2 | 12/2018 | Kramps et al. |
| 10,166,283 B2 | 1/2019 | Thess et al. |
| 10,172,935 B2 | 1/2019 | Kallen et al. |
| 10,188,748 B2 | 1/2019 | von der Mülbe et al. |
| 10,232,024 B2 | 3/2019 | Thess et al. |
| 10,293,058 B2 | 5/2019 | Fotin-Mleczek et al. |
| 10,293,060 B2 | 5/2019 | Baumhof |
| 10,307,472 B2 | 6/2019 | Fotin-Mleczek et al. |
| 10,369,216 B2 | 8/2019 | Fotin-Mleczek |
| 10,434,154 B2 | 10/2019 | Probst et al. |
| 10,434,158 B2 | 10/2019 | Fotin-Mleczek et al. |
| 10,441,653 B2 | 10/2019 | Hoerr et al. |
| 10,501,768 B2 | 12/2019 | Eber et al. |
| 10,517,827 B2 | 12/2019 | Eber et al. |
| 10,568,958 B2 | 2/2020 | Baumhof et al. |
| 10,568,972 B2 | 2/2020 | von der Mülbe et al. |
| 10,588,959 B2 | 3/2020 | Kallen et al. |
| 10,596,252 B2 | 3/2020 | Kallen et al. |
| 10,610,605 B2 | 4/2020 | Thess et al. |
| 10,648,017 B2 | 5/2020 | Wochner |
| 10,653,768 B2 | 5/2020 | Mutzke et al. |
| 10,653,799 B2 | 5/2020 | Thess et al. |
| 10,682,406 B2 | 6/2020 | Thess et al. |
| 10,682,426 B2 | 6/2020 | Schnee et al. |
| 10,711,315 B2 | 7/2020 | von der Mülbe et al. |
| 10,729,654 B2 | 8/2020 | Eber et al. |
| 10,729,761 B2 | 8/2020 | Kallen et al. |
| 10,738,306 B2 | 8/2020 | Thess |
| 10,751,424 B2 | 8/2020 | Baumhof |
| 10,760,070 B2 * | 9/2020 | Funkner ............... B01D 71/12 |
| 10,780,054 B2 | 9/2020 | Ketterer et al. |
| 10,799,577 B2 | 10/2020 | Thess et al. |
| 10,799,602 B2 | 10/2020 | Baumhof |
| 10,837,039 B2 | 11/2020 | Wochner et al. |
| 10,869,935 B2 | 12/2020 | Fotin-Mleczek et al. |
| 10,898,584 B2 | 1/2021 | Schlake |
| 10,898,589 B2 | 1/2021 | Thess et al. |
| 10,912,826 B2 | 2/2021 | Thess et al. |
| 10,918,740 B2 | 2/2021 | Fotin-Mleczek et al. |
| 10,988,754 B2 | 4/2021 | Fotin-Mleczek et al. |
| 11,034,729 B2 | 6/2021 | Kramps et al. |
| 11,078,247 B2 | 8/2021 | Fotin-Mleczek |
| 11,110,156 B2 | 9/2021 | Thess et al. |
| 11,110,157 B2 | 9/2021 | Fotin-Mleczek et al. |
| 11,110,166 B2 | 9/2021 | Fotin-Mleczek |
| 11,135,312 B2 | 10/2021 | von der Mülbe et al. |
| 11,141,474 B2 | 10/2021 | Rauch et al. |
| 11,141,476 B2 | 10/2021 | Rauch |
| 11,149,278 B2 | 10/2021 | Thess et al. |
| 11,155,572 B2 | 10/2021 | Scorza et al. |
| 11,179,337 B2 | 11/2021 | Eber et al. |
| 11,225,682 B2 | 1/2022 | Reichert et al. |
| 11,241,493 B2 | 2/2022 | Rauch et al. |
| 11,248,223 B2 | 2/2022 | Yazdan Panah et al. |
| 11,254,951 B2 | 2/2022 | Thess |
| 11,266,735 B2 | 3/2022 | Kallen et al. |
| 11,268,157 B2 | 3/2022 | von der Mülbe et al. |
| 11,274,293 B2 * | 3/2022 | Funkner ............... G01N 30/02 |
| 11,279,923 B2 | 3/2022 | Funkner et al. |
| 11,286,492 B2 | 3/2022 | Thess et al. |
| 11,345,920 B2 | 5/2022 | Thess et al. |
| 2002/0096474 A1 | 7/2002 | Colman |
| 2002/0102563 A1 | 8/2002 | Gjerde et al. |
| 2005/0011836 A1 | 1/2005 | Bidlingmeyery et al. |
| 2005/0032730 A1 | 2/2005 | von der Mülbe et al. |
| 2005/0059624 A1 | 3/2005 | Hoerr et al. |
| 2005/0215777 A1 | 9/2005 | Vargeese et al. |
| 2005/0250723 A1 | 11/2005 | Hoerr et al. |
| 2006/0188490 A1 | 8/2006 | Hoerr et al. |
| 2007/0280929 A1 | 12/2007 | Hoerr et al. |
| 2008/0025944 A1 | 1/2008 | Hoerr et al. |
| 2008/0033158 A1 | 2/2008 | Ngo et al. |
| 2008/0171711 A1 | 7/2008 | Hoerr et al. |
| 2008/0260706 A1 | 10/2008 | Rabinovish et al. |
| 2008/0267873 A1 | 10/2008 | Hoerr et al. |
| 2009/0324584 A1 | 12/2009 | Hoerr et al. |
| 2010/0047261 A1 | 2/2010 | Hoerr et al. |
| 2010/0048883 A1 | 2/2010 | Ketterer et al. |
| 2010/0189729 A1 | 7/2010 | Hoerr et al. |
| 2010/0203076 A1 | 8/2010 | Fotin-Mleczek et al. |
| 2010/0291156 A1 | 11/2010 | Barner et al. |
| 2010/0305196 A1 | 12/2010 | Probst et al. |
| 2011/0053829 A1 | 3/2011 | Baumhof et al. |
| 2011/0104693 A1 | 5/2011 | Seligmann |
| 2011/0111975 A1 | 5/2011 | Schneider et al. |
| 2011/0250225 A1 | 10/2011 | Fotin-Mleczek et al. |
| 2012/0021043 A1 | 1/2012 | Kramps et al. |
| 2012/0219573 A1 | 8/2012 | Baumhof et al. |
| 2012/0258046 A1 | 10/2012 | Mutzke |
| 2013/0121988 A1 | 5/2013 | Hoerr et al. |
| 2013/0129754 A1 | 5/2013 | Thess et al. |
| 2013/0142818 A1 | 6/2013 | Baumhof et al. |
| 2013/0195867 A1 | 8/2013 | Hoerr et al. |
| 2013/0202645 A1 | 8/2013 | Barner et al. |
| 2013/0251742 A1 | 9/2013 | Probst et al. |
| 2013/0259879 A1 | 10/2013 | Baumhof et al. |
| 2013/0280283 A1 | 10/2013 | Lorenz et al. |
| 2013/0295043 A1 | 11/2013 | Kallen et al. |
| 2013/0336998 A1 | 12/2013 | Kallen et al. |
| 2014/0037660 A1 | 2/2014 | Fotin-Mleczek et al. |
| 2014/0294877 A1 | 10/2014 | Baumhof et al. |
| 2015/0030633 A1 | 1/2015 | Hoerr et al. |
| 2015/0037326 A1 | 2/2015 | Butler-Ransohoff et al. |
| 2015/0050302 A1 | 2/2015 | Thess |
| 2015/0057340 A1 | 2/2015 | Thess et al. |
| 2015/0064725 A1 | 3/2015 | Schrum et al. |
| 2015/0093413 A1 | 4/2015 | Thess et al. |
| 2015/0118183 A1 | 4/2015 | Baumhof |
| 2015/0118264 A1 | 4/2015 | Baumhof et al. |
| 2015/0141498 A1 | 5/2015 | Mutzke |
| 2015/0157565 A1 | 6/2015 | Heartlein |
| 2015/0165006 A1 | 6/2015 | Thess et al. |
| 2015/0184195 A1 | 7/2015 | Thess |
| 2015/0218554 A1 | 8/2015 | Thess |
| 2015/0258214 A1 | 9/2015 | Baumhof et al. |
| 2015/0306249 A1 | 10/2015 | Baumhof et al. |
| 2015/0320847 A1 | 11/2015 | Thess et al. |
| 2015/0366997 A1 | 12/2015 | Guild et al. |
| 2016/0001731 A1 | 1/2016 | Spivak et al. |
| 2016/0017313 A1 | 1/2016 | Spivak et al. |
| 2016/0024139 A1 | 1/2016 | Berlanda Scorza et al. |
| 2016/0024492 A1 | 1/2016 | Issa et al. |
| 2016/0024547 A1 | 1/2016 | Bancel et al. |
| 2016/0031981 A1 | 2/2016 | Heartlein et al. |
| 2016/0032273 A1 | 2/2016 | Shahrokh et al. |
| 2016/0040154 A1 * | 2/2016 | Heartlein ............... C12N 15/10 |
| | | 536/25.4 |
| 2016/0130345 A1 | 5/2016 | Fotin-Mleczek et al. |
| 2016/0151474 A1 | 6/2016 | Kallen et al. |
| 2016/0166668 A1 | 6/2016 | Kallen et al. |

(56) References Cited

U.S. PATENT DOCUMENTS

| | | |
|---|---|---|
| 2016/0166678 A1 | 6/2016 | Kallen et al. |
| 2016/0166710 A1 | 6/2016 | Baumhof |
| 2016/0166711 A1 | 6/2016 | Schnee et al. |
| 2016/0168207 A1 | 6/2016 | Kramps et al. |
| 2016/0168227 A1 | 6/2016 | Kallen et al. |
| 2016/0206719 A1 | 7/2016 | Fotin-Mleczek et al. |
| 2016/0235864 A1 | 8/2016 | Schlake et al. |
| 2016/0304883 A1 | 10/2016 | Grund et al. |
| 2016/0304938 A1 | 10/2016 | Wochner |
| 2016/0326575 A1 | 11/2016 | Von der Mulbe et al. |
| 2016/0331844 A1 | 11/2016 | Fotin-Mleczek et al. |
| 2017/0014496 A1 | 1/2017 | Fotin-Mleczek et al. |
| 2017/0029847 A1 | 2/2017 | Thess |
| 2017/0114378 A1 | 4/2017 | Wochner et al. |
| 2017/0182150 A1 | 6/2017 | Kallen et al. |
| 2017/0239372 A1 | 8/2017 | Baumhof et al. |
| 2017/0252430 A1 | 9/2017 | Fotin-Mleczek et al. |
| 2017/0326225 A1 | 11/2017 | Rauch et al. |
| 2018/0044687 A1 | 2/2018 | Thess et al. |
| 2018/0078629 A1 | 3/2018 | Lorenz et al. |
| 2018/0125952 A1 | 5/2018 | Fotin-Mleczek |
| 2018/0126003 A1 | 5/2018 | Hoerr |
| 2018/0126005 A1 | 5/2018 | Fotin-Mleczek et al. |
| 2018/0142275 A1 | 5/2018 | Roos et al. |
| 2018/0148727 A1 | 5/2018 | Grund |
| 2018/0207295 A1 | 7/2018 | Fotin-Mleczek et al. |
| 2018/0208957 A1 | 7/2018 | Roos et al. |
| 2018/0237786 A1 | 8/2018 | Schlake |
| 2018/0237817 A1 | 8/2018 | Roos et al. |
| 2018/0256694 A1 | 9/2018 | Barner et al. |
| 2018/0296663 A1 | 10/2018 | Hipp et al. |
| 2018/0312545 A1 | 11/2018 | Baumhof et al. |
| 2018/0371392 A1 | 12/2018 | Mayer |
| 2019/0008954 A1 | 1/2019 | Baumhof |
| 2019/0017100 A1 | 1/2019 | Wochner |
| 2019/0024096 A1 | 1/2019 | Schmid et al. |
| 2019/0049414 A1 | 2/2019 | Wochner et al. |
| 2019/0083602 A1 | 3/2019 | Roos et al. |
| 2019/0100784 A1 | 4/2019 | Eber et al. |
| 2019/0151438 A1 | 5/2019 | Kallen et al. |
| 2019/0160164 A1 | 5/2019 | Rauch |
| 2019/0177714 A1 | 6/2019 | Kunze et al. |
| 2019/0185859 A1 | 6/2019 | Fotin-Mleczek et al. |
| 2019/0194760 A1 | 6/2019 | Koch et al. |
| 2019/0225971 A1 | 7/2019 | Williams |
| 2019/0255161 A1 | 8/2019 | Thess et al. |
| 2019/0336608 A1 | 11/2019 | Baumhof |
| 2019/0336611 A1 | 11/2019 | Baumhof |
| 2019/0343933 A1 | 11/2019 | Horscroft et al. |
| 2019/0343942 A1 | 11/2019 | Fotin-Mleczek |
| 2019/0345504 A1 | 11/2019 | Grund |
| 2019/0351044 A1 | 11/2019 | Jasny |
| 2019/0351047 A1 | 11/2019 | Jasny |
| 2019/0381155 A1 | 12/2019 | Fotin-Mleczek et al. |
| 2019/0381180 A1 | 12/2019 | Baumhof |
| 2020/0016264 A1 | 1/2020 | Hoerr et al. |
| 2020/0023076 A1 | 1/2020 | Fotin-Mleczek |
| 2020/0040370 A1 | 2/2020 | Eber et al. |
| 2020/0085852 A1 | 3/2020 | Fotin-Mleczek |
| 2020/0085942 A1 | 3/2020 | Kramps et al. |
| 2020/0085943 A1 | 3/2020 | Baumhof et al. |
| 2020/0085944 A1 | 3/2020 | Heidenreich et al. |
| 2020/0149026 A1 | 5/2020 | Horscroft et al. |
| 2020/0163878 A1 | 5/2020 | Baumhof et al. |
| 2020/0179526 A1 | 6/2020 | Baumhof |
| 2020/0216878 A1 | 7/2020 | Wochner |
| 2020/0246451 A1 | 8/2020 | Mutzke et al. |
| 2020/0268908 A1 | 8/2020 | Schnee et al. |
| 2020/0276336 A1 | 9/2020 | Thess et al. |
| 2020/0316189 A1 | 10/2020 | Kallen et al. |
| 2020/0332293 A1 | 10/2020 | Thess |
| 2020/0338215 A1 | 10/2020 | Baumhof et al. |
| 2020/0383919 A1 | 12/2020 | Eber et al. |
| 2020/0383922 A1 | 12/2020 | Ketterer et al. |
| 2020/0392572 A1 | 12/2020 | Yazdan Panah et al. |
| 2020/0399322 A1 | 12/2020 | Baumhof et al. |
| 2021/0023199 A1 | 1/2021 | Kallen et al. |
| 2021/0030683 A1 | 2/2021 | Eber et al. |
| 2021/0030864 A1 | 2/2021 | Petsch et al. |
| 2021/0030866 A1 | 2/2021 | Kallen et al. |
| 2021/0040526 A1 | 2/2021 | Wochner et al. |
| 2021/0046179 A1 | 2/2021 | Fotin-Mleczek et al. |
| 2021/0060175 A1 | 3/2021 | Fotin-Mleczek et al. |
| 2021/0060181 A1 | 3/2021 | Thess et al. |
| 2021/0069315 A1 | 3/2021 | Baumhof et al. |
| 2021/0128716 A1 | 5/2021 | Thess et al. |
| 2021/0162037 A1 | 6/2021 | Jasny et al. |
| 2021/0170017 A1 | 6/2021 | Lutz et al. |
| 2021/0180106 A1 | 6/2021 | Wochner et al. |
| 2021/0187124 A1 | 6/2021 | Schlake |
| 2021/0198649 A1 | 7/2021 | Fotin-Mleczek et al. |
| 2021/0205434 A1 | 7/2021 | Petsch et al. |
| 2021/0251898 A1 | 8/2021 | Baumhof et al. |
| 2021/0260178 A1 | 8/2021 | Jasny et al. |
| 2021/0261627 A1 | 8/2021 | Kramps et al. |
| 2021/0261897 A1 | 8/2021 | Yazdan Panah et al. |
| 2021/0308238 A1 | 10/2021 | Hoerr et al. |
| 2021/0361761 A1 | 11/2021 | Lutz et al. |
| 2021/0361764 A1 | 11/2021 | Fotin-Mleczek |
| 2021/0369827 A1 | 12/2021 | Fotin-Mleczek et al. |
| 2021/0393755 A1 | 12/2021 | Thess et al. |
| 2021/0401966 A1 | 12/2021 | Rauch et al. |
| 2021/0401971 A1 | 12/2021 | Rauch |
| 2021/0403925 A1 | 12/2021 | Chevessier-Tünnesen et al. |
| 2022/0025369 A1 | 1/2022 | Fotin-Mleczek |
| 2022/0040281 A1 | 2/2022 | Schwendt et al. |
| 2022/0073962 A1 | 3/2022 | Schwenger et al. |
| 2022/0090092 A1 | 3/2022 | Thess et al. |
| 2022/0096616 A1 | 3/2022 | Barner et al. |
| 2022/0119795 A1 | 4/2022 | Yazdan Panah et al. |
| 2022/0133908 A1 | 5/2022 | Rejman et al. |
| 2022/0136011 A1 | 5/2022 | Thess |
| 2022/0144877 A1 | 5/2022 | Heinz et al. |
| 2022/0152193 A1 | 5/2022 | Kallen et al. |
| 2022/0154253 A1 | 5/2022 | von der Mülbe |
| 2022/0160638 A1 | 5/2022 | Ketterer et al. |
| 2022/0168225 A1 | 6/2022 | Eber et al. |
| 2022/0193226 A1 | 6/2022 | Rauch et al. |
| 2022/0211838 A1 | 7/2022 | Oostvogels et al. |
| 2022/0211841 A1 | 7/2022 | Oostvogels et al. |
| 2022/0218815 A1 | 7/2022 | Rauch et al. |

FOREIGN PATENT DOCUMENTS

| | | |
|---|---|---|
| DE | 102006061015 | 6/2008 |
| EP | 1 245 674 B9 | 10/2009 |
| EP | 3 521 429 | 8/2019 |
| JP | 8073477 | 3/1996 |
| WO | WO 1995/008626 | 3/1995 |
| WO | WO 2001/007599 | 2/2001 |
| WO | WO 2001/46687 | 6/2001 |
| WO | WO 2002/085434 | 10/2002 |
| WO | WO 2003/059381 | 7/2003 |
| WO | WO 2004/022574 | 3/2004 |
| WO | WO 2005/058933 | 6/2005 |
| WO | WO 2006/004648 | 1/2006 |
| WO | WO 2008/097926 | 8/2008 |
| WO | WO 2009/127230 | 10/2009 |
| WO | WO 2010/088927 | 8/2010 |
| WO | WO 2011/069528 | 6/2011 |
| WO | WO 2011/069587 | 6/2011 |
| WO | WO 2011/144358 | 11/2011 |
| WO | WO 2012/077080 | 6/2012 |
| WO | WO 2013/113501 | 8/2013 |
| WO | WO 2013/113502 | 8/2013 |
| WO | WO 2013/113736 | 8/2013 |
| WO | WO 2013/120626 | 8/2013 |
| WO | WO 2013/120627 | 8/2013 |
| WO | WO 2013/120628 | 8/2013 |
| WO | WO 2013/120629 | 8/2013 |
| WO | WO 2013/143698 | 10/2013 |
| WO | WO 2013/143699 | 10/2013 |
| WO | WO 2013/143700 | 10/2013 |
| WO | WO 2013/174409 | 11/2013 |

(56) References Cited

FOREIGN PATENT DOCUMENTS

| WO | WO 2014/127917 | 8/2014 |
|---|---|---|
| WO | WO 2014/140211 | 9/2014 |
| WO | WO 2014/144039 | 9/2014 |
| WO | WO 2014/144711 | 9/2014 |
| WO | WO 2014/144767 | 9/2014 |
| WO | WO 2014/152027 | 9/2014 |
| WO | WO 2014/152030 | 9/2014 |
| WO | WO 2014/152031 | 9/2014 |
| WO | WO 2014/152966 | 9/2014 |
| WO | WO 2014/160243 | 10/2014 |
| WO | WO 2015/024664 | 2/2015 |
| WO | WO 2015/024665 | 2/2015 |
| WO | WO 2015/024666 | 2/2015 |
| WO | WO 2015/024667 | 2/2015 |
| WO | WO 2015/024668 | 2/2015 |
| WO | WO 2015/024669 | 2/2015 |
| WO | WO 2015/052133 | 4/2015 |
| WO | WO 2015/062738 | 5/2015 |
| WO | WO 2015/101414 | 7/2015 |
| WO | WO 2015/101415 | 7/2015 |
| WO | WO 2015/101416 | 7/2015 |
| WO | WO 2015/135558 | 9/2015 |
| WO | WO 2015/149944 | 10/2015 |
| WO | WO 2015/164773 | 10/2015 |
| WO | WO 2015/188933 | 12/2015 |
| WO | WO 2016/107877 | 7/2016 |
| WO | WO 2016/165825 | 10/2016 |
| WO | WO 2016/165831 | 10/2016 |
| WO | WO 2016/174227 | 11/2016 |
| WO | WO 2016/174271 | 11/2016 |
| WO | WO 2016/184575 | 11/2016 |
| WO | WO 2016/184576 | 11/2016 |
| WO | WO 2016/184822 | 11/2016 |
| WO | WO 2016/193226 | 12/2016 |
| WO | WO 2016/203025 | 12/2016 |
| WO | WO 2017/001058 | 1/2017 |
| WO | WO 2017/009376 | 1/2017 |
| WO | WO 2017/021546 | 2/2017 |
| WO | WO 2017/025120 | 2/2017 |
| WO | WO 2017/025447 | 2/2017 |
| WO | WO 2017/036580 | 3/2017 |

OTHER PUBLICATIONS

Bryant and Manning, "Isolation of mRNA by affinity chromatography," The Nucleic Acid Protocols Handbook, 2: 9-11, 2000.
Chaudhari et al., "A review on good manufacturing practice (GMP) for medicinal products", PharmaTutor, 2(9): 8-19, 2014.
Chern et al., "Comparison of quantitative PCR assays for *Escherichia coli* targeting ribosomal RNA and single copy genes", Lett. Appl. Microbiol., 52:298-306, 2011.
Crain, "Preparation and enzymatic hydrolysis of DNA and RNA for mass spectrometry," Nucleic Acid Constituents, 193:782-790, 1990.
Dickman et al., "Enrichment and analysis of RNA centered on Ion Pair Reverse Phase Methodology", RNA, 12(4): 691-696, 2006.
Edelmann et al., "Production of pure and functional RNA for in vitro reconstitution experiments", Methods, 65:333-341, 2014.
Fernandez et al., "Cross flow filtration of RNA extracts by hollow fiber membrane," Acta Biotechnol., 12:49-56, 1992.
Georgopoulos et al., "Use of high-performance liquid chromatographic fractionation of large RNA molecules in the assay of group 1 intron ribozyme activity", J Chromatogr A., 868(1): 109-114, 2000.
Guerrero-German et al., "Purification of plasmid DNA using tangential flow filtration and tandem anion-exchange membrane chromatography," Bioprocess Biosyst. Eng., 32:615-623, 2009.
Hashimoto, "Macroporous synthetic hydrophilic resin-based packings for the separation of biopolymers", J Chromatogr., 544: 249-244, 1991.
Kahn et al., "Purification of plasmid DNA by tangential flow filtration," Biotechnol. Bioeng., 69:101-106, 2000.

Kallen et al., "A development that may evolve into a revolution in medicine: mRNA as the basis for novel, nucleotide-based vaccines and drugs", Ther Adv Vaccines, 2(1): 10-31, 2014.
Kendall et al., "Purification of plasmid DNA by an integrated operation comprising tangential flow filtration and nitrocellulose adsorption," Biotechnol. Bioeng., 79:816-822, 2002.
Kern et al., "Application of solution equilibrium analysis to in vitro RNA transcription", Biotechnology Progress, 13(6): 747-756, 1997.
Kowalak et al., "A novel method for the determination of posttranscriptional modification in RNA by mass spectrometry," Nucleic Acids Research, 21(19):4577-4585, 1993.
Lajmi et al., "Membrane purification of an antisense oligonucleotide," Org. Process Res. Dev., 8(4):651-657, 2004.
Liu and Price, "in vitro transcription on DNA templates immobilitzed to streptavidin magnesphere® paramagnetic particles," Promega Notes, 64:21, 1997.
Martins et al., "Ribonucleic acid purification," J. Chromatogr. A, 1355:1-14, 2014.
McFarland et al., "Separation of oligo-RNA by reverse-phase HPLC", Nucleic Acids Res., 7(4): 1067-1080, 1979.
Meng and Limbach, "Mass spectrometry of RNA: linking the genome to the proteome," Brief Funct Genomic Proteomic, 5(1):87-95, 2006.
Mitra, "Using analytical ultracentrifugation (AUC) to measure global conformational changes accompanying equilibrium tertiary folding of RNA molecules," Methods in Enzymology, 469:209-236, 2009.
Nunes et al., "Plasmid DNA recovery from fermentation broths by a combined process of micro-and ultrafiltration: Modeling and application," Journal of Membrane Science, 415-416, 24-35, 2012.
Parkhomchuk et al., "Transcriptome analysis by strand-specific sequencing of complementary DNA," Nucleic Acids Research, 37(18):e123, 2009.
Pascolo, "Messenger RNA-based vaccines," Expert Opin. Biol. Ther., 4(8):1285-1294, 2004.
Pascolo, "RNA-based therapies," Drug Discovery Handbook, Chapter 27, pp. 1259-1308, 2005.
Pascolo, "Vaccination with messenger RNA (mRNA)", Toll-Like Receptors (TLRs) and Innate Immunity, Handbook of Experimental Pharmacology 183, Bauer and Hartmann ed., Springer-Verlag, 2008.
Pascolo, "Vaccination with messenger RNA", Methods in Molecular Medicine, vol. 127: DNA Vaccines: Methods and Protocols, 2nd Ed., Saltzman et al. ed., Humana Press, pp. 23-40, 2006.
Petro et al., "Molded continuous poly(styrene-co-divinylbenzene) rod as a separation medium for the very separation ofpolymers. Comparison of the chromatographic properties of the monolithic rod with columns packed with porous and non-porous beads in high-performance liquid chromatography of polystyrenes", J Chromatogr A., 752(1-2): 59-66, 1996. (abstract only).
Pomerantz and McCloskey, "Analysis of RNA hydrolyzates by liquid chromatography-mass spectrometry," Methods in Enzymology, 193:796-824, 1990.
Sahin et al., "mRNA-based therapeutics—developing a new class of drugs", Nature Reviews Drug Discovery, 13(10): 759-780, 2014.
Schlake et al., "Developing mRNA-vaccine technologies", RNA Biology, 9(11): 1319-1330, 2012.
Smith et al., "Fast and Accurate Method for Quantitating *E coli* Host-Cell DNA Contamination in Plasmid DNA Preparations", Biotechniques, 26:518-526, 1999.
Sobczak and Krzyzosiak, "RNA structure analysis assisted by capillary electrophoresis," Nucleic Acids Research, 30(22):e124, 2002.
Stadler et al., "Plasmid DNA purification", J. Gene Med., 6:S54-S66, 2004.
Sun et al., "Large-scale purification of pharmaceutical-grade plasmid DNA using tangential flow filtration and multi-step chromatography," J. Biosci. Bioeng., 116:281-286, 2013.
Williams and Lee, "Field-flow fractionation of proteins, polysaccharides, synthetic polymers, and supramolecular assemblies," J. Sep. Sci., 29:1720-1732, 2006.
Wincott et al., "Synthesis, deprotection, analysis and purification of RNA and ribozymes", Nucleic Acids Res., 23(14): 2677, 1995.

(56) References Cited

OTHER PUBLICATIONS

Zhao et al., "Multiple injections of electroporated autologous T cells expressing a chimeric antigen receptor mediate regression of human disseminated tumor," Cancer Res., 70(22):9053-9061, 2010.
Zhao et al., "Multiple injections of electroporated autologous T cells expressing a chimeric antigen receptor mediate regression of human disseminated tumor," Supplementary Methods, Cancer Res., 70(22):9053-9061, 2010.
Zou et al., "Engineered RNase P ribozymes are efficient in cleaving a human cytomegalovirus mRNA in vitro and are effective in inhibiting viral gene expression and growth in human cells", J. of Biological Chemistry, 278(39): 37265, 2003.
Anonymous, "Cross Flow Filtration Method Handbook," *GE Life Sciences*, pp. 1-82, 2014.
Azarani et al., "RNA analysis by ion-pair reversed-phase high performance liquid chromatography," *Nucleic Acids Research*, 29:2e7, 2000.
Beckert, RNA Methods and Protocols; 2011; Chapter 3; pp. 29-42.
Data submitted by Applicant in corresponding European Patent Application No. 16729807.4, submitted Jan. 29, 2019.
Eon-Duval et al., "Removal of RNA impurities by tangential flow filtration in an RNase-free plasmid DNA purification process," *Anal. Biochem.*, 316(1):66-73, 2003.
International Preliminary Report on Patentability issued in corresponding PCT Application No. PCT/EP2016/062152, dated Dec. 5, 2017.
International Search Report and Written Opinion issued in corresponding PCT Application No. PCT/EP2016/062152, dated Sep. 12, 2016.
Karikd et al., "Generating the optimal mRNA for therapy: HPLC purification eliminates immune activation and improves translation of nucleoside-modified, protein-encoding mRNA", *Nucleic Acids Res.*, 39(21):e142, 2011.
Nestola et al., "Evaluation of a novel large cut-off ultrafiltration membranes for adenovirus serotype 5 (Ad5) concentration," *PLoS One*, 9(12):1-22, 2014.
Office Action issued in corresponding European Patent Application No. 16729807.4, dated Sep. 28, 2018.
Office Communication issued in U.S. Appl. No. 15/580,092, dated Apr. 19, 2019.
Office Communication issued in U.S. Appl. No. 15/580,092, dated Jul. 31, 2019.
Office Communication issued in U.S. Appl. No. 15/580,092, dated Dec. 10, 2019.
Office Communication issued in U.S. Appl. No. 15/580,092, dated Mar. 26, 2020.
Office Communication issued in U.S. Appl. No. 15/580,092, dated Apr. 22, 2020.
Office Communication issued in U.S. Appl. No. 16/934,279, dated Sep. 23, 2021.
Office Communication issued in U.S. Appl. No. 16/934,279, dated Jan. 6, 2022.
Response to Office Action submitted in corresponding European Patent Application No. 16729807.4, dated Jan. 29, 2019.
Manzano et al., "Plasmid DNA pre-purification by tangential flow filtration," *Biotechnology & Biotechnologiool Equipment*, 29(3):586-591, 2015.

\* cited by examiner

A
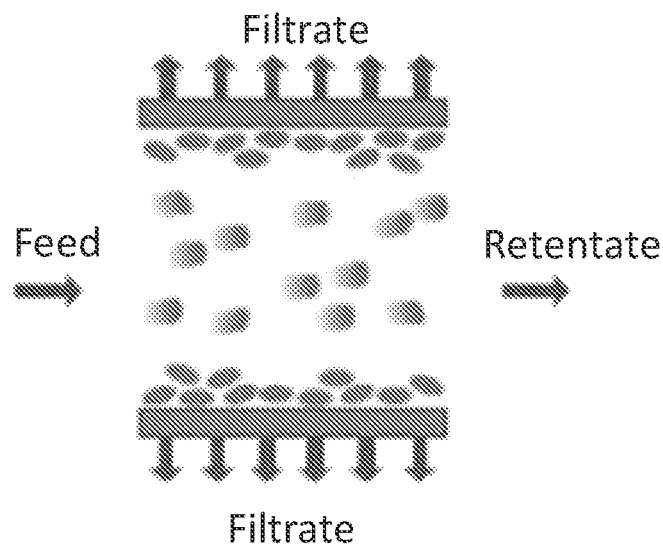
B
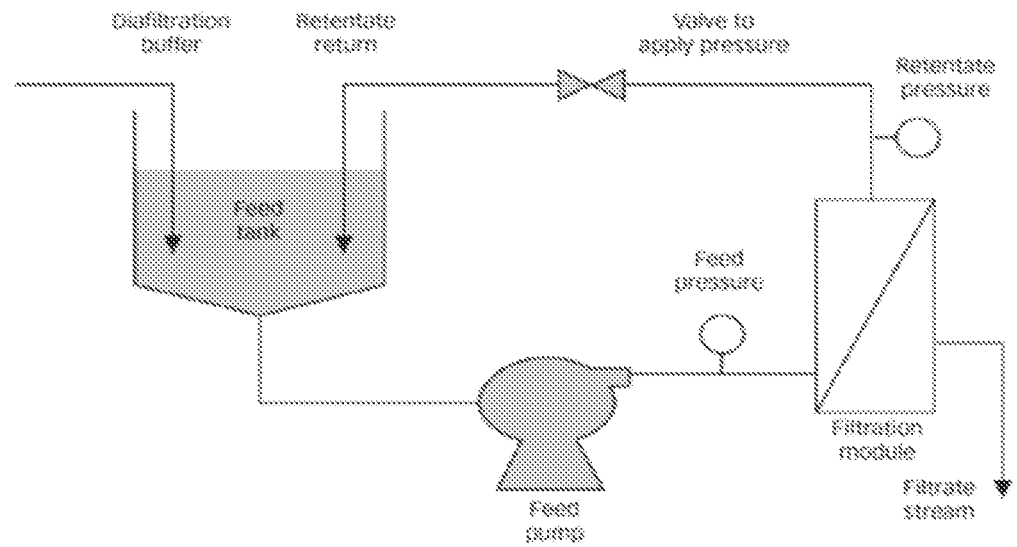
FIGS. 1A-B

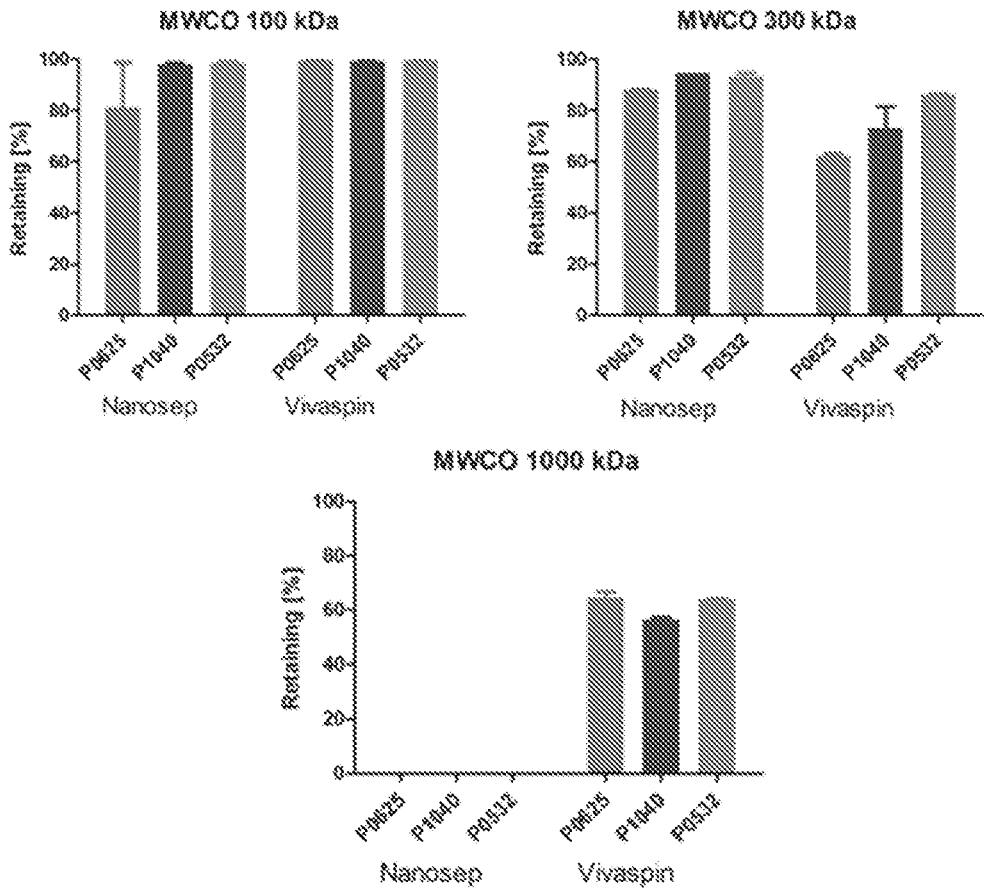
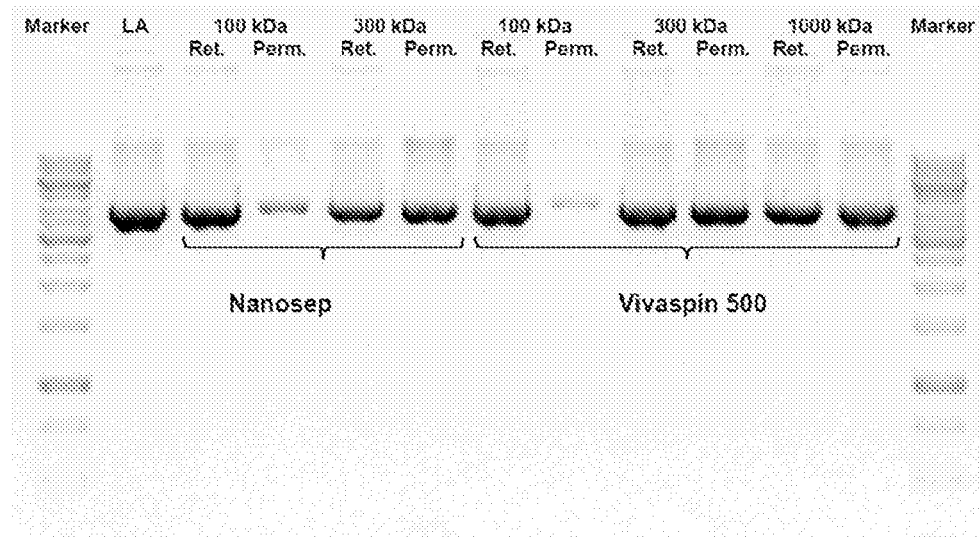
FIGS. 2A-B

A
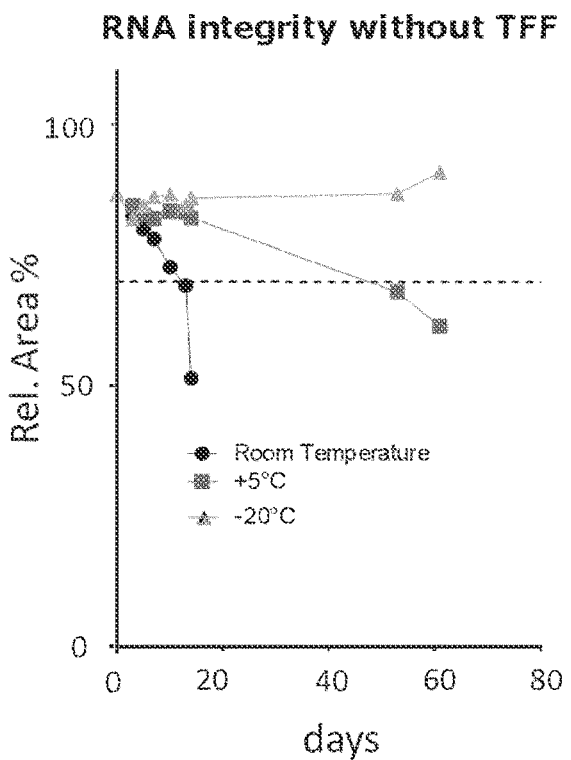
B
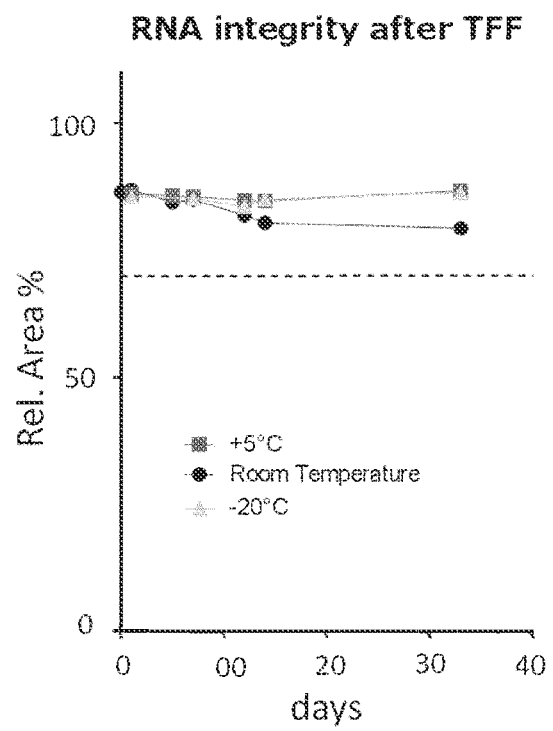
Figure 6

FIGS. 8A-B

METHOD FOR PRODUCING AND PURIFYING RNA, COMPRISING AT LEAST ONE STEP OF TANGENTIAL FLOW FILTRATION

This application is a continuation of U.S. application Ser. No. 17/591,978, filed Feb. 3, 2022, which is a continuation of U.S. application Ser. No. 16/934,279, filed Jul. 21, 2020, which is a continuation of U.S. application Ser. No. 15/580,092, filed Dec. 6, 2017, now U.S. Pat. No. 10,760,070, which is a national phase application under 35 U.S.C. § 371 of International Application No. PCT/EP2016/062152, filed May 30, 2016, which claims benefit of International Application No. PCT/EP2015/062002, filed May 29, 2015, the entire contents of each of which are hereby incorporated by reference.

This invention was made with government support under HR0011-11-3-0001 awarded by the Defense Advanced Research Projects Agency. The government has certain rights in the invention.

TECHNICAL FIELD

The present invention relates to methods of tangential flow filtration (TFF) for producing and purifying RNA.

BACKGROUND OF THE INVENTION

RNA is emerging as an innovative candidate for a variety of pharmaceutical applications, but efficient purification is continuing to be a challenge. This is partly due to the different types and combinations of undesired contaminants in a sample that need to be separated from a desired RNA species to obtain a pure RNA sample. Such contaminants are typically components and byproducts of any upstream processes, for example RNA manufacture. Where in vitro transcription is used to manufacture large RNA, following successful transcription the sample typically contains the desired RNA species alongside various contaminants such as undesired RNA species, proteins, spermidine, DNA or fragments thereof, pyrophosphates, free nucleotides, endotoxins, detergents, and organic solvents.

Commercial downstream applications (e.g. formulation and use as a pharmaceutical composition and/or vaccine) pose further constrains on any purification method for RNA requiring (i) a high degree of purity while retaining RNA stability and functionality; (ii) compatibility with any formulation requirements of the RNA for in vivo delivery; and (iii) compliance with good manufacturing practices. Furthermore, in order to facilitate industrial applications, any RNA purification method must enable consistent, cost- and time-efficient operation (e.g. quick, easy, reproducible, high yield purification on a large scale).

RNA precipitation allows sample concentration as well as depletion of contaminating high molecular weight contaminants and low molecular weight contaminants (e.g. proteins and spermidine, respectively). However, precipitation is not the method of choice in large-scale production processes since precipitation and resolubilization of nucleic acids is time consuming. Moreover, the use of alcohols and other organic solvents should be avoided in large-scale (good) manufacturing processes.

Methods for the purification of RNA are known in the art. Pascolo et al. (Methods Mol Med 2006; 127:23-40) describes a method for the purification of mRNA from an in vitro transcription reaction sample in analytical scale (purification of 25 µg RNA in 20 µl sample volume). The method involves DNase treatment followed by precipitation of the longer mRNA with lithium chloride. However, the authors report that this method does not provide RNA of high purity, as it does not completely remove contaminants such as DNA and protein. Furthermore, the method involves the use of organic solvents and is laborious and time-consuming, involving as many as 36 steps requiring extensive manual sample handling at different conditions, including at least one overnight incubation step. Therefore, while this procedure may satisfy requirements for research and laboratory-scale RNA purification, it suffers from a low degree of RNA purity, reproducibility and is unsuitable for purification of pharmaceutical-grade RNA on a commercial scale for implementation in an industrial process.

WO2008/077592 discloses a method for purifying RNA on a preparative scale with ion-pairing reverse phase HPLC using a porous reversed stationary phase. It is reported that a particular advantage of using the specified porous stationary phase is that excessively high pressures can be avoided, facilitating a preparative purification of RNA.

WO2014/140211 discloses a method for purifying large RNA from a sample, comprising steps of tangential flow filtration, hydroxyapatite chromatography, core bead flow-through chromatography or any combinations thereof. It is also disclosed that it is preferred that no salts, other than buffering salts, are added to the buffer for the tangential flow filtration. The tangential flow filtration is performed using a hollow fibre membrane. However, the described nucleic acid loading amounts of the membrane are very low and would therefore require huge membrane areas for the large-scale production (g to kg) of mRNA.

WO2014/152966 discloses a method for purifying in vitro transcribed RNA, wherein after RNA in vitro transcription the reaction mixture is treated with a protein denaturing agent such as urea and then subjected to tangential flow filtration using a hollow fiber membrane.

There remains a need for further RNA purification methods, and in particular for those that allow cost- and time-efficient purification of RNAs at an industrial scale with high yield and pharmaceutical-grade purity, stability and/or shelf life.

It is thus an object of the present invention to provide further RNA production and purification methods suitable for large scale RNA preparation.

SUMMARY

The objective is solved by a method for producing and purifying RNA, comprising the steps of
A) providing DNA encoding the RNA;
B) transcription of the DNA to yield a solution comprising transcribed RNA; and
C) conditioning and/or purifying of the solution comprising transcribed RNA by one or more steps of tangential flow filtration (TFF).

Definitions

For the sake of clarity and readability the following definitions are provided. Any technical feature mentioned for these definitions may be read on each and every embodiment of the invention. Additional definitions and explanations may be specifically provided in the context of these embodiments.

Enzyme: Enzymes are catalytically active biomolecules that perform biochemical reactions such as DNA dependent RNA transcription (e.g. RNA polymerases), or double stranded DNA digestion (e.g. restriction endonucleases). Enzymes are typically composed of amino acids and/or RNA (ribozymes, snRNA).

Restriction endonucleases: Restriction endonucleases or restriction enzymes are a class of enzymes that occur naturally in bacteria and in some viruses. Restriction endonucleases can be used in the laboratory to cleave DNA molecules into smaller fragments for molecular cloning and gene characterization. Restriction enzymes bind specifically to and cleave double-stranded DNA at specific sites within or adjacent to a particular sequence known as the recognition site. Most of the restriction enzymes recognize a specific sequence of nucleotides that are four, five or six nucleotides in length and display twofold symmetry. Some cleave both strands exactly at the axis of symmetry, generating fragments of DNA that carry blunt ends; others cleave each strand at similar locations on opposite sides of the axis of symmetry, creating fragments of DNA that carry single-stranded termini (cohesive ends). The restriction endonucleases are categorized into four groups (Types I, II, III, and IV) based on their composition and enzyme cofactor requirements, the nature of their target sequence, and the position of their DNA cleavage site relative to the target sequence. All types of enzymes recognize specific short DNA sequences and carry out the cleavage of DNA, yielding specific fragments with terminal 5'-phosphates. Restriction endonucleases recognize and bind particular sequences of nucleotides (the 'recognition site') on DNA molecules. Once bound, they cleave the molecule within (e.g., BamHI), to one side of (e.g., SapI), or to both sides (e.g., TspRI) of the recognition sequence. Particularly preferred is the use of the following restriction enzymes: BciVI (BfuI), BcuI (SpeI), EcoRI, AatII, AgeI (BshTI), ApaI, BamHI, BglII, BlpI (Bpu1102I), BsrGI (Bsp1407), ClaI (Bsu15I), EcoRI, EcoRV (Eco32I), HindIII, KpnI, MluI, NcoI, NdeI, NheI, NotI, NsiI, Mph1103I), PstI, PvuI, PvuII, SacI, SalI, ScaI, SpeI, XbaI, XhoI, SacII (Cfr42I), XbaI. Restriction enzymes recognize short DNA sequences and cleave double-stranded DNA at specific sites within or adjacent to these sequences. Approximately 3,000 restriction enzymes, recognizing over 230 different DNA sequences, have been discovered. They have been found mostly in bacteria, but have also been isolated from viruses, archaea and eukaryotes. A list of known restriction enzymes can be found at the rebase database: http://rebase.neb.com/rebase/rebase.html Restriction site: A restriction site, also called restriction enzyme recognition site, is a nucleotide sequence recognized by a restriction enzyme. A restriction site is typically a short, preferably palindromic nucleotide sequence, e.g. a sequence comprising 4 to 8 nucleotides. A restriction site is preferably specifically recognized by a restriction enzyme. The restriction enzyme typically cleaves a nucleotide sequence comprising a restriction site at this site. In a double-stranded nucleotide sequence, such as a double-stranded DNA sequence, the restriction enzyme typically cuts both strands of the nucleotide sequence. Most restriction endonucleases recognize palindromic or partially palindromic sites. A palindrome is defined as dyad symmetry around an axis. For example, EcoRI digestion produces "sticky" ends, whereas SmaI restriction enzyme cleavage produces "blunt" ends. Recognition sequences in DNA differ for each restriction enzyme, producing differences in the length, sequence and strand orientation (5' end or the 3' end) of a sticky-end "overhang" of an enzyme restriction. Different restriction enzymes that recognize the same sequence are known as neoschizomers. These often cleave in different locales of the sequence. Different enzymes that recognize and cleave in the same location are known as isoschizomers.

Protein: A protein typically comprises one or more peptides or polypeptides. A protein is typically folded into 3-dimensional form, which may be required for the protein to exert its biological function. The sequence of a protein or peptide is typically understood to be the order, i.e. the succession of its amino acids.

Recombinant protein: The term 'recombinant protein' refers to proteins that have been produced in a heterologous system, that is, in an organism that naturally does not produce such a protein, or a variant of such a protein. Alternatively, the organism may naturally produce the protein, but in lower amounts so that the recombinant expression increases the amount of said protein. Typically, the heterologous systems used in the art to produce recombinant proteins are bacteria (e.g., *Escherichia coli*), yeast (e.g., *Saccharomyces cerevisiae*) or certain mammalian cell culture lines.

Plasmid DNA (vectors): The term 'plasmid DNA' or 'plasmid DNA vector' refers to a circular nucleic acid molecule, preferably to an artificial nucleic acid molecule. A plasmid DNA in the context of the present invention is suitable for incorporating or harboring a desired nucleic acid sequence, such as a nucleic acid sequence comprising a sequence encoding an RNA and/or an open reading frame encoding at least one peptide or polypeptide. Such plasmid DNA constructs/vectors may be storage vectors, expression vectors, cloning vectors, transfer vectors etc. A storage vector is a vector, which allows the convenient storage of a nucleic acid molecule, for example, of an RNA molecule. Thus, the plasmid DNA may comprise a sequence corresponding (coding for), e.g., to a desired RNA sequence or a part thereof, such as a sequence corresponding to the open reading frame and the 5'- and/or 3'UTR of an mRNA. An expression vector may be used for production of expression products such as RNA, e.g. mRNA in a process called RNA in vitro transcription. For example, an expression vector may comprise sequences needed for RNA in vitro transcription of a sequence stretch of the vector, such as a promoter sequence, e.g. an RNA promoter sequence, preferably T3, T7 or SP6 RNA promotor sequences. A cloning vector is typically a vector that contains a cloning site, which may be used to incorporate nucleic acid sequences (insert) into the vector. A cloning vector may be, e.g., a plasmid vector or a bacteriophage vector. A transfer vector may be a vector, which is suitable for transferring nucleic acid molecules into cells or organisms, for example, viral vectors. Preferably, a plasmid DNA vector in the sense of the present invention comprises a multiple cloning site, an RNA promoter sequence, optionally a selection marker, such as an antibiotic resistance factor, and a sequence suitable for multiplication of the vector, such as an origin of replication. Particularly preferred in the context of the present invention are plasmid DNA vectors, or expression vectors, comprising promoters for DNA-dependent RNA polymerases such as T3, T7 and Sp6. As plasmid backbone, particularly preferred are pUC19 and pBR322.

Template DNA: As used herein, the term 'template DNA' (or 'DNA template') typically relates to a DNA molecule comprising a nucleic acid sequence encoding the RNA sequence to be in vitro transcribed. The template DNA is used as template for in vitro transcription in order to produce the RNA encoded by the template DNA. Therefore, the template DNA comprises all elements necessary for in vitro transcription, particularly a promoter element for binding of a DNA dependent RNA polymerase as e.g. T3, T7 and SP6 RNA polymerases 5' of the DNA sequence encoding the target RNA sequence. Furthermore the template DNA may comprise primer binding sites 5' and/or 3' of the DNA sequence encoding the target RNA sequence to determine the identity of the DNA sequence encoding the target RNA sequence e.g. by PCR or DNA sequencing. As used herein, the term 'template DNA' may also refer to a DNA vector, such as a plasmid DNA, which comprises a nucleic acid sequence encoding the RNA sequence. Further, the 'template DNA' in the context of the present invention may be a linear or a circular DNA molecule.

Target Sequence: A 'target sequence' as used herein is typically understood as the sequence of the RNA, which is encoded by the nucleic acid sequence comprised in the template DNA. The target sequence is thus the sequence to be synthesized by in vitro transcription, e.g. a protein-coding sequence or another RNA as defined herein like isRNA, antisense RNA etc.

Linear template DNA plasmid: The linear template DNA plasmid is obtained by contacting the plasmid DNA with a restriction enzyme under suitable conditions so that the restriction enzyme cuts the plasmid DNA at its recognition site(s) and disrupts the plasmid structure. This reaction is called linearization reaction. Hence, the linear template DNA comprises a free 5' end and a free 3' end, which are not linked to each other. If the plasmid DNA contains only one recognition site for the restriction enzyme, the linear template DNA has the same number of nucleotides as the plasmid DNA. If the plasmid DNA contains more than one recognition site for the restriction enzyme, the linear template DNA has a smaller number of nucleotides than the plasmid DNA. The linear template DNA is then the fragment of the plasmid DNA, which contains the elements necessary for RNA in vitro transcription, that is a promoter element for RNA transcription and the template DNA element. The DNA sequence encoding the target RNA sequence of the linear template DNA determines the sequence of the transcribed RNA by the rules of base-pairing.

5'-cap: A 5'-cap is an entity, typically a modified nucleotide entity, which generally "caps" the 5'-end of a mature mRNA. A 5'-cap may typically be formed by a modified nucleotide (cap analog), particularly by a derivative of a guanine nucleotide. Preferably, the 5'-cap is linked to the 5'-terminus via a 5'-5'-triphosphate linkage. A 5'-cap may be methylated, e.g. m7GpppN (e.g. m7G(5')ppp(5')G (m7G)), wherein N is the terminal 5' nucleotide of the nucleic acid carrying the 5'-cap, typically the 5'-end of an RNA. Further examples of 5'cap structures include glyceryl, inverted deoxy abasic residue (moiety), 4',5' methylene nucleotide, 1-(beta-D-erythrofuranosyl) nucleotide, 4'-thio nucleotide, carbocyclic nucleotide, 1,5-anhydrohexitol nucleotide, L-nucleotides, alpha-nucleotide, modified base nucleotide, threo-pentofuranosyl nucleotide, acyclic 3',4'-seco nucleotide, acyclic 3,4-dihydroxybutyl nucleotide, acyclic 3,5 dihydroxypentyl nucleotide, 3'-3'-inverted nucleotide moiety, 3'-3'-inverted abasic moiety, 3'-2'-inverted nucleotide moiety, 3'-2'-inverted abasic moiety, 1,4-butanediol phosphate, 3'-phosphoramidate, hexylphosphate, aminohexyl phosphate, 3'-phosphate, 3'phosphorothioate, phosphorodithioate, or bridging or non-bridging methylphosphonate moiety. Further modified 5'-CAP structures which may be used in the context of the present invention are CAP1 (methylation of the ribose of the adjacent nucleotide of m7GpppN), CAP2 (methylation of the ribose of the 2nd nucleotide downstream of the m7GpppN), CAP3 (methylation of the ribose of the 3rd nucleotide downstream of the m7GpppN), CAP4 (methylation of the ribose of the 4th nucleotide downstream of the m7GpppN), ARCA (anti-reverse CAP analogue, modified ARCA (e.g. phosphothioate modified ARCA), inosine, N1-methyl-guanosine, 2'-fluoro-guanosine, 7-deaza-guanosine, 8-oxo-guanosine, 2-amino-guanosine, LNA-guanosine, and 2-azido-guanosine.

Poly(A) sequence: A poly(A) sequence, also called poly (A) tail or 3'-poly(A) tail, is typically understood to be a sequence of adenine nucleotides, e.g., of up to about 400 adenine nucleotides, e.g. from about 20 to about 400, preferably from about 50 to about 400, more preferably from about 50 to about 300, even more preferably from about 50 to about 250, most preferably from about 60 to about 250 adenine nucleotides. A poly(A) sequence is typically located at the 3'end of an mRNA. In the context of the present invention, a poly(A) sequence may be located within an mRNA or any other nucleic acid molecule, such as, e.g., in a vector, for example, in a vector serving as template for the generation of an RNA, preferably an mRNA, e.g., by transcription of the vector.

RNA, mRNA: RNA is the usual abbreviation for ribonucleic acid. It is a nucleic acid molecule, i.e. a polymer consisting of nucleotide monomers. These nucleotides are usually adenosine-monophosphate, uridine-monophosphate, guanosine-monophosphate and cytidine-monophosphate monomers, which are connected to each other along a so-called backbone. The backbone is formed by phosphodiester bonds between the sugar, i.e. ribose, of a first and a phosphate moiety of a second, adjacent monomer. The specific order of the monomers, i.e. the order of the bases linked to the sugar/phosphate-backbone, is called the RNA-sequence. Usually RNA may be obtainable by transcription of a DNA-sequence, e.g., inside a cell. In eukaryotic cells, transcription is typically performed inside the nucleus or the mitochondria. In vivo, transcription of DNA usually results in the so-called premature RNA, which has to be processed into so-called messenger-RNA, usually abbreviated as mRNA. Processing of the premature RNA, e.g. in eukaryotic organisms, comprises a variety of different posttranscriptional-modifications such as splicing, 5'-capping, polyadenylation, export from the nucleus or the mitochondria and the like. The sum of these processes is also called maturation of RNA. The mature messenger RNA usually provides the nucleotide sequence that may be translated into an amino acid sequence of a particular peptide or protein. Typically, a mature mRNA comprises a 5'-cap, optionally a 5'UTR, an open reading frame, optionally a 3'UTR and a poly(A) sequence. Aside from messenger RNA, several non-coding types of RNA exist which may be involved in regulation of transcription and/or translation, and immunostimulation. The term "RNA" further encompass other coding RNA molecules, such as viral RNA, retroviral RNA and replicon RNA, small interfering RNA (siRNA), antisense RNA, CRISPR RNA, ribozymes, aptamers, riboswitches, immunostimulating RNA, transfer RNA (tRNA), ribosomal RNA (rRNA), small nuclear RNA (snRNA), small nucleolar RNA (snoRNA), microRNA (miRNA), and Piwi-interacting RNA (piRNA).

5'-untranslated region (5'-UTR): As used herein, the term '5'-UTR' typically refers to a particular section of messenger RNA (mRNA). It is located 5' of the open reading frame of the mRNA. Typically, the 5'-UTR starts with the transcriptional start site and ends one nucleotide before the start codon of the open reading frame. The 5'-UTR may comprise elements for controlling gene expression, also called regulatory elements. Such regulatory elements may be, for example, ribosomal binding sites or a 5'-Terminal Oligopyrimidine Tract. The 5'-UTR may be posttranscriptionally modified, for example by addition of a 5'-CAP. In the context of the present invention, a 5'-UTR corresponds to the sequence of a mature mRNA, which is located between the 5'-CAP and the start codon. Preferably, the 5'-UTR corresponds to the sequence, which extends from a nucleotide located 3' to the 5'-CAP, preferably from the nucleotide located immediately 3' to the 5'-CAP, to a nucleotide located 5' to the start codon of the protein coding region, preferably to the nucleotide located immediately 5' to the start codon of the protein coding region. The nucleotide located immediately 3' to the 5'-CAP of a mature mRNA typically corresponds to the transcriptional start site. The term "corresponds to" means that the 5'-UTR sequence may be an RNA sequence, such as in the mRNA sequence used for defining the 5'-UTR sequence, or a DNA sequence, which corresponds to such RNA sequence. In the context of the present invention, the term "a 5'-UTR of a gene", such as "a 5'-UTR of a TOP gene", is the sequence, which corresponds to the 5'-UTR of the mature mRNA derived from this gene, i.e. the mRNA obtained by transcription of the gene and maturation of the pre-mature mRNA. The term "5'-UTR of a gene" encompasses the DNA sequence and the RNA sequence of the 5'-UTR. Preferably, the 5'-UTR used according to the present invention is heterologous to the coding region of the mRNA sequence. Even if 5'-UTR's derived from naturally occurring genes are preferred, also synthetically engineered UTR's may be used in the context of the present invention.

3'-untranslated region (3'-UTR): In the context of the present invention, a 3'-UTR is typically the part of an mRNA, which is located between the protein coding region (i.e. the open reading frame) and the 3'-terminus of the mRNA. A 3'-UTR of an mRNA is not translated into an amino acid sequence. The 3'-UTR sequence is generally encoded by the gene, which is transcribed into the respective mRNA during the gene expression process. In the context of the present invention, a 3'-UTR corresponds to the sequence of a mature mRNA, which is located 3' to the stop codon of the protein coding region, preferably immediately 3' to the stop codon of the protein coding region, and which extends to the 5'-side of the 3'-terminus of the mRNA or of the poly(A) sequence, preferably to the nucleotide immediately 5' to the poly(A) sequence. The term "corresponds to" means that the 3'-UTR sequence may be an RNA sequence, such as in the mRNA sequence used for defining the 3'-UTR sequence, or a DNA sequence, which corresponds to such RNA sequence. In the context of the present invention, the term "a 3'-UTR of a gene", such as "a 3'-UTR of an albumin gene", is the sequence, which corresponds to the 3'-UTR of the mature mRNA derived from this gene, i.e. the mRNA obtained by transcription of the gene and maturation of the pre-mature mRNA. The term "3'-UTR of a gene" encompasses the DNA sequence and the RNA sequence of the 3'-UTR. Preferably, the 3'-UTR used according to the present invention is heterologous to the coding region of the mRNA sequence. Even if 3'-UTR's derived from naturally occurring genes are preferred, also synthetically engineered UTR's may be used in the context of the present invention.

In vitro transcribed RNA: An in vitro transcribed RNA is an RNA molecule that has been synthesized from a template DNA, commonly a linearized and purified plasmid template DNA, a PCR product, or an oligonucleotide. RNA synthesis occurs in a cell free ("in vitro") assay catalyzed by DNA dependent RNA polymerases. In a process called RNA in vitro transcription, virtually all nucleotides analogues into RNA. Particular examples of DNA dependent RNA polymerases are the T7, T3, and SP6 RNA polymerases. An in vitro transcribed RNA may comprise elements such as 5'-cap, optionally a 5'UTR, an open reading frame, optionally a 3'UTR and a poly(A) sequence. Aside from proteinogenic messenger RNA, several non-coding types of RNA exist which may be involved in regulation of transcription and/or translation. Such All RNA molecules as defined herein may also be synthesized by RNA in vitro transcription.

RNA species: The term "RNA species" denotes a group of the same RNA molecules which are similar in their RNA sequence and/or their sequence length. Hence, the RNA molecules within one RNA species are encoded by the same template DNA. If the RNA present within the sample is a coding RNA, one RNA species encodes one target peptide or protein.

DNA: DNA is the usual abbreviation for deoxy-ribo-nucleic-acid. It is a nucleic acid molecule, i.e. a polymer consisting of nucleotide monomers. These nucleotides are usually deoxy-adenosine-monophosphate, deoxy-thymidine-monophosphate, deoxy-guanosine-monophosphate and deoxy-cytidine-monophosphate monomers which are—by themselves—composed of a sugar moiety (deoxyribose), a base moiety and a phosphate moiety, and polymerise by a characteristic backbone structure. The backbone structure is, typically, formed by phosphodiester bonds between the sugar moiety of the nucleotide, i.e. deoxyribose, of a first and a phosphate moiety of a second, adjacent monomer. The specific order of the monomers, i.e. the order of the bases linked to the sugar/phosphate-backbone, is called the DNA-sequence. DNA may be single-stranded or double-stranded. In the double stranded form, the nucleotides of the first strand typically hybridize with the nucleotides of the second strand, e.g. by A/T-base-pairing and G/C-base-pairing.

Cloning site, multiple cloning site: A cloning site is typically understood to be a segment of a nucleic acid molecule, which is suitable for insertion of a nucleic acid sequence, e.g., a nucleic acid sequence comprising an open reading frame. Insertion may be performed by any molecular biological method known to the one skilled in the art, e.g. by restriction and ligation. A cloning site typically comprises one or more restriction enzyme recognition sites (restriction sites). These one or more restrictions sites may be recognized by restriction enzymes which cleave the DNA at these sites. A cloning site which comprises more than one restriction site may also be termed a multiple cloning site (MCS) or a polylinker.

Open reading frame: An open reading frame (ORF) in the context of the invention may typically be a sequence of several nucleotide triplets, which may be translated into a peptide or protein. An open reading frame preferably contains a start codon, i.e. a combination of three subsequent nucleotides coding usually for the amino acid methionine (ATG), at its 5'-end and a subsequent region, which usually exhibits a length which is a multiple of 3 nucleotides. An ORF is preferably terminated by a stop-codon (e.g., TAA, TAG, TGA). Typically, this is the only stop-codon of the open reading frame. Thus, an open reading frame in the context of the present invention is preferably a nucleotide sequence, consisting of a number of nucleotides that may be divided by three, which starts with a start codon (e.g. ATG) and which preferably terminates with a stop codon (e.g., TAA, TGA, or TAG). The open reading frame may be isolated or it may be incorporated in a longer nucleic acid sequence, for example in a vector or an mRNA. An open reading frame may also be termed "protein coding region".

RNA in vitro transcription: The term "RNA in vitro transcription" (or 'in vitro transcription') relates to a process wherein RNA, in particular mRNA, is synthesized in a cell-free system (in vitro). Preferably, cloning vectors DNA, particularly plasmid DNA vectors are applied as template for the generation of RNA transcripts. These cloning vectors are generally designated as transcription vector. RNA may be obtained by DNA dependent in vitro transcription of an appropriate DNA template, which according to the present invention is preferably a linearized plasmid DNA template. The promoter for controlling RNA in vitro transcription can be any promoter for any DNA dependent RNA polymerase. Particular examples of DNA dependent RNA polymerases are the T7, T3, and SP6 RNA polymerases. A DNA template for RNA in vitro RNA transcription may be obtained by cloning of a nucleic acid, in particular cDNA corresponding to the respective RNA to be in vitro transcribed, and introducing it into an appropriate vector for RNA in vitro transcription, for example in plasmid circular plasmid DNA. The cDNA may be obtained by reverse transcription of mRNA or chemical synthesis. Moreover, the DNA template for in vitro RNA synthesis may also be obtained by gene synthesis. Preferably cloning vectors are used for RNA in vitro RNA transcription, which are generally designated transcription vectors.

Kozak sequence: As used herein, the term 'Kozak sequence' typically refers to a sequence on an mRNA molecule, which is recognized by the ribosome as the translational start site of a protein encoded by that mRNA molecule. In a preferred embodiment, that sequence may comply with a consensus sequence for a nucleotide sequence mediating initiation of translation, preferably with the consensus sequence (gcc)gccRccAUGG, wherein a lower case letter denotes the most common base at a position where the base can nevertheless vary; upper case letters indicate highly conserved bases, 'AUGG'; 'R' indicates that a purine (adenine or guanine, preferably adenine) is present at this position; and the sequence in brackets is of uncertain significance.

HPLC: High-performance liquid chromatography (HPLC; formerly referred to as high-pressure liquid chromatography), is a technique in analytic chemistry used to separate the components in a mixture, to identify each component, and to quantify each component. It relies on pumps to pass a pressurized liquid solvent containing the sample mixture through a column filled with a solid adsorbent material. Each component in the sample interacts slightly differently with the adsorbent material, causing different flow rates for the different components and leading to the separation of the components as they flow out the column. HPLC is distinguished from traditional ("low pressure") liquid chromatography because operational pressures are significantly higher (50-350 bar), while ordinary liquid chromatography typically relies on the force of gravity to pass the mobile phase through the column. Due to the small sample amount separated in analytical HPLC, typical column dimensions are 2.1-4.6 mm diameter, and 30-250 mm length. Also HPLC columns are made with smaller sorbent particles (2-50 micrometer in average particle size). This gives HPLC superior resolving power when separating mixtures, which is why it is a popular chromatographic technique. The schematic of an HPLC instrument typically includes a sampler, pumps, and a detector. The sampler brings the sample mixture into the mobile phase stream which carries it into the column. The pumps deliver the desired flow and composition of the mobile phase through the column. The detector generates a signal proportional to the amount of sample component emerging from the column, hence allowing for quantitative analysis of the sample components. A digital microprocessor and user software control the HPLC instrument and provide data analysis. Some models of mechanical pumps in a HPLC instrument can mix multiple solvents together in ratios changing in time, generating a composition gradient in the mobile phase. Various detectors are in common use, such as UV/Vis, photodiode array (PDA) or based on mass spectrometry. Most HPLC instruments also have a column oven that allows for adjusting the temperature the separation is performed at.

Lyophilization: Freeze-drying, also known as lyophilization, or cryodesiccation, is a dehydration process typically used to preserve a perishable material or make the material more convenient for transport. Freeze-drying works by freezing the material and then reducing the surrounding pressure to allow the frozen water in the material to sublimate directly from the solid phase to the gas phase.

Conditioning: the term "conditioning" comprises providing a compound, such as RNA or DNA, in a suitable form, e.g. a suitable buffer or solvent, suitable concentration or suitable biochemical or biophysical properties. The conditioning may for example be performed using TFF, e.g. in a concentration and/or diafiltration step. Therefore, conditioning includes concentration and exchange of buffer or solvent by diafiltration.

Purification: as used herein, the term "purification" or "purifying" or "pure" is understood to mean that the desired RNA or DNA in a sample is separated and/or isolated from impurities, intermediates, byproducts and/or reaction components present therein or that the impurities, intermediates, byproducts and/or reaction components are at least depleted from the sample comprising the RNA or DNA. Non-limiting examples of undesired constituents of RNA- or DNA-containing samples which therefore need to be depleted may comprise degraded fragments or fragments which have arisen as a result of premature termination of transcription, or also excessively long transcripts if plasmids are not completely linearized. Furthermore, intermediates may be depleted from the sample such as e.g. template DNA. Additionally, reaction components such as enzymes, proteins, bacterial DNA and RNA, small molecules such as spermidine, buffer components etc. may have to be depleted from the RNA/DNA sample. In addition, impurities such as, organic solvents, and nucleotides or other small molecules may be separated. Ideally, the RNA has a higher purity and/or integrity after purification than the starting material. The purity may be determined by methods commonly known to the skilled person, e.g. by gas chromatography, quantitative PCR, analytical HPLC or gel electrophoresis.

Tangential Flow Filtration (TFF) or Crossflow Filtration: Crossflow filtration (also known as tangential flow filtration) is a type of filtration. Crossflow filtration is different from dead-end filtration in which the feed is passed through a membrane or bed, the solids being trapped in the filter and the filtrate being released at the other end. Cross-flow filtration gets its name because the majority of the feed flow travels tangentially across the surface of the filter, rather than into the filter. The principal advantage of this is that the filter cake (which can blind the filter) is substantially washed away during the filtration process, increasing the length of time that a filter unit can be operational. It can be a continuous process, unlike batch-wise dead-end filtration. This type of filtration is typically selected for feeds containing a high proportion of small particle size solids (where the permeate is of most value) because solid material can quickly block (blind) the filter surface with dead-end filtration. Applied pressure causes one portion of the flow stream to pass through the membrane (filtrate/permeate) while the remainder (retentate) is recirculated back to the feed reservoir. The general working principle of TFF can be found in literature, see e.g. Fernandez et al. (A BIOTECHNO-LOGICA, Bd. 12, 1992, Berlin, Pages 49-56) or Rathore, A S et al (Prep Biochem Biotechnol. 2011; 41(4):398-421). Further, the principle of TFF is illustrated in FIG. 1. The primary applications for TFF are concentration, diafiltration (desalting and buffer/solvent exchange), and fractionation of large from small biomolecules. Membranes with different molecular weight cutoffs (MWCO) may be used for TFF. In the context of the present invention ultrafiltration membranes are preferably used for TFF.

Two basic filter configurations are generally used for TFF. In cartridge filters (often called hollow fiber filters), the membrane forms a set of parallel hollow fibers. The feed stream passes through the lumen of the fibers and the permeate is collected from outside the fibers. Cartridges are characterized in terms of fiber length, lumen diameter and number of fibers, as well as filter pore size. In cassette filters, several flat sheets of membrane are held apart from each other and from the cassette housing by support screens. The feed stream passes into the space between two sheets and permeate is collected from the opposite side of the sheets. Cassettes are characterized in terms of flow path length and channel height, as well as membrane pore size. The channel height is determined by the thickness of the support screen. Both cartridges and cassettes are constructed from materials chosen for mechanical strength, chemical and physical compatibility, and low levels of extractable and/or toxic compounds.

Ultrafiltration: Ultrafiltration is a filtration method using a membrane in which forces like pressure or concentration gradients lead to a separation through a semipermeable membrane. Suspended solids and solutes of high molecular weight are retained in the so-called retentate, while water and low molecular weight solutes pass through the membrane in the permeate. This separation process is used in industry and research for purifying and concentrating macromolecular ($10^3$-$10^6$ Da) solutions. Ultrafiltration is not fundamentally different from microfiltration. Both of these separate based on size exclusion or particle capture. Ultrafiltration membranes are defined by the molecular weight cut-off (MWCO) of the membrane of between 2 and 100 nm (which corresponds to a MWCO between 1 and 1000 kDa). Ultrafiltration is applied in cross-flow or dead-end mode.

Feed: Material or solution that is fed into the filter, for example the linearization reaction or the RNA in vitro transcription reaction mixture.

Transfer RNA: A transfer RNA is an adaptor molecule composed of RNA, typically 76 to 90 nucleotides in length that serves as the physical link between the nucleotide sequence of nucleic acids (DNA and RNA) and the amino acid sequence of proteins. It does this by carrying an amino acid to the protein synthetic machinery of a cell (ribosome) as directed by a three-nucleotide sequence (codon) in a messenger RNA (mRNA). As such, tRNAs are a necessary component of protein translation, the biological synthesis of new proteins according to the genetic code. The structure of tRNA can be decomposed into its primary structure, its secondary structure (usually visualized as the cloverleaf structure), and its tertiary structure (all tRNAs have a similar L-shaped 3D structure that allows them to fit into the P and A sites of the ribosome). The cloverleaf structure becomes the 3D L-shaped structure through coaxial stacking of the helices, which is a common RNA tertiary structure motif.

Ribosomal RNA (rRNA): the RNA component of the ribosome; rRNA is essential for protein synthesis in all living organisms. It constitutes the predominant material within the ribosome, which is approximately 60% rRNA and 40% protein by weight. Ribosomes contain two major rRNAs and 50 or more proteins. The ribosomal RNAs form two subunits, the large subunit (LSU) and small subunit (SSU). The LSU rRNA acts as a ribozyme, catalyzing peptide bond formation, mRNA is sandwiched between the small and large subunits, and the ribosome catalyzes the formation of a peptide bond between the two amino acids that are contained in the rRNA.

Viral RNA: viral RNA is RNA derived from a virus, for example a retrovirus. It may be directly translated into the desired viral proteins. Portions of the viral RNA may be skipped during translation. The result is that many different proteins can be created from the same mRNA strand, with similar 5' ends (to varying degrees) and same 3' ends. Or, different proteins can be created from positive sense viral RNA and negative sense viral RNA.

Replicons: A replicon is an RNA molecule, or a region of an RNA, that replicates from a single origin of replication.

Antisense-RNA: Antisense RNA (asRNA) or mRNA-interfering complementary RNA (micRNA) is a single-stranded RNA that is complementary to a portion of an mRNA strand transcribed within a cell. Antisense RNA may for example be introduced into a cell to inhibit translation of a complementary mRNA by base pairing to it and physically obstructing the translation machinery.

Immunostimulating RNA (isRNA): An immunostimulating RNA (isRNA) in the context of the invention may typically be a RNA that is able to induce an innate immune response itself. It usually does not have an open reading frame and thus does not provide a peptide-antigen or immunogen but elicits an innate immune response e.g. by binding to a specific kind of Toll-like-receptor (TLR) or other suitable receptors. However, of course also mRNAs having an open reading frame and coding for a peptide/protein (e.g. an antigenic function) may induce an innate immune response.

Small interfering RNA (siRNA): also known as short interfering RNA or silencing RNA, is a class of double-stranded RNA molecules, 20-25 base pairs in length. siRNA plays many roles, but it is most notable in the RNA interference (RNAi) pathway, where it interferes with the expression of specific genes with complementary nucleotide sequences. siRNA functions by causing mRNA to be broken down after transcription, resulting in no translation. siRNA also acts in RNAi-related pathways, e.g., as an antiviral mechanism or in shaping the chromatin structure of a genome. siRNAs have a well-defined structure: a short (usually 20 to 24-bp) double-stranded RNA (dsRNA) with phosphorylated 5' ends and hydroxylated 3' ends with two overhanging nucleotides. The Dicer enzyme catalyzes production of siRNAs from long dsRNAs and small hairpin RNAs.

Ribozyme: Ribozymes are ribonucleic acid enzymes, also termed catalytic RNA. Ribozymes are RNA molecules that are capable of catalyzing specific biochemical reactions, similar to the action of protein enzymes. Ribozymes have diverse structures and mechanisms. Examples of ribozymes include the hammerhead ribozyme, the VS ribozyme, Leadzyme and the hairpin ribozyme.

Aptamers: Aptamers (from the Latin aptus—fit, and Greek meros—part) are RNA-based oligonucleotide molecules that bind to a specific target molecule. Aptamers are usually created by selecting them from a large random sequence pool, but natural aptamers also exist in riboswitches. Aptamers also include RNA-based oligonucleotide molecules that bind to a specific target molecule that are combined with ribozymes to self-cleave in the presence of their target molecule.

CRISPR (clustered regularly interspaced short palindromic repeats): segments of prokaryotic DNA containing short repetitions of base sequences. Each repetition is followed by short segments of "spacer DNA" from previous exposures to a bacterial virus or plasmid. CRISPRs are found in approximately 40% of sequenced bacteria genomes and 90% of sequenced archaea. CRISPRs are often associated with cas genes that code proteins related to CRISPRs. The CRISPR/Cas system is a prokaryotic immune system that confers resistance to foreign genetic elements such as plasmids and phages and provides a form of acquired immunity. CRISPR spacers recognize and cut these exogenous genetic elements in a manner analogous to RNAi in eukaryotic organisms.

Piwi-interacting RNA: the largest class of small non-coding RNA molecules expressed in animal cells. piRNAs form RNA-protein complexes through interactions with piwi proteins. These piRNA complexes have been linked to both epigenetic and post-transcriptional gene silencing of retrotransposons and other genetic elements in germ line cells, particularly those in spermatogenesis. They are distinct from microRNA (miRNA) in size (26-31 nt rather than 21-24 nt), lack of sequence conservation, and increased complexity. piRNAs have been identified in both vertebrates and invertebrates, and although biogenesis and modes of action do vary somewhat between species, a number of features are conserved. piRNAs have no clear secondary structure motifs, the length of a piRNA is between 26 and 31 nucleotides, and the bias for a 5' uridine is common to piRNAs in both vertebrates and invertebrates. piRNAs are found in clusters throughout the genome; these clusters may contain as few as ten or up to many thousands of piRNAs and can vary in size from one to one hundred kb.

RNA modification: The term "RNA modification" as used herein may refer to chemical modifications comprising backbone modifications as well as sugar modifications or base modifications.

In this context, a modified RNA molecule as defined herein may contain nucleotide analogues/modifications, e.g. backbone modifications, sugar modifications or base modifications. A backbone modification in connection with the present invention is a modification, in which phosphates of the backbone of the nucleotides contained in an RNA molecule as defined herein are chemically modified. A sugar modification in connection with the present invention is a chemical modification of the sugar of the nucleotides of the RNA molecule as defined herein. Furthermore, a base modification in connection with the present invention is a chemical modification of the base moiety of the nucleotides of the RNA molecule. In this context, nucleotide analogues or modifications are preferably selected from nucleotide analogues, which are applicable for transcription and/or translation.

Sugar Modifications: The modified nucleosides and nucleotides, which may be incorporated into a modified RNA molecule as described herein, can be modified in the sugar moiety. For example, the 2' hydroxyl group (OH) can be modified or replaced with a number of different "oxy" or "deoxy" substituents. Examples of "oxy"-2' hydroxyl group modifications include, but are not limited to, alkoxy or aryloxy (—OR, e.g., R=H, alkyl, cycloalkyl, aryl, aralkyl, heteroaryl or sugar); polyethyleneglycols (PEG), —O(CH$_2$CH$_2$O)nCH$_2$CH$_2$OR; "locked" nucleic acids (LNA) in which the 2' hydroxyl is connected, e.g., by a methylene bridge, to the 4' carbon of the same ribose sugar; and amino groups (—O-amino, wherein the amino group, e.g., NRR, can be alkylamino, dialkylamino, heterocyclyl, arylamino, diarylamino, heteroarylamino, or diheteroaryl amino, ethylene diamine, polyamino) or aminoalkoxy.

"Deoxy" modifications include hydrogen, amino (e.g. NH2; alkylamino, dialkylamino, heterocyclyl, arylamino, diaryl amino, heteroaryl amino, diheteroaryl amino, or amino acid); or the amino group can be attached to the sugar through a linker, wherein the linker comprises one or more of the atoms C, N, and O.

The sugar group can also contain one or more carbons that possess the opposite stereochemical configuration than that of the corresponding carbon in ribose. Thus, a modified RNA molecule can include nucleotides containing, for instance, arabinose as the sugar.

Backbone Modifications:

The phosphate backbone may further be modified in the modified nucleosides and nucleotides, which may be incorporated into a modified RNA molecule as described herein. The phosphate groups of the backbone can be modified by replacing one or more of the oxygen atoms with a different substituent. Further, the modified nucleosides and nucleotides can include the full replacement of an unmodified phosphate moiety with a modified phosphate as described herein. Examples of modified phosphate groups include, but are not limited to, phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulfur. The phosphate linker can also be modified by the replacement of a linking oxygen with nitrogen (bridged phosphoroamidates), sulfur (bridged phosphorothioates) and carbon (bridged methylene-phosphonates).

Base Modifications:

The modified nucleosides and nucleotides, which may be incorporated into a modified RNA molecule as described herein can further be modified in the nucleobase moiety. Examples of nucleobases found in RNA include, but are not limited to, adenine, guanine, cytosine and uracil. For example, the nucleosides and nucleotides described herein can be chemically modified on the major groove face. In some embodiments, the major groove chemical modifications can include an amino group, a thiol group, an alkyl group, or a halo group.

In particularly preferred embodiments of the present invention, the nucleotide analogues/modifications are selected from base modifications, which are preferably selected from 2-amino-6-chloropurineriboside-5'-triphosphate, 2-aminopurine-riboside-5'-triphosphate; 2-aminoadenosine-5'-triphosphate, 2'-amino-2'-deoxycytidine-triphosphate, 2-thiocytidine-5'-triphosphate, 2-thiouridine-5'-triphosphate, 2'-fluorothymidine-5'-triphosphate, 2'-O-methyl inosine-5'-triphosphate 4-thiouridine-5'-triphosphate, 5-aminoallylcytidine-5'-triphosphate, 5-aminoallyluridine-5'-triphosphate, 5-bromocytidine-5'-triphosphate, 5-bromouridine-5'-triphosphate, 5-bromo-T-deoxycytidine-5'-triphosphate, 5-bromo-T-deoxyuridine-5'-triphosphate, 5-iodocytidine-5'-triphosphate, 5-iodo-T-deoxycytidine-5'-triphosphate, 5-iodouridine-5'-triphosphate, 5-iodo-T-deoxyuridine-5'-triphosphate, 5-methylcytidine-5'-triphosphate, 5-methyluridine-5'-triphosphate, 5-propynyl-T-deoxycytidine-5'-triphosphate, 5-propynyl-2'-deoxyuridine-5'-triphosphate, 6-azacytidine-5'-triphosphate, 6-azauridine-5'-triphosphate, 6-chloropurineriboside-5'-triphosphate, 7-deazaadenosine-5'-triphosphate, 7-deazaguanosine-5'-triphosphate, 8-azaadenosine-5'-triphosphate, 8-azidoadenosine-5'-triphosphate, benzimidazole-riboside-5'-triphosphate, N1-methyladenosine-5'-triphosphate, N1-methylguanosine-5'-triphosphate, N6-methyladenosine-5'-triphosphate, O6-methylguanosine-5'-triphosphate, pseudouridine-5'-triphosphate, or puromycin-5'-triphosphate, xanthosine-5'-triphosphate. Particular preference is given to nucleotides for base modifications selected from the group of base-modified nucleotides consisting of 5-methylcytidine-5'-triphosphate, 7-deazaguanosine-5'-triphosphate, 5-bromocytidine-5'-triphosphate, and pseudouridine-5'-triphosphate.

In some embodiments, modified nucleosides include pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine.

In some embodiments, modified nucleosides include 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine.

In other embodiments, modified nucleosides include 2-aminopurine, 2, 6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine.

In other embodiments, modified nucleosides include inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methyl-inosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

In some embodiments, the nucleotide can be modified on the major groove face and can include replacing hydrogen on C-5 of uracil with a methyl group or a halo group.

In specific embodiments, a modified nucleoside is 5'-O-(1-thiophosphate)-adenosine, 5'-O-(1-thiophosphate)-cytidine, 5'-O-(1-thiophosphate)-guanosine, 5'-O-(1-thiophosphate)-uridine or 5'-O-(1-thiophosphate)-pseudouridine.

In further specific embodiments, a modified RNA may comprise nucleoside modifications selected from 6-aza-cytidine, 2-thio-cytidine, α-thio-cytidine, pseudo-iso-cytidine, 5-aminoallyluridine, 5-iodo-uridine, N1-methyl-pseudouridine, 5,6-dihydrouridine, α-thio-uridine, 4-thio-uridine, 6-aza-uridine, 5-hydroxy-uridine, deoxy-thymidine, 5-methyl-uridine, pyrrolo-cytidine, inosine, α-thio-guanosine, 6-methyl-guanosine, 5-methyl-cytdine, 8-oxo-guanosine, 7-deaza-guano sine, N1-methyl-adenosine, 2-amino-6-chloro-purine, N6-methyl-2-amino-purine, pseudo-iso-cytidine, 6-chloro-purine, N6-methyl-adenosine, α-thio-adenosine, 8-azido-adenosine, 7-deaza-adenosine.

Sequence Modifications:

The term "RNA modification" as used herein may further refer to an RNA which is modified in regards to the nucleotide sequence compared to the wild type sequence. Particularly if the RNA is a coding RNA, e.g. an mRNA the RNA may be sequence modified in the coding region (open reading frame). On the one hand, the G/C content of the region of the modified RNA coding for a peptide or polypeptide may be greater than the G/C content of the coding region of the wild-type RNA coding for the peptide or polypeptide, the coded amino acid sequence being unchanged relative to the wild-type. This modification is based on the fact that the sequence order of the RNA domain to be translated is essential for efficient RNA translation. In this respect, the composition and sequence of the various nucleotides has an important part to play. In particular, sequences with an elevated G(guanosine)/C(cytosine) content are more stable than sequences with an elevated A(adenosine)/U(uracil) content. Thus, according to the invention, while retaining the translated amino acid sequence, the codons are varied relative to the wild-type RNA in such a manner that they have a greater content of G/C nucleotides. Since several codons code for one and the same amino acid (degeneration of the genetic code), it is possible to determine the codons which are most favourable for stability (alternative codon usage). On the other hand it is also possible to provide a translation-optimised RNA by sequence modification.

Concentration: Concentration is a simple process that involves removing fluid from a solution while retaining the solute molecules. The concentration of the solute increases in direct proportion to the decrease in solution volume, i.e. halving the volume effectively doubles the concentration of the solute molecules.

Diafiltration: Diafiltration is the fractionation process that washes smaller molecules through a membrane and leaves larger molecules in the retentate without ultimately changing concentration. It can be used to remove salts or exchange buffers or solvents to deliver the product in the desired buffer or solvent. In the context of the present invention, diafiltration against water (WFI) and/or NaCl solution is performed in order to remove LMWC and HMWC (e.g. salts, short oligonucleotides, small proteins, spermidine and organic solvents). Diafiltration can be performed either discontinuously or alternatively, continuously. In continuous diafiltration, the diafiltration solution is added to the sample feed reservoir at the same rate as filtrate is generated. In this way, the volume in the sample reservoir remains constant but the small molecules (e.g. salts) that can freely permeate through the membrane are washed away. Using salt removal as an example, each additional diafiltration volume (DV) reduces the salt concentration further. In discontinuous diafiltration, the solution is first diluted and then concentrated back to the starting volume. This process is then repeated until the required concentration of small molecules (e.g. salts) remaining in the reservoir is reached. Each additional diafiltration volume (DV) reduces the salt concentration further. Continuous diafiltration requires less diafiltration volume to achieve the same degree of salt reduction as discontinuous diafiltration.

Diafiltration volume (DV): a single diafiltration volume is the volume of retentate when diafiltration is started.

deltaP (dp): Describes the pressure difference of the feed pressure (p1) and the retentate pressure (p2) in TFF. The value of dp is directly proportional to the flow rate over the membrane.

Feed pressure: The pressure measured at the inlet port of a cartridge/hollow fibre or cassette.

Feed flow rate: Volume of feed solution loaded on the filter membrane per given membrane area during a given time.

Transmembrane pressure (TMP): the driving force for liquid transport through the ultrafiltration membrane. Calculated as the average pressure applied to the membrane minus any filtrate pressure. In most cases, pressure at filtrate port equals zero.

Filtrate or Permeate: the portion of sample that has flowed through the membrane.

Flux: Flux represents the volume of solution flowing through a given membrane area during a given time. Expressed as LMH (liters per square meter per hour).

Permeate flux rate: permeate flow divided by the effective membrane area ($L/h/m^2$).

Permeate flow: flow rate of the permeate (L/h).

Membrane load: Amount of product (linearized plasmid DNA or in vitro transcribed RNA) per surface area of the filter membrane.

RNA integrity: The relative RNA integrity is preferably determined as the percentage of full-length RNA (i.e. non-degraded RNA) with respect to the total amount of RNA (i.e. full-length RNA and degraded RNA fragments (which appear as smears in gel electrophoresis)). RNA integrity can be measured and quantified by agrose gel electrophoresis (AGE) and/or analytical RP-HPLC.

Molecular Weight Cut Off (MWCO): The molecular weight cutoff of a membrane, sometimes called Nominal Molecular Weight Limit (NMWL), is defined by its ability to retain a given percentage of a globular solute of a defined molecular weight. Solute retention can however vary due to molecular shape, structure, solute concentration, presence of other solutes and ionic conditions.

DETAILED DESCRIPTION OF THE INVENTION

The present invention relates to methods for producing and purifying RNA, comprising the steps of
A) providing DNA encoding the RNA;
B) transcription of the DNA to yield a solution comprising transcribed RNA; and
C) conditioning and/or purifying of the solution comprising transcribed RNA by one or more steps of TFF.

The individual steps of the methods according to the present invention may be performed sequentially or they may at least partially overlap.

The RNA which is to be purified with the method according to the invention is a ribonucleic acid of any type, preferably as defined herein. The RNA is particularly preferably selected from mRNA, viral RNA, retroviral RNA and replicon RNA, small interfering RNA (siRNA), antisense RNA, clustered regularly interspaced short palindromic repeats (CRISPR) RNA, ribozymes, aptamers, riboswitches, immunostimulating RNA, transfer RNA (tRNA), ribosomal RNA (rRNA), small nuclear RNA (snRNA), small nucleolar RNA (snoRNA), microRNA (miRNA), and Piwi-interacting RNA (piRNA) or whole-cell RNA (total RNA extract). The RNA to be isolated may be single-stranded or double-stranded. Single-stranded RNA may optionally form secondary structures by refolding, the RNA to be separated typically being single-stranded. The RNA may be unlabelled or also labelled (with a fluorescent label or a radiolabel or an antibody epitope). One example of a labelled RNA is digoxigenin-labelled RNA. The RNA may also contain modifications (modified nucleotides), preferably as defined herein.

In a preferred embodiment of the method according to the invention, the RNA to be separated has a size of up to about 15000 nucleotides (as single stranded RNA molecule) or base pairs (as double stranded RNA molecule), in particular 100 to 10000, more preferably 500 to 10000 nucleotides or base pairs, even more preferably 500 to 7000 nucleotides or base pairs and even more preferably 500 to 5000 nucleotides or base pairs. For this size of RNA, it has proved possible to achieve very good results with regard to purification of the RNA, since the method according to the invention is particularly well suited to RNA of this size. Optionally, however, smaller RNA fragments, for example with a length of 30-500, 50-500 or 100-500 or 20-200, 20-100, 20-50 or 20-30 nucleotides may also be separated in this way.

If the RNA to be separated is a coding RNA, e.g. an mRNA, viral RNA or replicon RNA, it will preferably code for peptides or proteins. The RNA may encode a protein sequence or a fragment or variant thereof (e.g. fusion proteins), preferably selected from therapeutically active proteins or peptides, including adjuvant proteins, tumor antigens, cancer antigens, pathogenic antigens (e.g. selected, from animal antigens, from viral antigens, from protozoal antigens, from bacterial antigens), allergenic antigens, autoimmune antigens, or further antigens, allergens, antibodies, immunostimulatory proteins or peptides, antigen-specific T-cell receptors, biologicals, cell penetrating peptides, secreted proteins, plasma membrane proteins, cytoplasmic or cytoskeletal proteins, intracellular membrane bound proteins, nuclear proteins, proteins associated with human disease, targeting moieties or those proteins encoded by the human genome, for which no therapeutic indication has been identified but which nonetheless have utility in areas of research and discovery.

In a preferred embodiment, the RNA obtained according to the method of the present invention may be used as a pharmaceutical composition or may be a component of a pharmaceutical composition together with additional components.

The steps of the method according to the present invention will be described in the following in more detail.

Step A:

In a preferred embodiment, the DNA encoding the RNA provided in step A) may be any kind of DNA, including plasmid DNA, genomic DNA, or DNA fragments such as DNA-fragments obtained by polymerase chain reaction (PCR).

In a preferred embodiment, the DNA provided in step A) is plasmid DNA. The plasmid DNA may be provided in a circular form or in a linearized form. The linearized form is preferred and may be obtained, e.g. by digestion with a restriction enzyme (linearization). Preferred restriction enzymes are BciVI (BfuI), BcuI (SpeI), EcoRI, AatII, AgeI (BshTI), ApaI, BamHI, BglII, BlpI (Bpu1102I), BsrGI (Bsp1407), ClaI (Bsu15I), EcoRI, EcoRV (Eco32I), HindIII, KpnI, MluI, NcoI, NdeI, NheI, NotI, NsiI, Mph1103I, PstI, PvuI, PvuII, SacI, SalI, ScaI, SpeI, XbaI, XhoI, SacII (Cfr42I), XbaI. The skilled artisan knows under what conditions the linearization of the DNA may be performed and that the linearization conditions are dependent on which kind of restriction enzyme is used. In one embodiment, the plasmid DNA may be conditioned or purified by using one or more steps of TFF prior to linearization.

The at least one step of TFF may comprise at least one diafiltration step and/or at least one concentration step. The diafiltration and concentration step may be performed separately but they may also at least partially overlap. The at least one or more steps of TFF may efficiently remove contaminants, such as HMWC and LMWC, e.g. DNA fragments, organic solvents, buffer components such as salts and detergents. The use of TFF may thus reduce or abolish the need to purify the DNA by means of organic solvent extraction such as phenol/chloroform extraction and/or alcohol precipitation of nucleic acids such as RNA and DNA, e.g. by high salt/alcohol precipitation such as NaCl/isopropanol precipitation. Further, it was found that, surprisingly, the use of TFF does not negatively affect the stability of the DNA, e.g. due to shear stress during pumping.

In preferred embodiments the one or more steps of TFF prior linearization is performed as described for step A3) conditioning, and/or purifying of the linearized DNA by one or more steps of TFF.

In a preferred embodiment, the linearization reaction comprises:
1 μg plasmid DNA;
0.5 μl reaction buffer;
3 Units restriction enzyme;
Add. 5 μl with WFI (water for injection).

The reaction is preferably incubated for 4 to 5 hour at 37° C.

In a further preferred embodiment which is useful for large-scale production, the linearization reaction comprises:
30 mg plasmid DNA;
15 ml reaction buffer (10× restriction buffer)
9 ml restriction enzyme [10 U/μl]
The reaction is filled up to a final volume of 150 ml using WFI and incubated for 4 to 5 hour at 37° C.

In a preferred embodiment, the linearization reaction, e.g. the linearization reaction using a restriction enzyme, may be terminated. The termination of the linearization may be performed by adding an agent that inhibits the activity of the restriction enzyme. In one embodiment, the termination of linearization may be performed by adding an effective amount of ethylenediaminetetraacetic acid (EDTA). In another preferred embodiment the restriction enzyme is inactivated by heat inactivation e.g. by incubation at 65° C.

In one embodiment, the plasmid DNA comprises at least one terminator sequence. This sequence mediates transcriptional termination by providing signals in the newly synthesized RNA that trigger processes which release the RNA from the transcriptional complex.

In a preferred embodiment, one or more steps of TFF are performed after the linearization reaction. The one or more steps of TFF may either be performed as a diafiltration step for i) exchange the solvent of the linearized DNA to conditions required for the transcription and/or for ii) purifying the linearized DNA; and/or as a concentration step for concentrating the linearized DNA. The conditioning may be performed by at least one step of diafiltration using TFF to a diafiltration solution or buffer.

In a preferred embodiment of the method according to the present invention, the DNA provided in step A) is plasmid DNA as the DNA encoding the RNA and the method comprises subsequently to step A) the above described steps:
A1) linearization of the plasmid DNA in a linearization reaction;
A2) optionally termination of the linearization reaction; and
A3) conditioning and/or purifying of the linearization reaction comprising linearized plasmid DNA by one or more steps of TFF.

Step A3 according to the present invention comprises conditioning, and/or purifying of the linearization reaction comprising linearized plasmid DNA by one or more steps of TFF. The at least one step of TFF may comprise at least one diafiltration step using TFF and/or at least one concentration step using TFF. The diafiltration and concentration step may be performed separately but they may also at least partially overlap. The at least one or more steps of TFF may efficiently remove contaminants, such as HMWC and LMWC, e.g. DNA fragments, organic solvents, buffer components such as salts and detergents. The use of TFF may thus reduce or abolish the need to purify the DNA by means of organic solvent extraction such as phenol/chloroform extraction and/or alcohol precipitation of nucleic acids such as RNA and DNA, e.g. by high salt/alcohol precipitation such as NaCl/isopropanol precipitation. Further, it was found that, surprisingly, the use of TFF does not negatively affect the stability of the DNA, e.g. due to shear stress during pumping.

Thus, in a preferred embodiment, the method according to the present invention in step A3, particularly during conditioning, and/or purifying of the linearization reaction does not comprise a step of phenol/chloroform extraction and/or DNA/and/or RNA precipitation.

In a preferred embodiment, the at least one step of TFF in step A3 comprises at least one concentration step. In this context it is particularly preferred to concentrate the linearization reaction to at least 90%, 80%, 70%, 60%, 50%, 40%, 30% or to at least 13% of the original volume.

In a preferred embodiment, the at least one step of TFF in step A3 comprises at least one concentration step, wherein the linearized plasmid DNA is concentrated from an initial concentration of about 0.05 g/l, 0.1 g/l, 0.15 g/l, 0.2 g/l, 0.25 g/l or 0.3 g/l linearized plasmid DNA to a final concentration of about 0.8 g/l, 0.9 g/l, 1.0 g/l, 1.1 g/l, 1.2 g/l, 1.3 g/l, 1.4 g/l or about 1.5 g/l linearized plasmid DNA.

In another preferred embodiment, the at least one step of TFF in step A3 comprises at least one concentration step, wherein the linearization reaction is concentrated from 0.2 g/l DNA to 1.0 g/l or 1.5 g/l DNA.

In a further preferred embodiment, the at least one step of TFF in step A3 comprises at least one diafiltration step.

In a preferred embodiment, the diafiltration step is performed with water or an aqueous salt solution as diafiltration solution. Particularly preferred is a diafiltration step with water.

In a preferred embodiment, the at least one step of TFF in step A3 is performed using from about 1 to about 20 diafiltration volumes (DV) diafiltration solution or buffer, preferably from about 1 to about 15 DV diafiltration solution or buffer and more preferably from about 5 to about 12 DV diafiltration solution or buffer and even more preferably from about 6 to about 10 DV diafiltration solution or buffer. In a particularly preferred embodiment, the at least one step of TFF is performed using about 10 DV diafiltration solution or buffer, particularly water.

According to a particularly preferred embodiment, the at least one step of TFF in step A3 comprises at least one concentration step and at least one diafiltration step. Preferably, the at least one diafiltration step is performed after the concentration step of step A3.

TFF may be carried out using any suitable filter membrane. For example, TFF may be carried out using a TFF hollow fibre membrane or a TFF membrane cassette. The use of a TFF membrane cassette is preferred. The molecular weight cutoff of the filter membrane may be selected depending on the size of the DNA, particularly the plasmid DNA. The larger the DNA molecule of interest, the higher the molecular weight cutoff of the membrane may be selected. In a preferred embodiment, the molecular weight cutoff of the filter membrane is 500 kDa, more preferably 200 kDa and most preferably 100 kDa. The filter membrane may comprise any suitable filter material, e.g. polyethersulfone (PES), modified polyethersulfone (mPES), polysulfone (PS), modified polysulfone (mPS), ceramics, polypropylene (PP), cellulose, regenerated cellulose or a cellulose derivative e.g. cellulose acetate or combinations thereof.

Particularly preferred in this context is a cellulose-based membrane (cellulose, regenerated cellulose or a cellulose derivative) or a PES or mPES-based filter membrane, particularly with a MWCO of 100 kDa.

In a preferred embodiment, the DNA membrane load of the TFF membrane is about 0.1 to about 10 mg/cm$^2$ and preferably from about 0.5 to about 2 mg/cm$^2$.

In a preferred embodiment, the DNA membrane load of the TFF membrane is about 0.1 to 0.6 mg/cm$^2$.

The feed flow rate in the at least one step of TFF in step A3 is 500 to 1.500 l/h/m$^2$, preferably 600 to 1.200 l/h/m$^2$, more preferably 700 to 1.000 l/h/m$^2$ and most preferably 750 to 900 l/h/m$^2$.

In a preferred embodiment, a TFF membrane cassette is used in step A3 for the at least one TFF step. Surprisingly, it was found that TFF membrane cassettes are particularly suitable for the method according to the present invention. Examples of TFF membrane cassettes are Sartocon Slice 200 100 kDa, PES (Sartorius), Sartcocon Slice 200 300 kDa, PES (Sartorius), Omega Centramate T 05300T02, PES 300 kDa (PALL), Omega Centramate T OS100T02, PES 100 kDa (PALL) or NovaSet-LS ProStream (Low Binding mPES), 100 kDa (NovaSep). Another example is Sartocon Slice 200 100 kDa, Hydrosart (Sartorius), which is a stabilised cellulose-based membrane, i.e. a cellulose derivative membrane.

Particularly preferred in this context is a TFF membrane cassette comprising a cellulose-based membrane or a PES or mPES-based filter membrane with a MWCO of 100 kDa.

Particularly preferred in this context is a TFF membrane cassette comprising a mPES-based filter membrane with a MWCO of 100 kDa, e.g., a commercially available TFF membrane cassette such as NovaSep mPES with a MWCO of 100 kDa, or a cellulose-based membrane cassette with a MWCO of 100 kDa, e.g. a commercially available TFF membrane cassette such as Hydrosart (Sartorius).

Using TFF membrane cassettes provides the possibilities of higher permeate flux rates compared to using hollow fibre membranes. A higher permeate flux rate of the TFF step may result in a faster process time and consequently lower production costs.

In a preferred embodiment of the present invention, the at least one step of TFF in step A3 provides a permeate flux rate of at least 30 l/h/m$^2$, 50 l/h/m$^2$, 70 l/h/m$^2$ or 90 l/h/m$^2$, preferably at least 100 l/h/m$^2$, more preferably at least 110 l/h/m$^2$ and even more preferably at least 120 l/h/m$^2$. Also preferably, the at least one step of TFF in step A3 provides a permeate flux rate of 30 l/h/m$^2$ to 100 l/h/m$^2$.

In another preferred embodiment, the transmembrane pressure (TMP) over the TFF membrane cassette in this step is from about 0.01 (0.1 bar) to about 0.3 MPa (3 bar) and preferably from about 0.1 (1 bar) to about 0.2 MPa (2 bar) and most preferably is 0.1 MPa (1 bar). Furthermore, a deltaP (dp) of from about 0.05 (0.5 bar) to about 0.5 MPa (5 bar) and particularly of about 0.1 MPa (1 bar) is preferred. The values for TMP and dp of about 0.1 MPa (1 bar) and about 0.1 MPa (1 bar), respectively, are particularly preferred because under these conditions the process is not cake layer driven.

In a preferred embodiment, at least one or more steps of TFF in step A3 comprise using a TFF membrane cassette comprising a cellulose or cellulose derivative-based membrane. In a preferred embodiment, both the concentration and the diafiltration step of TFF in step A3 comprises using a TFF membrane cassette comprising a cellulose or cellulose derivative-based membrane. A Hydrosart membrane (Sartorius), which provides high permeate flux rates and at the same time a high stability in the presence of organic solvents such as acetonitrile, is particularly preferred.

In another preferred embodiment, at least one or more steps of TFF in step A3 comprise using a TFF PES- or mPES-based membrane cassette, e.g. a PES-based membrane from Sartorius, more preferably a mPES-based membrane cassette from NovaSep.

In yet another preferred embodiment, the at least one or more steps of TFF in step A3 comprises using a TFF membrane with a molecular weight cutoff of about 100 kDa.

In yet another preferred embodiment, the at least one or more steps of TFF in step A3 comprises using a TFF membrane with a molecular weight cutoff of about 300 kDa.

Step B:

In step B of the method according to the present invention the DNA (template) may either be transcribed in vivo or in vitro to yield a solution comprising RNA.

In a preferred embodiment, the DNA template is transcribed in vitro to yield a solution comprising RNA in a process called DNA dependent RNA in vitro transcription. The DNA dependent RNA in vitro transcription may be performed in the presence of an in vitro transcription mix (IVT-mix). The IVT-mix is a complex mixture of several high and low molecular weight compounds (HMWC/LMWC), e.g. linear template DNA, nucleoside triphosphates (NTPs), proteins, e.g. proteins of the transcription machinery and/or enzymes, spermidine and salts.

In general, RNA can be produced "in vitro" from a PCR-based DNA template, or a plasmid DNA-based linearized DNA template using DNA dependent RNA polymerases.

Particularly preferred is DNA dependent RNA in vitro transcription using a linearized plasmid DNA template.

The template DNA, preferably the linearized template DNA plasmid is transcribed into RNA using DNA dependent RNA in vitro transcription. That reaction typically comprises a transcription buffer, nucleotide triphosphates (NTPs), an RNase inhibitor and a DNA-dependent RNA polymerase. The NTPs can be selected from, but are not limited to those described herein including naturally occurring and non-naturally occurring (modified) NTPs. The DNA-dependent RNA polymerase can be selected from, but is not limited to, T7 RNA polymerase, T3 RNA polymerase, SP6 RNA polymerase and mutant polymerases such as, but not limited to, polymerases able to incorporate modified NTPs.

In preferred embodiments, viral DNA-dependent RNA polymerases is used as the RNA polymerase. More preferably, a bacteriophage DNA-dependent RNA polymerase selected from the group comprising T3, T7 and/or Sp6 polymerases is used as the RNA polymeraseMost preferably T7 RNA polymerase is used as an enzyme for DNA-dependent RNA in vitro transcription.

In a preferred embodiment, 1-1000 Units (U DNA-dependent RNA polymerase per µg DNA template may be used. Even more preferred is a concentration of 100 U/DNA-dependent RNA polymerase per µg DNA template During RNA polymerization, the RNA may be co-transcriptionally capped at the 5' end with a cap analogue as defined herein (e.g. N7-MeGpppG).

As transcription buffer following buffers are preferred: 40 mM Tris pH 7.5 or 80 mM HEPES. 80 mM HEPES is particularly preferred.

In another preferred embodiment, 40 mM Tris-HCl buffer pH 7.5 is preferred.

In a preferred embodiment, a template DNA concentration of from about 10 to about 500 µg/ml is used. Particularly preferred is a template DNA concentration of about 50 µg/ml.

For the transcription, nucleotide triphosphates of the desired chemistry are used, including naturally occurring nucleotides (e.g. at least one of the nucleotides ATP, CTP, UTP and GTP) and/or modified nucleotides, preferably modified nucleotides as described herein, or any combination thereof.

ATP, CTP, UTP and GTP are preferably used in a concentration of 0.5-10 mM, preferably in a concentration of 3-5 mM and most preferably in a concentration of 4 mM.

Useful cap analogs include, but are not limited to, N7-MeGpppG (=m7G(5')ppp(5')G), m7G(5')ppp(5')A, ARCA (anti-reverse CAP analogue, modified ARCA (e.g. phosphothioate modified ARCA), inosine, N1-methyl-guanosine, 2'-fluoro-guanosine, 7-deaza-guanosine, 8-oxo-guanosine, 2-amino-guanosine, LNA-guanosine, and 2-azido-guanosine. If 5'-CAP (cap analog) is used, the concentration of GTP is decreased compared to the other used nucleotides. Preferably 10 to 50% of GTP is used compared to the concentration of ATP, CTP and UTP. Most preferably 20-30% of GTP is used.

Furthermore, the cap analog is preferably used in a concentration which is at least the same as the concentration of ATP, CTP and UTP.

The ratio of cap analog:nucleotide and preferably cap analog:GTP can be varied from 10:1 to 1:1 to balance the percentage of capped products with the efficiency of the transcription reaction, preferably a ratio of cap analog:GTP of 4:1-5:1 is used. In this context, it is particularly preferred to use 5.8 mM Cap analog and 1.45 mM GTP if ATP, UTP and CTP are used in a concentration of 4 mM.

$MgCl_2$ can optionally be added to the transcription reaction. Preferred is a concentration of 1-100 mM. Particularly preferred is a concentration of 5-30 mM and most preferably 24 mM $MgCl_2$ is used.

Dithiothreitol (DTT) can optionally be added to the transcription reaction, preferably at a concentration of 1-100 mM, more preferably 10-100 mM, and most preferably 40 mM.

An RNase inhibitor can optionally be added to the transcription reaction, preferably 0.1-1 U/µl, most preferably 0.2 U/µl.

*E. coli* pyrophosphatase can optionally be added to the transcription reaction, preferably in a concentration of 1-10 U/µg template DNA, and more preferably in a concentration of 5 U/µg template DNA. This ensures that magnesium, which is essential for transcription, remains in solution and does not precipitate as magnesium pyrophosphate.

Bovine serum albumine (BSA) can optionally be used in the transcription reaction, preferably in a concentration of 1-1000 µg/ml, more preferably in a concentration of 100 µg/ml. Most preferably, BSA is not present in the transcription reaction.

In a particularly preferred embodiment, the IVT-mix comprises polycationic aliphatic amines, preferably spermidine. The polycationic aliphatic amines may interact with the negatively charged nucleic acids. The presence of the polycationic aliphatic amine, preferably spermidine, is known to assist the RNA in vitro transcription process. However, residual spermidine has to be depleted from the RNA solution, particularly if the RNA is used for therapeutic purposes.

In the light of the above, there is therefore a need to remove spermidine from the solution of the in vitro transcribed RNA in subsequent purification steps.

In a preferred embodiment, the IVT-mix comprises from about 0.1 mM to about 10 mM spermidine, preferably from about 1 mM to about 5 mM, and most preferably about 2 mM spermidine.

In a particularly preferred embodiment, the RNA in vitro transcription reaction comprises the following components:
 1 µg linearized plasmid DNA,
 4 mM ATP, CTP and UTP,
 1.45 mM GTP,
 5.8 mM CAP analogue,
 80 mM HEPES,
 24 mM $MgCl_2$,
 2 mM Spermidine,
 40 mM DTT,
 5 U pyrophosphatase,
 4 U RNase inhibitor, and
 100 U T7 RNA polymerase.

The in vitro transcription reaction may be incubated at 37° C. preferably for at least 4 hours.

In another particularly preferred embodiment, the RNA in vitro transcription for large-scale reactions comprises the following components:
 25 mg linearized plasmid DNA,
 20 mM ATP, CTP and UTP,
 7.25 mM GTP,
 29 mM CAP analogue,
 80 mM HEPES,
 24 mM $MgCl_2$,
 2 mM Spermidine,
 40 mM DTT, and
 the enzymes pyrophosphatase (5 U per µg DNA), RNAse inhibitor (0.2 U/µl) and T7 RNA Polymerase (100 U per µg DNA).

The RNA in vitro transcription reaction may be incubated at 37° C., preferably for at least 4 hours.

After RNA in vitro transcription of the DNA, the transcribed RNA is present in a solution. The solution typically comprises components of the IVT-mix, which typically still comprise proteins such as polymerase and other enzymes, BSA, HEPES, pyrophosphatase etc, nucleotides, salts and spermidine.

Step C:

Step C according to the present invention comprises conditioning and/or purifying of the solution comprising transcribed RNA by one or more steps of TFF. The at least one step of TFF may comprise at least one diafiltration step and/or at least one concentration step. The diafiltration and concentration steps may be performed separately, but they may also at least partially overlap. The at least one or more steps of TFF may efficiently remove contaminants, such as HMWC and LMWC, e.g. RNA fragments; DNA fragments, proteins, organic solvents, nucleoside triphosphates, spermidine and buffer components such as salts and detergents. The use of TFF may thus reduce or abolish the need to purify the RNA by means of organic solvent extraction such as phenol/chloroform extraction and/or alcohol precipitation of nucleic acids such as RNA and DNA, e.g. by high salt/alcohol precipitation such as NaCl/isopropanol precipitation. Further, it was found that, surprisingly, the use of TFF does not negatively affect the stability of the RNA, e.g. due to shear stress during pumping.

Thus, in a preferred embodiment, the method according to the present invention does not comprise a step of phenol/chloroform extraction and/or DNA and/or RNA precipitation. It is one advantage of the method according to the present invention that the purified RNA may provide increased storage stability after at least one step of TFF compared e.g. to the storage stability of the RNA in the IVT-mix.

Further, the method according to the present invention does not comprise the addition of a protein denaturing agent such as urea, guanidinium thiocyanate, KCl, sodium dodecyl sulfate, sarcosyl or other detergents to the RNA in vitro transcription reaction mixture, before it is subjected to tangential flow filtration.

In a preferred embodiment, the at least one step of TFF in step C comprises at least one diafiltration step.

The TFF step in step C2 is preferably a diafiltration step which is preferably performed with water.

In a preferred embodiment, the at least one step of TFF in step C2 is performed using from about 1 to about 20 diafiltration volumes (DV) diafiltration solution or buffer, preferably from about 1 to about 15 DV diafiltration solution or buffer and more preferably from about 5 to about 12 DV diafiltration solution or buffer and even more preferably from about 5 to about 10 DV diafiltration solution or buffer. In a particularly preferred embodiment, the at least one step of TFF is performed using about 10 DV diafiltration solution or buffer.

In a preferred embodiment, the diafiltration step is performed with water or an aqueous salt solution as diafiltration solution or buffer. In a preferred embodiment, the salt of the aqueous salt solution may comprise alkaline metal halides such as NaCl, LiCl or KCl; organic salts such as NaOAc, earth alkaline metal halides such as $CaCl_2$; alkaline metal phosphates such as $Na_3PO_4$, $Na_2HPO_4$, $NaH_2PO_4$; or combinations thereof.

In a more preferred embodiment, the salt of the aqueous salt solution comprises alkaline metal halides such as NaCl, LiCl or KCl; earth alkaline metal halides such as $CaCl_2$ or combinations thereof.

In a more preferred embodiment, the aqueous salt solution comprises from about 0.1 M alkaline metal halide to about 1 M alkaline metal halide, more preferably from about 0.2 to about 0.5 M alkaline metal halide. Concentrations higher than the preferred range may lead to RNA precipitation and, consequently, blocking of the TFF membrane.

In another preferred embodiment, the aqueous salt solution comprises NaCl. In a more preferred embodiment, the aqueous salt solution comprises from about 0.1 M NaCl to about 1 M NaCl, more preferably from about 0.2 to about 0.5 M NaCl.

In another preferred embodiment, the diafiltration solution does not comprise buffering salts.

In another preferred embodiment, the diafiltration solution is water, preferably distilled and sterile water, more preferably water for injection.

In a preferred embodiment, the at least one step of TFF is performed using from about 1 to about 20 diafiltration volumes (DV) diafiltration solution or buffer, preferably from about 1 to about 15 DV diafiltration solution or buffer and more preferably from about 5 to about 12 DV diafiltration solution or buffer and even more preferably from about 5 to about 10 DV diafiltration solution or buffer. In a particularly preferred embodiment, the at least one step of TFF is performed using about 10 DV diafiltration solution or buffer.

All TFF steps in step C may be carried out using any suitable filter membrane. For example, TFF may be carried out using a TFF hollow fibre membrane or a TFF membrane cassette. The use of a TFF membrane cassette is preferred. The molecular weight cutoff of the filter membrane may be selected depending on the size of the produced desired RNA molecules. The larger the RNA molecule of interest, the higher the molecular weight cutoff of the membrane may be selected, respectively. In a preferred embodiment, the molecular weight cutoff of the filter membrane is 500 kDa, more preferably 200 kDa and most preferably 100 kDa. The filter membrane may comprise any suitable filter material, e.g. polyethersulfone (PES), modified polyethersulfone (mPES), polysulfone (PS), modified polysulfone (mPS), ceramics, polypropylene (PP), cellulose, regenerated cellulose or a cellulose derivative e.g. cellulose acetate or combinations thereof. Particularly preferred in this context is a cellulose-based membrane (cellulose, regenerated cellulose or a cellulose derivative), a PES or mPES-based filter membrane, particularly with a MWCO of 100 kDa.

In a preferred embodiment, the RNA membrane load of the TFF membrane is about 1 to about 10 $mg/cm^2$ and preferably from about 2 to about 6 $mg/cm^2$.

In a particularly preferred embodiment, the RNA membrane load of the TFF membrane in step C2 is about 2.5 to about 6.5 $mg/cm^2$.

The feed flow rate in the at least one step of TFF in step C2 is 100 to 1.500 $l/h/m^2$, preferably 150 to 1.300 $l/h/m^2$, more preferably 200 to 1.100 $l/h/m^2$ and most preferably 300 to 1.050 $l/h/m^2$.

In a preferred embodiment, a TFF membrane cassette is used. Surprisingly, it was found that TFF membrane cassettes are particularly suitable for the method according to the present invention. Examples of TFF membrane cassettes are Sartocon Slice 200 100 kDa, PES (Sartorius), Sartcocon Slice 200 300 kDa, PES (Sartorius), Omega Centramate T 05300T02, PES 300 kDa (PALL), Omega Centramate T OS100T02, PES 100 kDa (PALL) or NovaSet-LS ProStream (Low Binding mPES), 100 kDa (NovaSep). Another example is Sartocon Slice 200 100 kDa, Hydrosart (Sartorius), which is a stabilised cellulose-based membrane, i.e. a cellulose derivative membrane.

Particularly preferred in this context is a TFF membrane cassette comprising an mPES-based filter membrane with a MWCO of 100 kDa, e.g., a commercially available TFF membrane cassette such as NovaSep mPES with a MWCO of 100 kDa, or a cellulose-based membrane cassette with a MWCO of 100 kDa, e.g. a commercially available TFF membrane cassette such as Hydrosart (Sartorius).

Using TFF membrane cassettes provides the possibilities of higher permeate flux rates compared to using hollow fibre membranes. A higher permeate flux rate of the TFF step may result in a higher concentration of the retentate and thus a more concentrated RNA product and a faster process time and consequently lower production costs.

In a preferred embodiment of the present invention, the at least one step of TFF in step C2 provides a permeate flux rate of at least 20 $l/h/m^2$, 40 $l/h/m^2$, 60 $l/h/m^2$, 80 $l/h/m^2$ or 90 $l/h/m^2$, preferably at least 100 $l/h/m^2$, more preferably at least 110 $l/h/m^2$ and even more preferably at least 120 $l/h/m^2$. Also preferably, the at least one step of TFF in step A3 provides a permeate flux rate of 20 $l/h/m^2$ to 100 $l/h/m^2$.

In another preferred embodiment, the transmembrane pressure (TMP) over the TFF membrane cassette in step C2 is from about 0.01 (0.1 bar) to about 0.3 MPa (3 bar) and preferably from about 0.05 (0.5 bar) to about 0.2 MPa (2 bar) and most preferably from about 0.075 (0.75 bar) to about 0.15 MPa (1.5 bar) or from about 0.1 MPa (1 bar) to about 0.15 MPa (1.5 bar). Furthermore, a deltaP (dp) of from about 0.05 (0.5 bar) to about 0.5 MPa (5 bar), more preferably of from about 0.05 (0.5 bar) to about 0.1 MPa (1 bar) and particularly of about 0.1 MPa (1 bar) is preferred. The values for TMP and dp of about 0.15 MPa (1.5 bar) and about 0.1 Mpa (1 bar), respectively, are particularly preferred because under these conditions the process is not cake layer driven.

In a preferred embodiment, the values for TMP are from about 0.1 to about 0.15 and dp are about 0.1 MPa.

In a preferred embodiment, at least one or more steps of TFF comprise using a TFF membrane cassette comprising a cellulose-based membrane. A Hydrosart membrane (Sartorius), and a NovaSep membrane which provide high permeate flux rates and at the same time a high stability in the presence of organic solvents such as acetonitrile, is particularly preferred.

In another preferred embodiment, at least one or more steps of TFF comprise using a TFF PES- or mPES-based membrane cassette e.g. a PES-based membrane more preferably an mPES-based membrane cassette from NovaSep.

In yet another preferred embodiment, the at least one or more steps of TFF comprises using a TFF membrane with a molecular weight cutoff of about 100 kDa.

In yet another preferred embodiment, the at least one or more steps of TFF comprises using a TFF membrane with a molecular weight cutoff of about 50 kDa.

In one embodiment of the inventive method, the same TFF membrane cassette is used for more than one or even all TFF steps. The use of the same TFF membrane for more than one TFF steps is particularly advantageous because it reduces the amount of disposable waste, costs and time of the inventive RNA production method.

In one preferred embodiment, the method according to the present invention does not comprise using a TFF hollow fibre membrane in any of the TFF steps.

In yet another preferred embodiment, the step C) of the inventive method comprises at least one further purification method C3 before or after the one or more steps of TFF. In a preferred embodiment, the further purification method is performed after a first TFF step C2 and before a second TFF step C4. In a preferred embodiment, the at least one further purification method is selected from the group consisting of cation exchange chromatography, anion exchange chromatography, membrane absorbers, reversed phase chromatography, normal phase chromatography, size exclusion chromatography, hydrophobic interaction chromatography, mixed mode chromatography, affinity chromatography, hydroxylapatite (HA) chromatography, or combinations thereof. In another embodiment the at least one further purification method does not comprise any of hydroxyapatite chromatography and core bead flow-through chromatography.

In a preferred embodiment, the at least one further purification method is performed before the at least one step of TFF.

In a further preferred embodiment the at least one further purification method is performed by means of high performance liquid chromatography (HPLC) or low normal pressure liquid chromatography methods. A HPLC method is particularly preferred.

In another preferred embodiment, the at least one further purification method is a reversed phase chromatography method, preferably a reversed phase HPLC (RP-HPLC) method. Preferably, the reversed phase chromatography comprises using a porous reserved phase as stationary phase.

In a preferred embodiment of the method according to the invention, the porous reversed phase material is provided with a particle size of 8.0 μm to 50 μm, in particular 8.0 to 30 μm, still more preferably about 30 μm. The reversed phase material may be present in the form of small spheres. The method according to the invention may be performed particularly favourably with a porous reversed phase with this particle size, optionally in bead form, wherein particularly good separation results are obtained.

In another preferred embodiment, the reversed phase used in the method according to the invention may be porous and may have specific particle sizes. With stationary reversed phases which are not porous and thus differ completely with regard to particle size from the subject matter of the present invention as described for example by A. Azarani and K. H. Hecker (Nucleic Acids Research, vol. 29, no. 2 e7), on the other hand, excessively high pressures are built up, such that preparative purification of the RNA is possible only with great difficulty, if at all.

In a preferred embodiment of the method according to the invention, the reversed phase has a pore size of 1000 Å to 5000 Å, in particular a pore size of 1000 Å to 4000 Å, more preferably 1500 Å to 4000 Å, 2000 Å to 4000 Å or 2500 Å to 4000 Å. Particularly preferred pore sizes for the reversed phases are 1000 Å to 2000 Å, more preferably 1000 Å to 1500 Å and most preferably 1000 Å to 1200 Å or 3500-4500 Å. Most preferred is a pore size of 4000 Å. With a reversed phase having these pore sizes, particularly good results are achieved with regard to purification of the RNA using the method according to the invention, in particular the elevated pressures built up in the method according to A. Azarani and K. H. Hecker are thus avoided, whereby preparative separation is made possible in a particularly favourable manner. At pore sizes of below 1000 Å separation of RNA molecules becomes poorer.

A pore size of 1000 Å to 5000 Å, in particular a pore size of 1000 Å to 4000 Å, more preferably 1500 Å to 4000 Å, 2000 Å to 4000 Å or 2500 Å to 4000 Å may be suitable to separate a RNA from other components of a mixture, the RNA having a size as mentioned above of up to about 15000 nucleotides (as single stranded RNA molecule) or base pairs (as double stranded RNA molecule), in particular 100 to 10000, more preferably 500 to 10000 nucleotides or base pairs, even more preferably 800 to 5000 nucleotides or base pairs and even more preferably 800 to 2000 nucleotides or base pairs. However, the pore size of the reversed phase may also be selected in dependence of the size of the RNA to be separated, i.e. a larger pore size may be selected, if larger RNA molecules are to be separated and smaller pore sizes may be selected, if smaller RNA molecules may be selected.

This is due to the effect that the retention of the RNA molecules and the separation not only depends on the interaction of the (reversed) phase but also on the possibility of molecules to get inside the pores of the matrix and thus provide a further retention effect. Without being limited thereto, e.g. a pore size for the reversed phase of about 2000 Å to about 5000 Å, more preferably of about 2500 to about 4000, most preferably of about 3500 to about 4500 Å, may thus be used to separate larger RNA molecules, e.g. RNA molecules of 100 to 10000, more preferably 500 to 10000 nucleotides or base pairs, even more preferably 800 to 5000 nucleotides or base pairs and even more preferably 800 to 2000 nucleotides or base pairs. Alternatively, without being limited thereto, a pore size for the reversed phases of about 1000 Å to about 2500 Å, more preferably of about 1000 Å to about 2000 Å, and most preferably of about 1000 Å to 1200 Å may be used to separate smaller RNA molecules, e.g. RNA molecules of about 30-1000, 50-1000 or 100-1000 or 20-200, 20-100, 20-50 or 20-30 nucleotides may also be separated in this way.

In general, any material known to be used as reverse phase stationary phase, in particular any polymeric material may be used for the inventive method, if that material can be provided in porous form. The stationary phase may be composed of organic and/or inorganic material. Examples for polymers to be used for the present invention are (non-alkylated) polystyrenes, (non-alkylated) polystyrenedivinylbenzenes, monolithic materials, silica gel, silica gel modified with non-polar residues, particularly silica gel modified with alkyl containing residues, more preferably with butyl-, octyl and/or octadecyl containing residues, silica gel modified with phenylic residues, polymethacrylates, etc. or other materials suitable e.g. for gel chromatography or other chromatographic methods as mentioned above, such as dextran, including e.g. Sephadex® and Sephacryl® materials, agarose, dextran/agarose mixtures, polyacrylamide, etc.

In a particularly preferred embodiment, the material for the reversed phase is a porous polystyrene polymer, a (non-alkylated) (porous) polystyrenedivinylbenzene polymer, porous silica gel, porous silica gel modified with non-polar residues, particularly porous silica gel modified with alkyl containing residues, more preferably with butyl-, octyl and/or octadecyl containing residues, porous silica gel modified with phenylic residues, porous polymethacrylates, wherein in particular a porous polystyrene polymer or a non-alkylated (porous) polystyrenedivinylbenzene may be used. Stationary phases with polystyrenedivinylbenzene are known per se. The per se known polystyrenedivinyl-benzenes already used for HPLC methods, which are commercially obtainable, may be used for the method according to the invention.

A non-alkylated porous polystyrenedivinylbenzene which is very particularly preferred for the method according to the invention is one which, without being limited thereto, may have in particular a particle size of 8.0±1.5 μm, in particular 8.0±0.5 μm, and a pore size of 1000-1500 Å, in particular 1000-1200 Å or 3500-4500 Å and most preferably a particle size of 4000 Å. With this material for the reversed phases, the above-described advantages of the method according to the invention may be achieved in a particularly favourable manner.

This stationary phase described in greater detail above is conventionally located in a column. V2A steel is conventionally used as the material for the column, but other materials may also be used for the column provided they are suitable for the conditions prevailing during HPLC. Conventionally the column is straight. It is favourable for the HPLC column to have a length of 5 cm to 100 cm and a diameter of 4 mm to 50 cm. Columns used for the method according to the invention may in particular have the following dimensions: 25 cm long and 20 mm in diameter or 25 cm long and 50 mm in diameter, or 25 cm long and 10 cm in diameter or any other dimension with regard to length and diameter, which is suitable for preparative recovery of RNA, even lengths of several metres and also larger diameters being feasible in the case of upscaling. The dimensions are here geared towards what is technically possible with liquid chromatography.

Selection of the mobile phase depends on the type of separation desired. This means that the mobile phase established for a specific separation, as may be known for example from the prior art, cannot be straightforwardly applied to a different separation problem with a sufficient prospect of success. For each separation problem, the ideal elution conditions, in particular the mobile phase used, have to be determined by empirical testing.

In a preferred embodiment of the HPLC method according to the invention, a mixture of an aqueous solvent and an organic solvent is used as the mobile phase for eluting the RNA. It is favourable for a buffer to be used as the aqueous solvent which has in particular a pH of 6.0-8.0, for example of about 7, for example. 7.0; preferably the buffer is triethylammonium acetate (TEAA), particularly preferably a 0.02 M to 0.5 M, in particular 0.08 M to 0.12 M, very particularly an about 0.1 M TEAA buffer, which, as described above, also acts as a counterion to the RNA in the ion pair method.

In a preferred embodiment, the organic solvent which is used in the mobile phase comprises acetonitrile, methanol, ethanol, 1-propanol, 2-propanol and acetone or a mixture thereof, very particularly preferably acetonitrile. With these organic solvents, in particular acetonitrile, purification of the RNA proceeds in a particularly favourable manner with the method according to the invention.

In a particularly preferred embodiment of the method according to the invention, the mobile phase is a mixture of 0.1 M triethylammonium acetate, pH 7, and acetonitrile.

It has proven particularly favourable for the method according to the invention for the mobile phase to contain 5.0 vol. % to 25.0 vol. % organic solvent, relative to the mobile phase, and for this to be made up to 100 vol. % with the aqueous solvent. Typically, in the event of gradient separation, the proportion of organic solvent is increased, in particular by at least 10%, more preferably by at least 50% and most preferably by at least 100%, optionally by at least 200%, relative to the initial vol. % in the mobile phase. In a preferred embodiment, in the method according to the invention the proportion of organic solvent in the mobile phase amounts in the course of HPLC separation to 3 to 9, preferably 4 to 7.5, in particular 5.0 vol. %, in each case relative to the mobile phase. More preferably, the proportion of organic solvent in the mobile phase is increased in the course of HPLC separation from 3 to 9, in particular 5.0 vol. % to up to 20.0 vol. %, in each case relative to the mobile phase. Still more preferably, the method is performed in such a way that the proportion of organic solvent in the mobile phase is increased in the course of HPLC separation from 6.5 to 8.5, in particular 7.5 vol. %, to up to 17.5 vol. %, in each case relative to the mobile phase.

It has proven even more particularly favourable for the method according to the invention for the mobile phase to contain 7.5 vol. % to 17.5 vol. % organic solvent, relative to the mobile phase, and for this to be made up to 100 vol. % with the aqueous buffered solvent.

In the case of the method according to the invention elution may proceed isocratically or by means of gradient separation. In isocratic separation, elution of the RNA proceeds with a single eluent or a constant mixture of a plurality of eluents, wherein the solvents described above in detail may be used as eluent.

In a preferred embodiment of the method according to the invention, gradient separation is performed. In this respect, the composition of the eluent is varied by means of a gradient program. The equipment necessary for gradient separation is known to a person skilled in the art. Gradient elution may here proceed either on the low pressure side by mixing chambers or on the high pressure side by further pumps.

Preferably, in the method according to the invention, the proportion of organic solvent, as described above, is increased relative to the aqueous solvent during gradient separation. The above-described agents may here be used as the aqueous solvent and the likewise above-described agents may be used as the organic solvent.

For example, the proportion of organic solvent in the mobile phase may be increased in the course of HPLC separation from 5.0 vol. % to 20.0 vol. %, in each case relative to the mobile phase. In particular, the proportion of organic solvent in the mobile phase may be increased in the course of HPLC separation from 7.5 vol. % to 17.5 vol. %, in particular 9.5 to 14.5 vol. %, in each case relative to the mobile phase.

The following gradient program has proven particularly favourable for the purification of RNA with the method according to the invention:
  Eluent A: 0.1 M triethylammonium acetate, pH 7
  Eluent B: 0.1 M triethylammonium acetate, pH 7, with 25 vol. % acetonitrile
  Eluent composition:
    start: 62% A and 38% B (1st to 3rd minute)
    increase to 58% B (1.67% increase in B per minute), (3rd-15th minute) 100% B (15th to 20th minute)
Another example of a gradient program is described below, the same eluent A and B being used:
  Eluent composition:
    starting level: 62% A and 38% B (1st-3rd min)
    separation range I: gradient 38%-49.5% B (5.75% increase in B/min) (3rd-5th min)
    separation range II: gradient 49.5%-57% B (0.83% increase in B/min) (5th-14th min)
    rinsing range: 100% B (15th-20th min)

The flow rate of the eluent is so selected that good separation of the RNA from the other constituents contained in the sample to be investigated takes place. The eluent flow rate selected for the method according to the invention may amount to from 1 ml/min to several litres per minute (in the case of upscaling), in particular about 1 to 1000 ml/min, more preferably 5 ml to 500 ml/min, even more preferably more than 100 ml/min, depending on the type and scope of the upscaling. This flow rate may be established and regulated by the pump.

Detection proceeds favourably with a UV detector at 254 nm, wherein a reference measurement may be made at 600 nm. However, any other detection method may alternatively be used, with which the RNA described above in greater detail may be detected in satisfactory and reliable manner.

In preferred embodiments, the RP-HPLC is performed as described in WO 2008/077592.

As described above, the use of reversed phase chromatography methods typically requires the use of organic solvents such as acetonitrile (ACN), methanol, ethanol, 1-propanol, 2-propanol, trifluoroacetic acid (TFA), trifluoroethanol (TFE) or combinations thereof. However, these organic solvents may need to be removed from the RNA-containing pool afterwards. Furthermore, other contaminations derived from prior production or purification steps, such as spermidine, may still be present in the RNA-containing pool after RP-HPLC and need to be removed.

In a preferred embodiment, the at least one step of TFF in step C, may be performed after performing the at least one further purification method. This at least one step of TFF after the optional at least one purification method may comprise at least a first step of diafiltration. Preferably, the first diafiltration step is performed with an aqueous salt solution as diafiltration solution. In a preferred embodiment, the salt of the aqueous salt solution may comprise alkaline metal halides such as NaCl, LiCl or KCl; organic salts such as NaOAc, earth alkaline metal halides such as $CaCl_2$; alkaline metal phosphates such as $Na_3PO_4$, $Na_2HPO_4$, $NaH_2PO_4$; or combinations thereof. In a preferred embodiment, the salt of the aqueous salt solution may comprise alkaline metal halides such as NaCl, LiCl or KCl; earth alkaline metal halides such as $CaCl_2$. In a more preferred embodiment, the aqueous salt solution comprises from about 0.1 M alkaline metal halide to about 1 M alkaline metal halide, more preferably from about 0.2 to about 0.5 M alkaline metal halide. In another preferred embodiment, the aqueous salt solution comprises NaCl. In a more preferred embodiment, the aqueous salt solution comprises about 0.1 M NaCl to about 1 M NaCl, more preferably from about 0.2 to about 0.5 M NaCl. In a particularly preferred embodiment, the aqueous salt solution comprises 0.2 M NaCl. In another preferred embodiment, the aqueous salt solution does not comprise buffering salts. The presence of the salt may be advantageous for removing contaminating spermidine from the RNA-Pool. In a preferred embodiment, the first diafiltration step is performed using from about 1 to about 20 DV diafiltration solution, preferably from about 1 to about 15 DV diafiltration solution and more preferably from about 5 to about 12 DV diafiltration solution and even more preferably from about 7 to about 10 DV diafiltration solution. In a particularly preferred embodiment, the first diafiltration step is performed using about 10 DV diafiltration solution.

In a preferred embodiment, the RNA membrane load in the at least one step of TFF membrane (after the optional at least one purification method) is about 1 to about 10 $mg/cm^2$ and preferably from about 1 to about 5 $mg/cm^2$.

In a particularly preferred embodiment, the RNA membrane load of the TFF membrane is about 2 $mg/cm^2$ to about 2.5 $mg/cm^2$.

In a preferred embodiment of the present invention, the at least one step of TFF (after the optional at least one purification method) provides a feed flow rate of 500 to 2.000 $l/h/m^2$, preferably of 600 to 1.800 $l/h/m^2$, more preferably of 700 to 1.600 $l/h/m^2$ and most preferably of 900 to 1.500 $l/h/m^2$.

In a preferred embodiment of the present invention, the at least one step of TFF (after the optional at least one purification method) provides a permeate flux rate of at least 20 $l/h/m^2$, preferably at least 50 $l/h/m^2$, more preferably at least 100 $l/h/m^2$ and even more preferably at least 150 $l/h/m^2$.

In a preferred embodiment of the present invention, the at least one step of TFF (after the optional at least one purification method) provides a permeate flux rate of about 25 $l/h/m^2$ to about 140 $l/h/m^2$.

In another preferred embodiment, the transmembrane pressure (TMP) over the TFF membrane cassette in the at least one step of TFF (after the optional at least one purification method) is from about 0.01 (0.1 bar) to about 0.3 MPa (3 bar) and preferably from about 0.05 (0.5 bar) to about 0.2 MPa (2 bar) and most preferably from about 0.075 (0.75 bar) to about 0.15 MPa (1.5 bar). Furthermore, a deltaP (dp) of from about 0.05 (0.5 bar) to about 0.5 MPa (5 bar), more preferably of from about 0.05 (0.5 bar) to about 0.1 MPa (1 bar) and particularly of about 0.1 MPa (1 bar) is preferred. The values for TMP and dp of about 0.15 MPa (1.5 bar) and about 0.1 MPa (1 bar), respectively, are particularly preferred because under these conditions the process is not cake layer driven.

In a preferred embodiment, the values for TMP are from about 0.1 (1 bar) to about 0.15 (1.5 bar) and dp are about 0.1 MPa (1 bar).

In another preferred embodiment, the at least one step of TFF after the optional at least one further purification method comprises at least one step of concentrating the RNA, which is preferably performed before the first diafiltration step described above. In a preferred embodiment the RNA-Pool resulting from the optional at least one further purification method is concentrated to a concentration of from about 0.1 g/l to about 10 g/l, preferably to a concentration of from about 1 g/l to about 10 g/l and more preferably to a concentration of from about 2 g/l to about 5 g/l. In a particularly preferred embodiment, the RNA-Pool resulting from the optional at least one further purification method is concentrated to a concentration of from about 0.1 g/l to about 5 g/l. The concentrating of RNA by TFF may reduce the overall process time.

In yet another preferred embodiment, the first diafiltration step after the optional at least one purification method is followed by a second diafiltration step using TFF. In an even more preferred embodiment the second diafiltration step is performed using water as diafiltration solution. In a preferred embodiment, the first diafiltration step is performed using from about 1 to about 20 DV diafiltration solution, preferably from about 1 to about 15 DV diafiltration solution and more preferably from about 5 to about 12 DV diafiltration solution and even more preferably from about 6 to about 10 DV diafiltration solution. In a particularly preferred embodiment, the second diafiltration step is performed using about 10 DV diafiltration solution. In a preferred embodiment, a step of concentrating the RNA using TFF is performed after the second diafiltration step.

In a particularly preferred embodiment, the at least one further purification method is followed by at least one step of concentrating the RNA, at least one first diafiltration step and at least one second diafiltration step using TFF as described above.

In a particularly preferred embodiment, the diafiltration step after the optional at least one further purification method as well as the concentration step after the optional at least one further purification method using TFF are performed at temperatures from 0° C. to 20° C., more preferably from 5° C. to 20° C., even more preferably from 10° C. to 20° C., even more preferably at temperatures below 20° C., even more preferably at temperatures below 17° C.

In yet another particularly preferred embodiment, the method comprises in step C) the steps of:
C1) optionally termination of transcription;
C2) conditioning and/or purifying of the solution comprising the in vitro transcribed RNA by one or more steps of TFF;
C3) purifying the RNA by any further purification method as described above, preferably by using a method selected from the group consisting of cation exchange chromatography, anion exchange chromatography, membrane absorbers, reversed phase chromatography, normal phase chromatography, size exclusion chromatography, hydrophobic interaction chromatography, mixed mode chromatography, affinity chromatography, hydroxyapatite (HA) chromatography, or combinations thereof and more preferably reversed phase chromatography; and
C4) conditioning and/or optionally purifying of the solution comprising the transcribed RNA obtained after step C3) by one or more steps of TFF.

In a preferred embodiment, the optional termination of transcription of step C1) may comprise the addition of an effective amount of a cation complexing agent such as EDTA. EDTA may efficiently stop the in vitro transcription reaction and also deactivates nucleases and stabilizes the RNA due to the depletion of divalent cations. Moreover, addition of EDTA to the IVT-mix results in partial reduction of potentially occurring turbidity. It was also found that the addition of EDTA allows higher flow rates during subsequent TFF steps.

In a preferred embodiment, from about 10 to about 100 mM EDTA, preferably from about 10 to about 50 mM EDTA and even more preferably from about 20 to about 30 mM EDTA is added.

In a particularly preferred embodiment, 25 mM EDTA is added.

It was surprisingly found that TFF is particularly suitable for the conditioning of the solution comprising the transcribed RNA compared to other alternative conditioning methods such as using fast performance liquid chromatography (FPLC) column affinity chromatography which showed irreversible binding of RNA and RNA elution could only be achieved by washing the column with NaOH or most RNA was found in the flow-through.

In another preferred embodiment, step C4 comprises at least a first diafiltration step using TFF as described above; more preferably at least a first diafiltration step using TFF and at least a second diafiltration step as described above; and even more preferably at least one concentration step using TFF as described above, at least a first diafiltration step using TFF and at least a second diafiltration step as described above.

Thus, in a preferred embodiment the at least one first step of diafiltration in step C4 is performed with an aqueous salt solution as diafiltration solution. In a preferred embodiment, the salt of the aqueous salt solution may comprise alkaline metal halides such as NaCl, LiCl or KCl; organic salts such as NaOAc, earth alkaline metal halides such as $CaCl_2$; alkaline metal phosphates such as $Na_3PO_4$, $Na_2HPO_4$, $NaH_2PO_4$; or combinations thereof. In a preferred embodiment, the salt of the aqueous salt solution may comprise alkaline metal halides such as NaCl, LiCl or KCl; earth alkaline metal halides such as $CaCl_2$. In a more preferred embodiment, the aqueous salt solution comprises from about 0.1 M alkaline metal halide to about 1 M alkaline metal halide, more preferably from about 0.2 to about 0.5 M alkaline metal halide. In another preferred embodiment, the aqueous salt solution comprises NaCl. In a more preferred embodiment, the aqueous salt solution comprises about 0.1 M NaCl to about 1 M NaCl, more preferably from about 0.2 to about 0.5 M NaCl. In a particularly preferred embodiment, the aqueous salt solution comprises 0.2 M NaCl. In another preferred embodiment, the aqueous salt solution does not comprise buffering salts. The presence of the salt may be advantageous for removing contaminating spermidine from the RNA-Pool. In a preferred embodiment, the first diafiltration step is performed using from about 1 to about 20 DV diafiltration solution, preferably from about 1 to about 15 DV diafiltration solution and more preferably from about 5 to about 12 DV diafiltration solution and even more preferably from about 7 to about 10 DV diafiltration solution. In a particularly preferred embodiment, the first diafiltration step is performed using about 10 DV diafiltration solution.

In a preferred embodiment, the at least one second diafiltration step is performed using water as diafiltration solution. In a preferred embodiment, the first diafiltration step is performed using from about 1 to about 20 DV diafiltration solution, preferably from about 1 to about 15 DV diafiltration solution and more preferably from about 5 to about 12 DV diafiltration solution and even more preferably from about 6 to about 10 DV diafiltration solution. In a particularly preferred embodiment, the second diafiltration step is performed using about 10 DV diafiltration solution. In a preferred embodiment, a step of concentrating the RNA using TFF is performed after the second diafiltration step.

In a particularly preferred embodiment, the diafiltration solution does not comprise buffering salts in all TFF steps of the inventive method.

It is particularly preferred that all TFF steps according to the present invention, i.e. steps A3, C2 and C4 as defined herein, are performed with the same type of TFF membrane, preferably with the same type of TFF membrane cassette. Even more preferably, all TFF steps according to the present invention are performed with a TFF membrane cassette comprising an mPES-based filter membrane with a MWCO of 100 kDa or a cellulose-based filter membrane with a MWCO of 100 kDa, e.g., commercially available TFF membrane cassettes such as NovaSep mPES with a MWCO of 100 kDa and Hydrosart (Sartorius) cellulose-based membrane cassette with a MWCO of 100 kDa. Most preferably, all TFF steps according to the present invention are performed with a TFF membrane cassette comprising a cellulose-based filter membrane with a MWCO of 100 kDa.

The skilled person will readily appreciate that the above comments on step A3 also apply to steps d) and e) and to step iv). Similarly, the above comments on step C2 also apply to step h) and the comments on step C4 also apply to steps j) and k), respectively.

Optional Steps D to F:

In yet another embodiment, the method according to the present invention comprises at least one additional formulation step D), e.g. the complexation of the purified RNA with polycationic compounds, such as polycationic polymers or polycationic peptides or proteins, e.g. protamine. In this context the depletion of spermidine is absolutely necessary in order to provide a sufficient complexation with polycationic compounds.

In yet another embodiment, the method according to the present invention further comprises steps of E) filling and/or F) lyophilization.

The present invention was made with support from the Government under Agreement No. HR0011-11-3-0001 awarded by DARPA. The Government has certain rights in the invention.

BRIEF DESCRIPTION OF THE FIGURES

FIGS. 1A-B: Feed stream passes parallel to the membrane face as one portion passes through the membrane (permeate/filtrate) (FIG. 1A) while the remainder (retentate) is recirculated from the filtration module back to the feed reservoir (FIG. 1B; adapted from Millipore literature No. TB032); concentration, diafiltration (desalting and buffer exchange), and fractionation of large from small molecules are possible.

FIGS. 2A-B: Results of MWCO screening with linearized pDNA

FIG. 2A shows the results of MWCO screening experiments from linearization reactions of three different plasmids: P0625 (2626 bp), P1040 (3907 bp), and P0532 (7362 bp). It can be easily seen that using spin filters of both manufacturers with 100 kDa MWCO retained the three different linearized pDNAs almost completely, whereas higher MWCO lead to loss of linearized plasmid DNA.

FIG. 2B shows DNA agarose gel electrophoresis of MWCO screening with the linearized plasmid P1040 (3907 bp). The samples of linearization of P1040 and the resulting filtration samples are shown in the DNA agarose gel electrophoresis. LA: 0.5 μg of the linearization reaction as control. The analysed samples were diluted, and the fixed amount of 0.5 μg DNA per lane was applied to the gel. If the DNA concentration was too low, the maximum amount of DNA was applied. Due to the standardization in DNA application, no quantitative statement can be given regarding the retaining of DNA. However the analysis shows that the integrity of DNA did not decrease during filtration. Furthermore it can be seen from the gel that higher MWCO than 100 kDa lead to a loss of plasmid DNA in the retentate.

FIG. 3A shows the results of MWCO screening of RNA after transcription reaction for three different mRNA lengths (R1871: 589 nt, R1265: 1870 nt, R 1626: 5337 nt). It can be easily seen that using spin filters of both manufacturer's with 100 kDa MWCO retain the three different mRNAs completely.

FIG. 3B shows RNA agarose gel electrophoresis for the resulting filtration samples of the RNA R1265. The analysed samples were diluted, and the fixed amount of 1 μg mRNA per lane was applied to the gel. If the mRNA concentration was too low, the maximum amount of mRNA was applied. Due to that standardization in mRNA application, no quantitative statement can be given regarding the retaining of mRNA. However the analysis shows that the integrity of mRNA did not decrease during filtration. The gel reflected the same results, as measured in RNA concentration measurement, that the RNA R1265 was retained completely by the 100 kDa membrane.

RNA in WFI (3775 nt, mRNA after transcription reaction, diafiltrated in WFI) was used to perform a flow rate screening using a hollow fibre membrane (GE, PES, 100 kDa, 50 cm$^2$). As shown above, an increase in feed flow (FF) led to an increase in permeate flux, also the addition of retentate pressure (0.5 bar) showed an impact on permeate flux rate.

Figure 5:
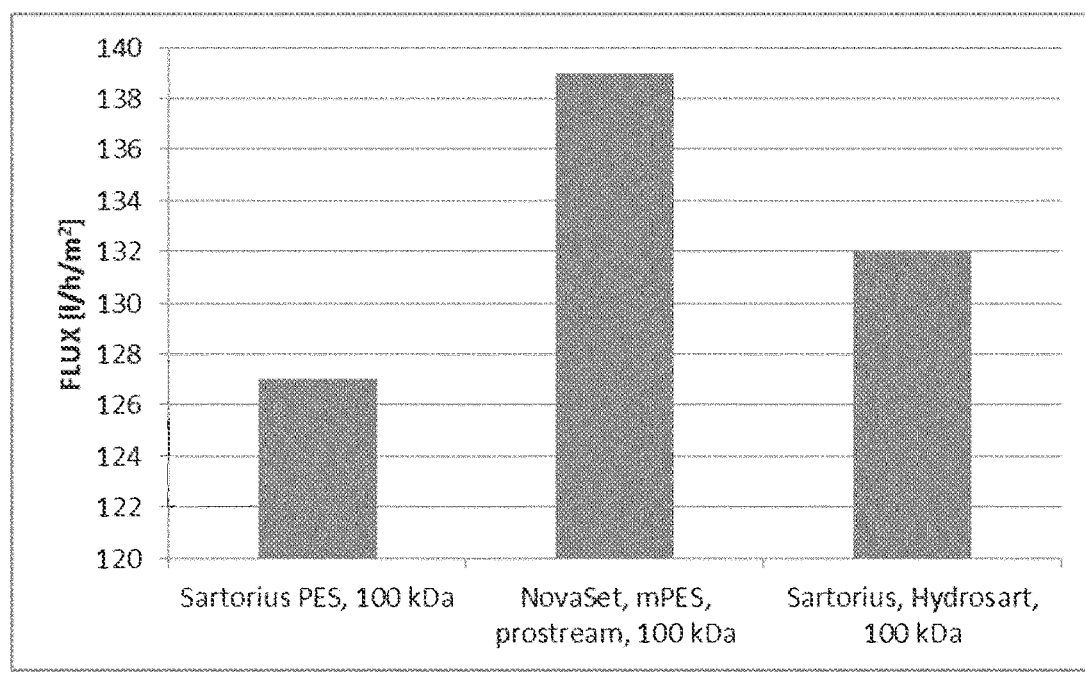

FIG. 5: Permeate flux rates of different TFF cassettes at dp and TMP of 1 bar.

The flux rates for three different TFF cassettes were in a range of 126 to 140 l/h/m$^2$.

FIG. 6: RNA stability after transcription reaction (A) and after subsequent TFF diafiltration to WFI for several hours (B). RNA integrity (relative area of full-length product) was determined by analytical RP-HPLC after storage at different temperatures (room temperature, 5° C. and −20° C.). The in vitro transcription reaction without TFF was analyzed for RNA integrity after 1, 3, 5, 7, 10, 13, 14, 53 and 61 days. The in vitro transcription reaction after TFF was analyzed for RNA integrity after 1, 5, 7, 12, 14 and 33 days.

Figure 7:
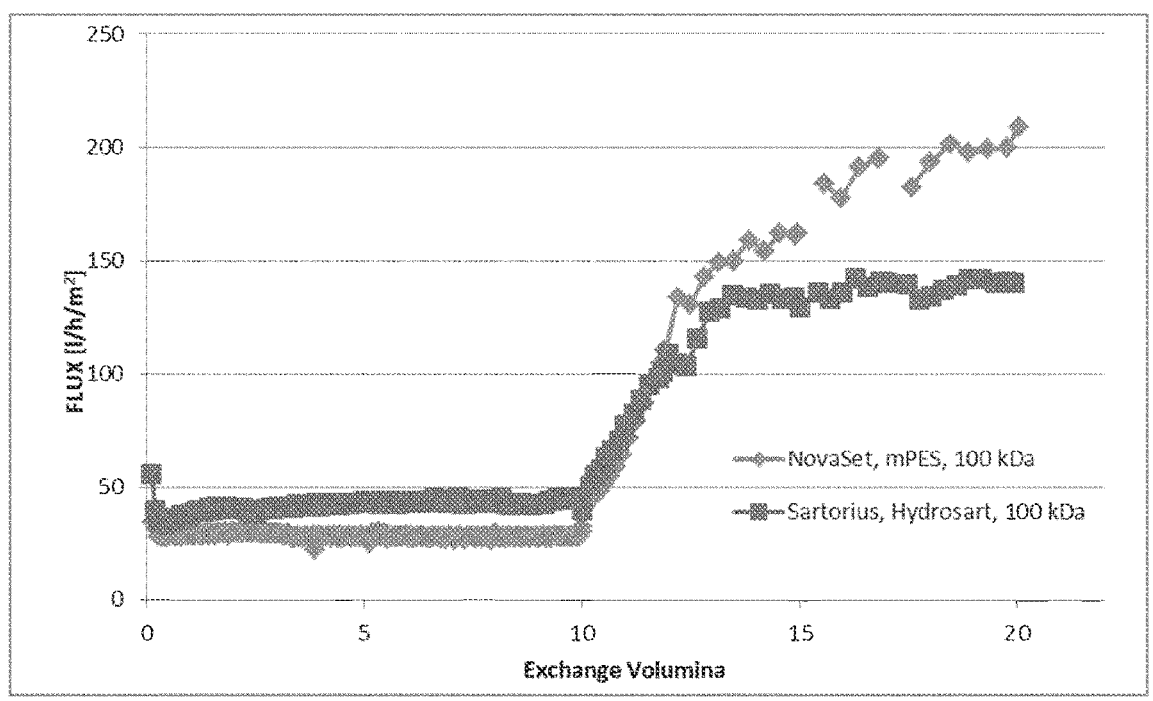

FIG. 7: Test of different membranes for spermidine depletion step

Two membranes (Novasep mPES 100 kDa and the cellulose-based Sartorius Hydrosart 100 kDa) were tested for the spermidine depletion step using 0.2 M NaCl for diafiltration. Both membranes showed comparable FLUX rates.

Figure 8:
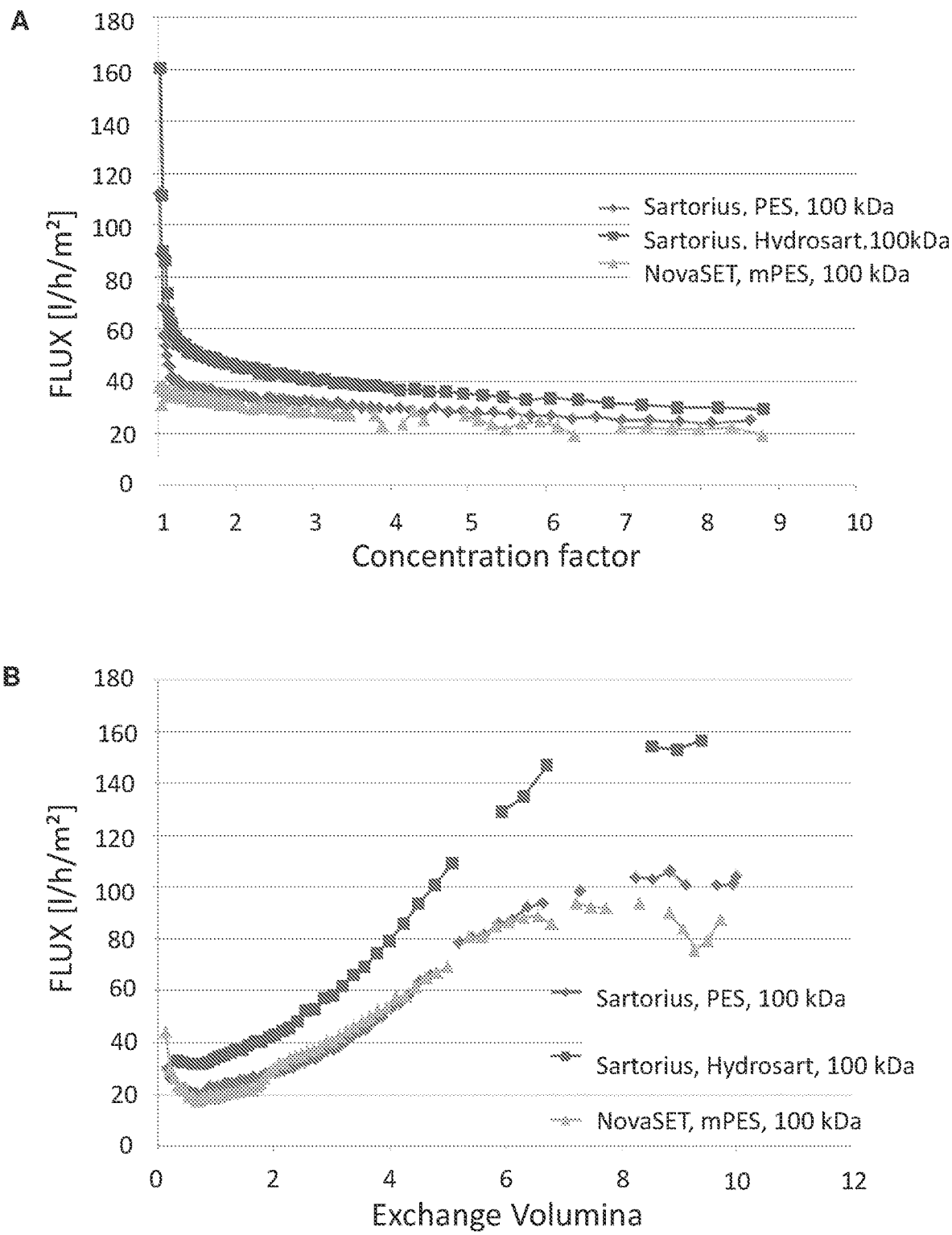

FIGS. 8A-B: Test of different membranes for TFF of linearization reaction with higher membrane load For concentration and diafiltration of the linearization reaction TFF membranes made from different material, with a MWCO of 100 kDa and membrane area of 200 cm$^2$ from different suppliers (The PES-based membranes Sartocon Slice 200 from Sartorius and the NovaSet-LS ProStream (Low Binding mPES) from NovaSep and the cellulose-based membrane Sartocon Slice 200, Hydrosart from Sartorius) were tested with a high membrane load (5.6 and 6 g plasmid DNA/m$^2$).

Flux rates in the concentration step are shown in FIG. 8A. The linearization reaction was concentrated from 0.2 g/l to approximately 1.5 g/l. The following parameters were used: dp and TMP=1 bar (P1=1.5 bar, P2=0.5 bar and P3=0 bar)

Flux rates in the diafiltration step are shown in FIG. 8B. The linearization reaction was diafiltrated against 10 diafiltration volumes WFI with the same parameters used for concentration.

All tested membranes showed similar results. During concentration of the linearization reaction (FIG. 8A), FLUX rates decreased rapidly, but during diafiltration in WFI (FIG. 8B) the FLUX-rates increased again. Both PES-based membranes (Sartorius PES and NovaSet mPES) showed similar results, however, the Hydrosart membrane (Sartorius) showed higher permeate flow rates.

Figure 9:
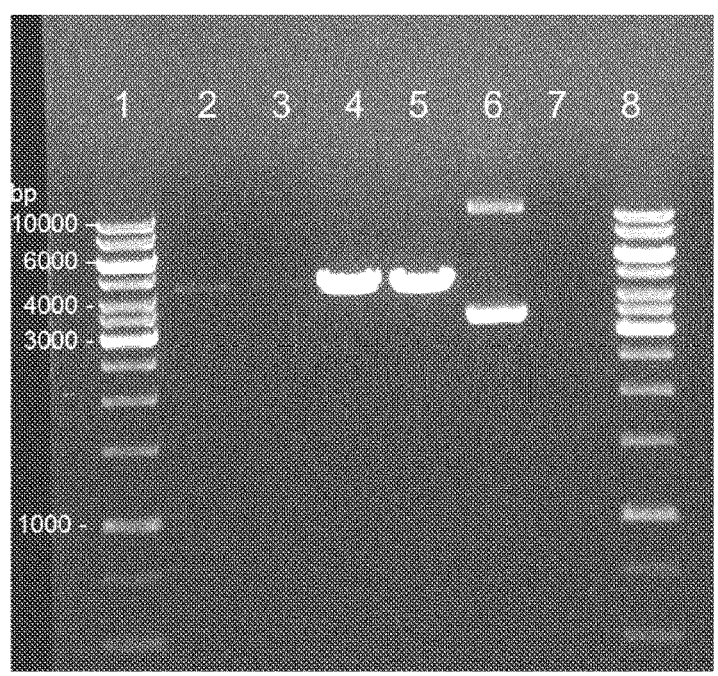

FIG. 9: Agarose gel electrophoresis of linearized pDNA
1.) DNA size marker
2.) TFF permeate after concentration (10 µl)
3.) TFF permeate after diafiltration (10 µl)
4.) TFF retentate (3 µl of 0.1 g/l)
5.) Control linearized plasmid (1.8 µl of 0.17 g/l)
6.) Control circular plasmid (3 µl of 0.1 g/l)
7.) Empty
8.) DNA size marker Only a negligible amount of plasmid DNA is visible in the permeate of the concentration step and of the diafiltration step.

Figure 10:
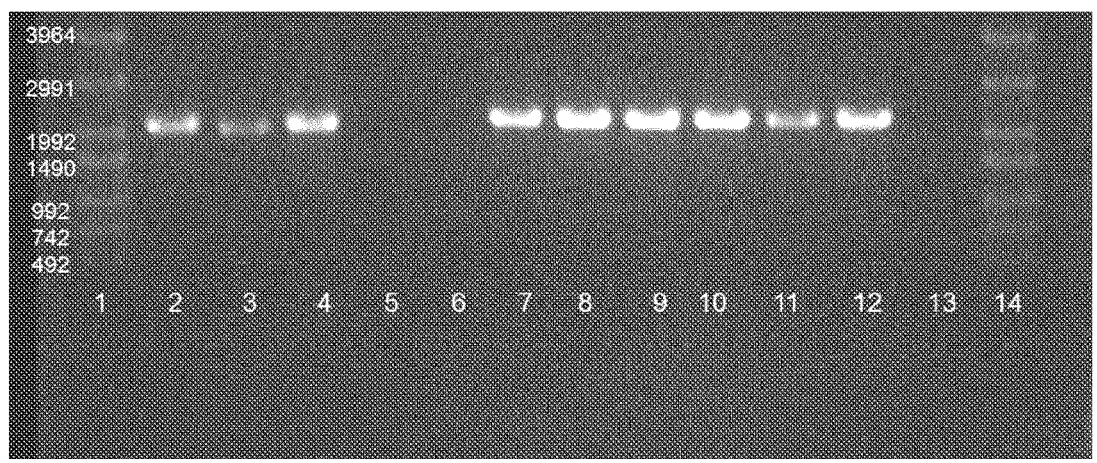

FIG. 10: RNA agarose gel electrophoresis of permeate and retentate samples taken during TFF of the RP-HPLC pools
1.) RNA marker
2.) RP-HPLC Pool I
3.) RP-HPLC Pool II
4.) RP-HPLC Pool III
5.) TFF permeate
6.) TFF permeate (40× concentrated)
7.) TFF retentate Pool I
8.) TFF retentate Pool II
9.) TFF retentate Pool III
10.) Final product
11.) Control
12.) Control
13.) empty
14.) RNA marker FIG. 11: Protein SDS PAGE samples taken during RNA production and purification process
1 Protein Marker
2 TFF retentate after linearization
3 transcription reaction
4 TFF retentate before RP-HPLC
5 TFF retentate before RP-HPLC
6 TFF retentate before RP-HPLC
7 TFF retentate after RP-HPLC Pool I
8 TFF retentate after RP-HPLC Pool II
9 TFF retentate after RP-HPLC Pool III
10 Final Product
11 control
12 Protein Marker FIG. 12: TFF permeate flux rates. Concentration of pDNA linearization reaction from 0.2 to 1.5 g/l DNA, using Hydrosart 100 kDa, dp and TMP 1 bar; Membrane load: 6 g/m$^2$; Concentration from 0.2 g/l DNA to 1.5 g/l DNA.

Figure 13:
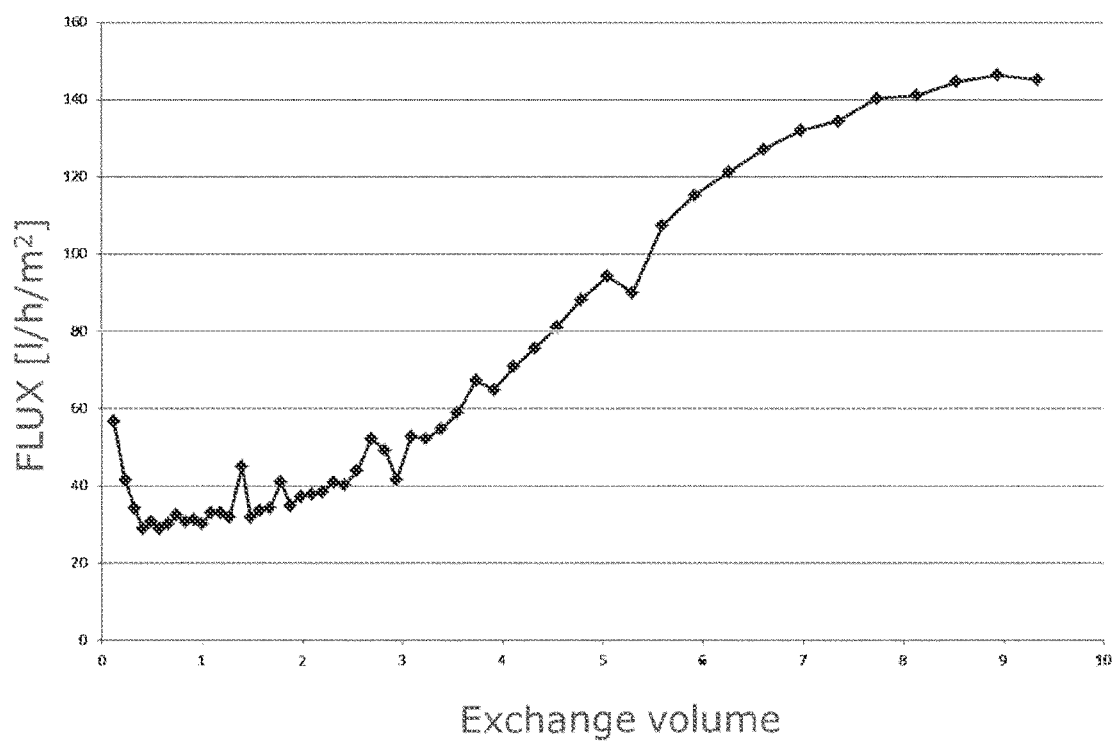

FIG. 13: TFF permeate flux rates. Diafiltration of linearized pDNA into 10 DFV WFI using Hydrosart 100 kDa, dp and TMP 1 bar; Membrane load: 6 g/m$^2$.

Figure 14:
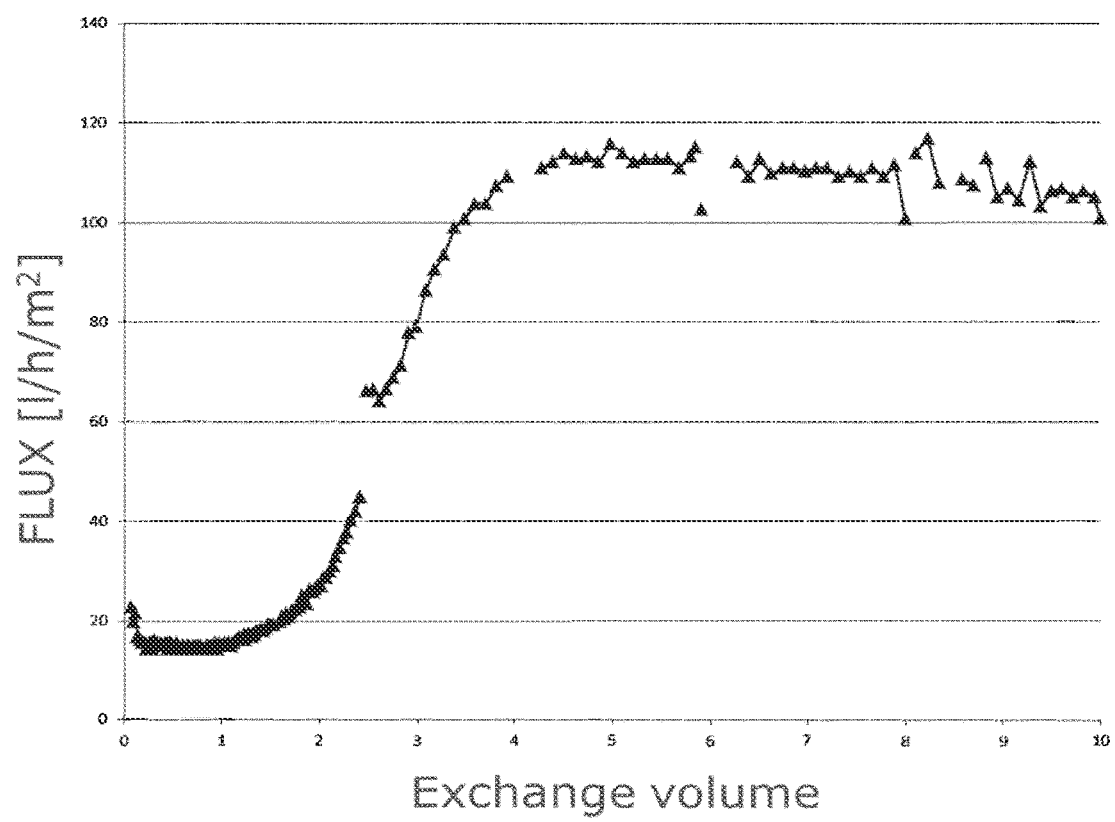
Figure 15:
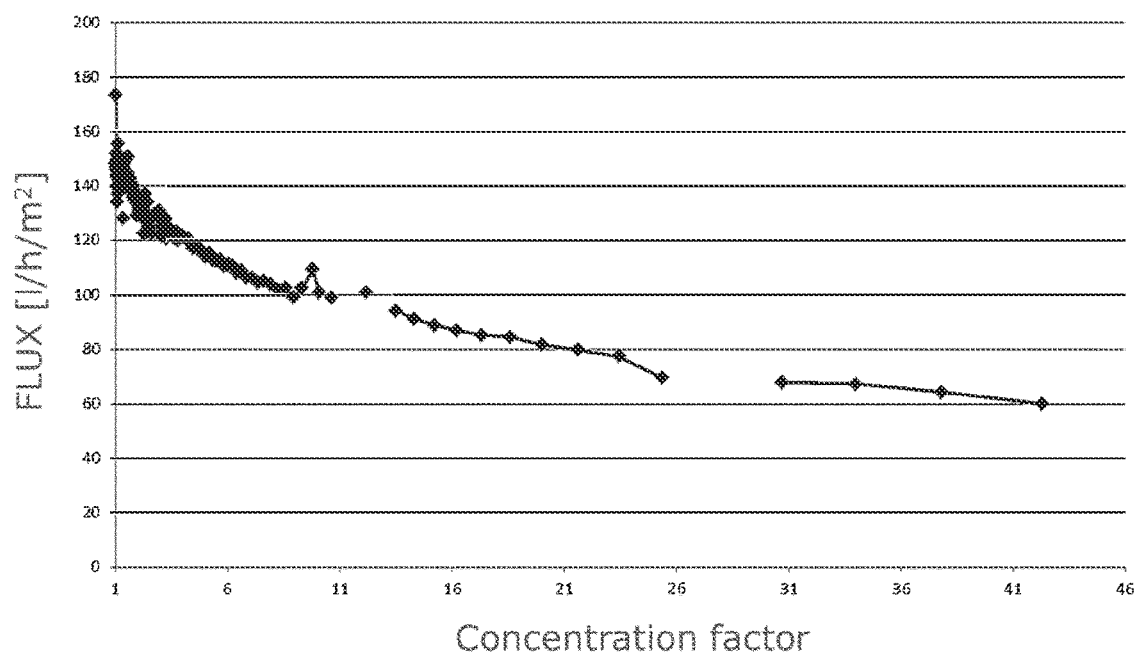

FIG. 14: TFF permeate flux rates. Diafiltration of RNA IVT-mix into 10 DFV WFI using Hydrosart 100 kDa, dp and TMP 1 bar; Membrane load: 56 g/m$^2$;

FIG. 15: TFF permeate flux rates. Concentration of RP-HPLC RNA pool, using Hydrosart 100 kDa, dp and TMP1 bar; Membrane load: 20 g/m$^2$; Concentration from 0.1 g/l RNA to 5 g/l RNA; Temperature 17° C.

Figure 16:
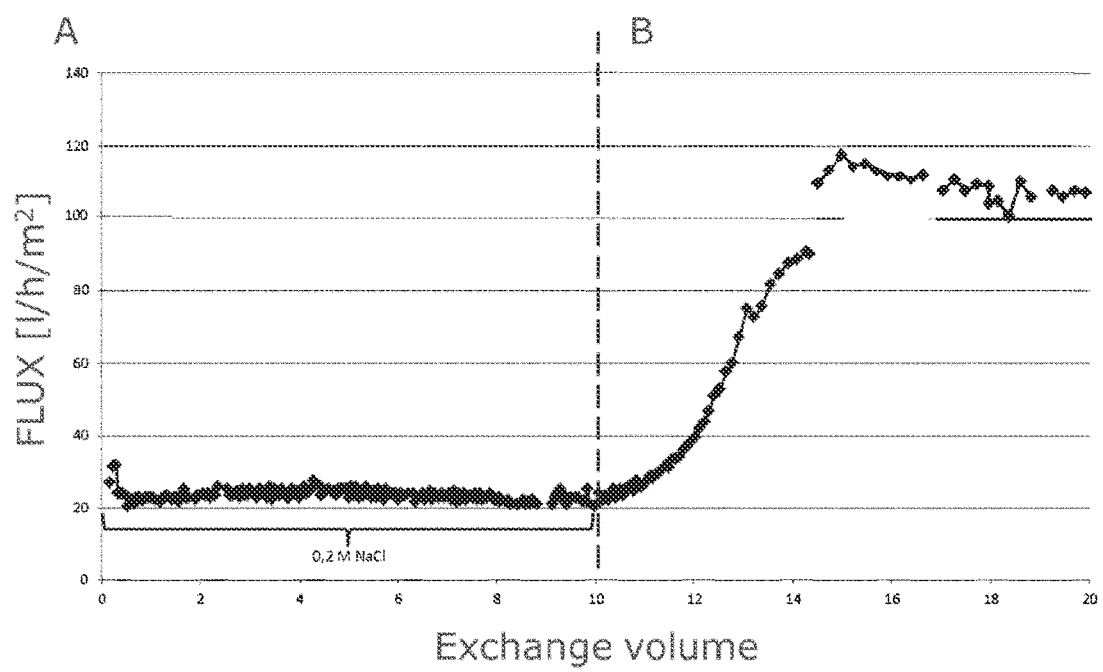

FIG. 16: TFF permeate flux rates. Diafiltration of RNA, using Hydrosart 100 kDa, dp and TMP 1 bar. (A) Diafiltration of RNA into 10 DFV 0.2 M NaCl; (B) Diafiltration of RNA into 10 DFV WFI.

EXAMPLES

Example 1—Materials

The following materials of Table 1 were used in the subsequent experimental section:

TABLE 1

| Materials | |
|---|---|
| Equipment | Manufacturer |
| Vivaflow 50, PES, 100 kDa | Sartorius |
| Sartocon Slice 200 100 kDa, PES | Sartorius |
| Sartocon Slice 200 100 kDa, Hydrosart (cellulose-based membrane) | Sartorius |
| Sartcocon Slice 200 300 kDa, PES | Sartorius |
| Omega Centramate T OS100T02, PES 100 kDa | PALL GmbH |
| NovaSet-LS ProStream (Low Binding mPES), 100 kDa | NovaSep |
| Hollow fibre module, 100 kDa, PES | GE-Healthcare |
| Spin-Filter Nanosep ® (100 kDa), PES | Pall GmbH |
| Spin-Filter Nanosep ® (300 kDa), PES | Pall GmbH |
| Spin-Filter Nanosep ® (1000 kDa), PES | Pall GmbH |
| Spin-Filter Vivaspin ® 500 (100 kDa), PES | Sartorius |
| Spin-Filter Vivaspin ® 500 (300 kDa), PES | Sartorius |
| Spin-Filter Vivaspin ® 500 (1000 kDa), PES | Sartorius |
| Vivaflow 50 Modul, PES, 100 kDa | Sartorius |
| Sartoflow Slice 200, PES, 100 kDa | Sartorius |

General Methods

Example 2—Linearization of Plasmid DNA

The following conditions were used for linearization of the plasmid DNA:
1 µg plasmid DNA
0.5 µl reaction buffer
3 Units restriction enzyme EcoRI
Add. 5 µl with WFI (water for injection)

The reaction was incubated for 3 hours at 37° C. and stopped by heat-inactivation of the restriction enzyme (65° C., 30 minutes).

Example 3—General Description of the TFF Process

All tubes and the retentate vessel were cleaned with 75% EtOH and water and were assembled. The membrane cassette was fixed into the corresponding holder, according to the manufacturer's instruction, and respectively the hollow fibre membrane was connected to the system. Afterwards, the system and membrane was flushed with at least 1 L water, 1 L 1 M or 0.5 M NaOH for 1 hour (for removal of potential contaminants, like RNases) and was washed again with water, until pH value in the permeate was neutral. Subsequently, the whole system was flushed with water for injection (WFI) or diafiltration solution or buffer.

3.1—Concentration Step

DNA/RNA-solution was filled into the retentate vessel, and was optionally concentrated to the required concentration, by setting the indicated pressures.

3.2—Diafiltration Step

After the optional concentration step, diafiltration was started. Therefore the diafiltration tube was placed into the diafiltration solution or buffer. During diafiltration, the amount of permeate which left the system was automatically replaced by diafiltration solution or buffer, due to the emerging vacuum. When the required diafiltration volume (dv) was reached, a different diafiltration solution or buffer was optionally added to the system, and a second diafiltration step was carried out. Before ending of the TFF step, the retentate was optionally again concentrated to the required volume, before withdrawal of the retentate from the system. Subsequently the system was flushed with 25 mL WFI (water for injection) or buffer (permeate valve closed). Flushing liquid was optionally pooled with the TFF retentate. Optionally, RNA/DNA concentration was measured and recovery of nucleic acid calculated.

3.3—System/Membrane Maintenance

After usage of the membranes, the cassette was flushed with 0.5 L water, subsequently with 0.5 M or 1 M NaOH for 1 hour, and again with water, until pH in the permeate was neutral. Afterwards, the water permeate flux value was determined to verify the cleanness of the membrane. At the end, the membrane was removed from the TFF system and stored in either 0.1 M NaOH or in 20% EtOH. The TFF system was afterwards cleaned with 75% EtOH and water and stored dryly.

Example 4—In Vitro Transcription 4.1—In Vitro Transcription

The linearized DNA plasmids were transcribed in vitro using T7 polymerase. The in vitro transcription was performed in the presence of a CAP analog (m7GpppG). The in vitro transcription was carried out in 5.8 mM m7G(5')ppp (5')G Cap analog, 4 mM ATP, 4 mM CTP, 4 mM UTP, and 1.45 mM GTP, 50 µg/ml DNA plasmid, 80 mM HEPES, 24 mM $MgCl_2$, 2 mM Spermidine, 40 mM DTT, 100 U/µg DNA T7 RNA polymerase, 5 U/µg DNA pyrophosphatase, and 0.2 U/µl RNAse inhibitor.

The in vitro transcription reaction was incubated for 4 hours at 37° C.

After transcription the reaction was stopped by adding ETDA to a final concentration of 25 mM.

4.2—DNA Template Removal: DNase I Treatment

To digest DNA template 6 µl DNAse I (1 mg/ml) and 0.2 µl $CaCl_2$) solution (0.1 M)/µg plasmid DNA were added to the transcription reaction, and incubated for 3 h at 37° C.

Example 5—HPLC Purification of the RNA

The RNA was purified using PureMessenger® (CureVac, Tubingen, Germany; WO2008/077592A1).

Briefly, the TFF conditioned transcription reaction was purified using Reversed-Phase High pressure liquid chromatography (RP-HPLC). The RP-HPLC was performed with a macroporous styrene/divinylbenzene column (particle size 30 µm, pore size 4000 Å) and column dimensions of 21.2 mm×250 mm (volume 88.25 ml).

1 g/l RNA in 100 mM triethylammonium acetate (TEAA) was prepared, filtered with a 5 µm PVDF filter and used for preparative RP-HPLC. After mounting the column (stored in 88% acetonitrile), the storage solution was washed out with ultra-pure water. Next, the RNA sample was loaded onto the column and eluted with an eluent B/eluent A—gradient (eluent A: 100 mM triethylammonium acetate (TEAA) in (water for injection (WFI), pH 7.0; eluent B: 100 mM TEAA in 25% acetonitrile) starting with 100% eluent A, and ending with 100% eluent B. During the elution procedure, fractions were automatically collected. Subsequently fractions were analyzed for RNA content by photometrical determination (A260) and for RNA integrity by agarose gel electrophoresis or analytical HPLC.

Example 6—Analytical Methods 6.1—RNA Gel Electrophoresis

RNA was separated in formaldehyde-containing agarose gels (0.7% w/w formaldehyde, 1.2% w/v agarose) in 3-Morpholinopropane sulfonic acid buffer (for details on method see Sambrook, Russel: Molecular Cloning: A Laboratory Manual, vol. 3, Cold Spring Harbor Laboratory, 2000). RNA samples were denatured in RNA sample buffer (Thermo scientific) at 80° C. for 5 min before loading on the gel. 1 µg of RNA was loaded per lane.

6.2—Protein Gel Electrophoresis (SDS-PAGE)

SDS-PAGE was performed with ready-to-use 12% Mini-PROTEAN TGX gels (Bio-Rad). 4× Laemmli sample loading buffer and 10×SDS-PAGE running buffer were purchased from Bio-Rad. Samples were mixed with 4× loading buffer and incubated at 95° C. for 5 min. Sample load was normalized to 10 µg RNA per lane. A voltage of 150 mV (corresponding to approx. 35 mA per gel) was applied until the smallest marker band reached the lower end of the gel. Visualization of protein bands was performed with ready-to-use Simply Blue Safe Stain (Invitrogen) according to the protocol of the manufacturer. Alternatively, the Pierce Silver Stain Kit (Thermo Scientific) was used in order to increase staining sensitivity.

6.3—Quantification of RNA-Bound Spermidine

Spermidine was quantified by a modified protocol as described in Flores et al. (Plant Physiol. (1982) 69, 701-

706)). Briefly, spermidine is benzoylated under alkaline conditions followed by extraction with diethylether. Benzoylated spermidine is detected and quantified by HPLC or mass spectrometry. Hexamethylene diamine is used as an internal standard.

6.4—Determination of Residual Solvents

The content of residual solvents in the RNA sample was determined using quantitative gas-chromatography with flame ionization detector (GC-FID).

Pilot Tests

Example 7—Pore Screening Experiments 7.1—MWCO Screening with Plasmid DNA.

For determination of suitable MWCO (molecular weight cut-off) of membranes used in TFF, a MWCO-screening was conducted. Therefore spin filters were used, as they require small volumes. Spin filters from two different manufacturers (Spin-Filter Nanosep® (100 kDa, 300 kDa and 1000 kDa), PES from PALL GmbH and Spin-Filter Vivaspin® 500 (100 kDa, 300 kDa and 1000 kDa), PES from Sartorius) were tested with a MWCO of 100, 300 and 1000 kDa. Prior to use, the spin filters were flushed with 500 µl WFI (water for injection), and WFI was removed from the permeate compartment completely. Subsequently, 300 µl of three different linearization reactions (see Example 2) were added and centrifuged at room temperature, according to the manufacturer's instructions. After approximately half the volume had passed the membrane, centrifugation was stopped and the exact volume in the permeate and retentate chamber was determined. Retentate chamber was then flushed with 100 µl WFI and combined with the retentate. Beside volume measurement, also the concentration of DNA was determined in the starting solution and retentate solution. DNA concentration was determined photometrically by measuring the absorption at 260 nm. FIG. 2A, shows the results of MWCO screening from linearization reactions of three different plasmids: P0625 (2626 bp), P1040 (3907 bp), P0532 (7362 bp). It can be easily seen, that using spin filters of both manufacturer's with 100 kDa MWCO retain the three different linearized pDNAs almost completely, whereas higher MWCO leads to loss of linearized plasmid DNA.

The samples of linearization P1040 and the resulting filtration samples are shown in FIG. 2B by DNA agarose gel electrophoresis. The analyzed samples were diluted, and the fixed amount of 0.5 µg DNA per lane were applied to the gel, if the DNA concentration was too low, the maximum amount of DNA was applied. Due to the standardization in DNA application, no quantitative statement can be given regarding the retaining of DNA. However the analysis shows that the integrity of DNA did not decrease during filtration. Furthermore it can be seen from the gel that higher MWCO than 100 kDa leads to a loss of plasmid DNA in the retentate. Therefore a MWCO of 100 kDa was chosen for further experiments regarding TFF of linearized plasmid DNA.

7.2—MWCO Screening with RNA

Figure 3A:
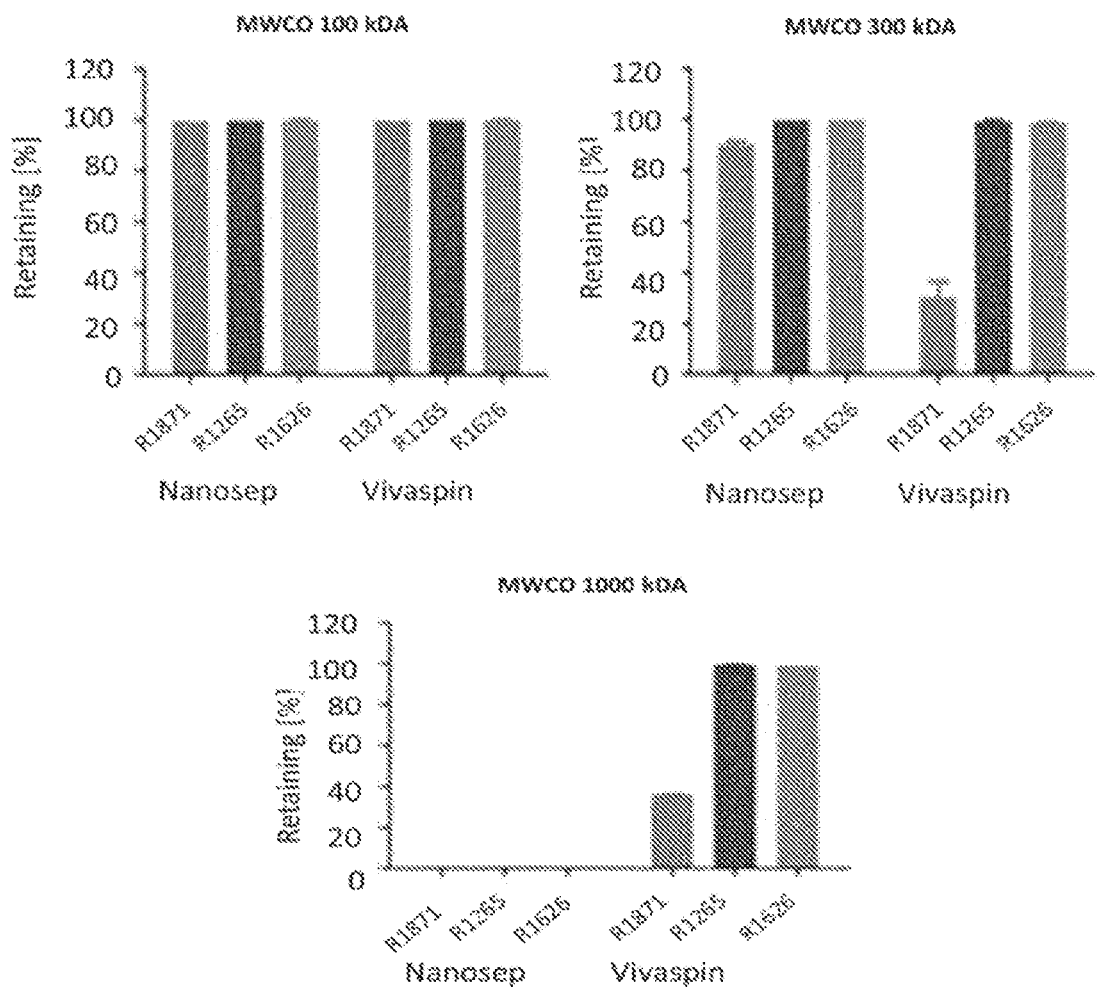
FIGS. 3A-B Results of MWCO screening with mRNA.

The experiment was conducted in the same way, as described for MWCO screening with pDNA (Example 7.1). Prior to use, the spin filters were flushed with 500 µl WFI, and WFI was removed from the permeate compartment completely. After that, 300 µl of three different transcription reactions were added and centrifuged at room temperature, according to the manufacturer's instructions. After approximately half the volume had passed the membrane, centrifugation was stopped and the exact volume in the permeate and retentate chamber was determined. Retentate chamber was then flushed with 100 µl WFI and combined with the retentate. Beside volume measurement, also the concentration of RNA was determined photometrically by measuring the absorption at 260 nm in the starting solution and retentate solution. FIG. 3A shows the results of MWCO screening of RNA after transcription reaction according to Example 4 for three different mRNA lengths (R1871: 589 nt, R1265: 1870 nt, R 1626: 5337 nt). It can be easily seen, that using spin filters of both manufacturer's with 100 kDa MWCO retain the three different mRNAs completely.

Figure 3B:
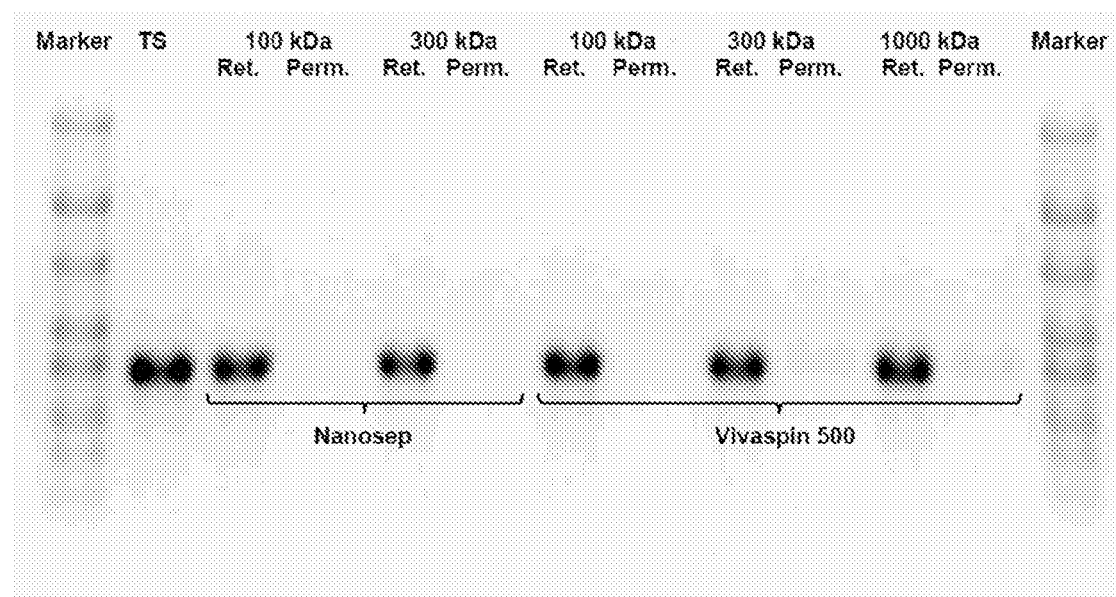

Furthermore in FIG. 3B RNA agarose gel electrophoresis is shown for the resulting filtration samples of the RNA R1265. The analysed samples were diluted, and the fixed amount of 1 µg mRNA per lane was applied to the gel, if the mRNA concentration was too low, the maximum amount of mRNA was applied. Due to that standardization in mRNA application, no quantitative statement can be given, regarding the retaining of mRNA. However the analysis shows that the integrity of mRNA did not decrease during filtration. The gel reflects the same results, as measured in RNA concentration measurement that the RNA R1265 is retained completely by the 100 kDa membrane, with a higher MWCO RNA is visible in the permeate. Therefore a MWCO of 100 kDa was selected for further experiments regarding TFF of RNA solutions.

Example 8—Parameter Screening of Different Membranes

The in vitro transcription reaction R2587 (according to Example 4) already diafiltrated in WFI was used for parameter screening. The different membranes (Sartocon Slice 200 100 kDa, PES from Sartorius, Sartocon Slice 200 100 kDa, Hydrosart (cellulose-based membrane) from Sartorius and NovaSet-LS ProStream (Low Binding mPES), 100 kDa from Novasep) were screened in respect to permeate flux versus TMP and dp, respectively. The sample load was 0.1 mg RNA/cm² membrane. The Hydrosart membrane (cellulose-based membrane from Sartorius) showed the highest permeate flow rate compared to the other membranes (polyethersulfone (PES)-based membranes from Sartorius and NovaSep) tested. As can be seen from the results as shown in Table 2 a pressure difference over the membrane (dp) of at least 0.5 bar and a transmembrane pressure (TMP) of at least 0.75 bar are necessary to reach a FLUX rate of at least 100 l/h/m².

TABLE 2

FLUX rates resulting from different parameters selected for screening experiments

| p1 [bar] | p2 [bar] | p3 [bar] | dp [bar] | TMP [bar] | Sartorius, PES, 100 kDa FLUX [l/h/m²] | NovaSet, mPES, 100 kDa FLUX [l/h/m²] | Hydrosart, 100 kDa FLUX [l/h/m²] |
|---|---|---|---|---|---|---|---|
| 0.5 | 0 | 0 | 0.5 | 0.25 | 45 | 54.6 | 72 |
| 1 | 0.5 | 0 | 0.5 | 0.75 | 133.8 | 141.6 | 171 |
| 1.5 | 1 | 0 | 0.5 | 1.25 | 164.4 | 172.8 | 235.8 |
| 1 | 0 | 0 | 1 | 0.5 | 87.6 | 85.2 | 135.9 |
| 1.5 | 0.5 | 0 | 1 | 1 | 180 | 178.8 | 233.1 |
| 2 | 1 | 0 | 1 | 1.5 | 238.8 | 215.4 | 307.8 |
| 1.5 | 0 | 0 | 1.5 | 0.75 | 138.6 | 120 | 198.9 |
| 2 | 0.5 | 0 | 1.5 | 1.25 | 228.6 | 247.2 | 298.8 |
| 2.5 | 1 | 0 | 1.5 | 1.75 | 280.8 | 308.4 | 381.6 |
| 2 | 0 | 0 | 2 | 1 | 185.4 | 181.2 | 270 |
| 2.5 | 0.5 | 0 | 2 | 1.5 | 270 | 308.1 | 352.8 |

Based on these experiments the following parameters were chosen for TFF of the transcription reaction:

TABLE 3

Selected parameters for TFF of the transcription reaction

| Feed pressure (p1) | Retentate pressure (p2) | Permeate pressure (p3) | dp | TMP |
|---|---|---|---|---|
| 1.5 bar (=0.15 MPa) | 0.5 bar (=0.05 MPa) | 0 bar (=0 MPa) | 1 bar (=0.1 MPa) | 1 bar (=0.1 MPa) |

Figure 4:
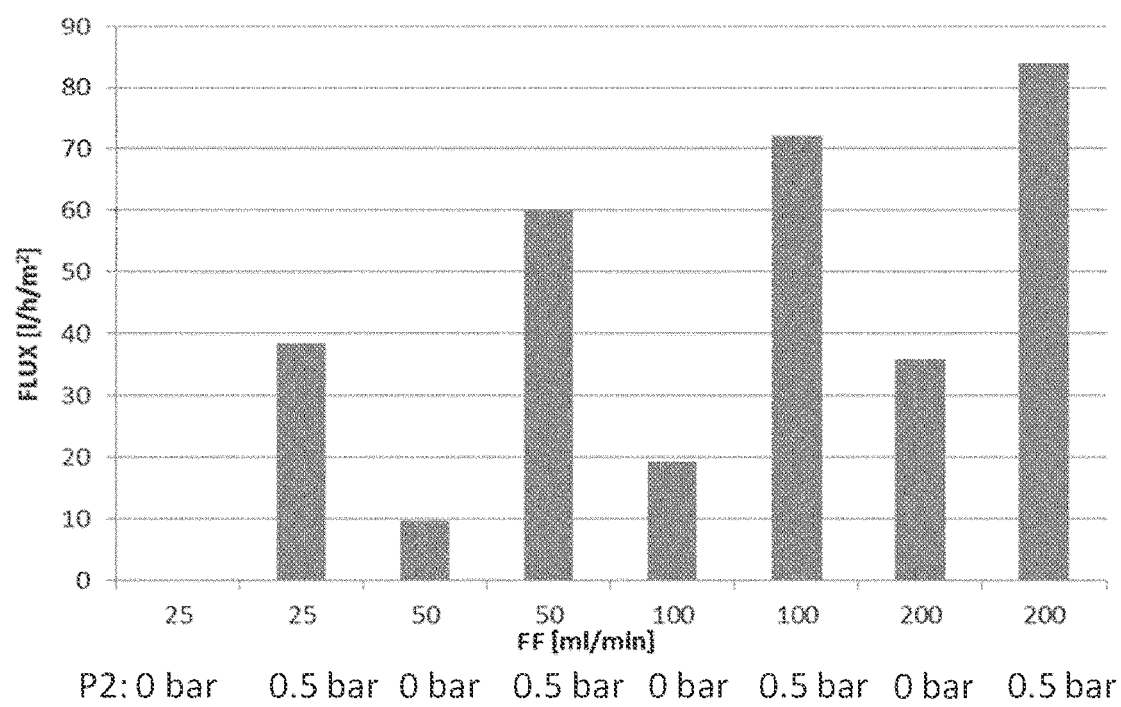
FIG. 4: Flow rate screening of hollow fibre module.

Example 9—TFF with Higher Membrane Load 9.1—TFF of Transcription Reaction Using a Hollow Fibre Module An RNA in vitro transcription reaction (R2587 with 3775 nt), diafiltrated in WFI was used to perform a flow rate screening in hollow fibre membrane (Hollow fibre module, 100 kDa, PES, 50 cm$^2$ from GE Healthcare). The membrane load was about 2.0 mg RNA/cm$^2$. As shown in FIG. 4, an increase in feed flow (FF) lead to an increase in permeate flux, also the addition of retentate pressure (0.05 MPa) showed an impact on permeate flux rate. The flux rates were between 5 and 85 l/h/m$^2$ (see FIG. 4).

9.2—TFF Using TFF Cassette Modules

An RNA in vitro transcription reaction (R2312 with 1885 nt), diafiltrated in WFI was used to perform a TFF using the following TFF parameters (Table 4):

TABLE 4

TFF parameters using TFF membrane cassette modules

| Feed pressure (p1) | Retentate pressure (p2) | Permeate pressure (p3) | dp | TMP |
|---|---|---|---|---|
| 0.15 MPa | 0.05 MPa | 0MPa | 0.1 MPa | 0.1 MPa |

The membrane load was about 4.5 mg RNA/cm$^2$. The Sartorius PES, 100 kDa, the NovaSet-LS ProStream (Low Binding mPES), 100 kDa from Novasep as well as the Hydrosart Sartorius 100 kDa (cellulose-based membrane) cassettes were used as TFF modules, respectively. The obtained permeate flux rates were higher than for the hollow fibre membranes with values between about 125-140 l/h/m$^2$ as shown in FIG. 5. Therefore, the diafiltration process is faster using TFF membrane cassettes due to the higher FLUX rates compared to the FLUX rates using hollow fibre membranes.

Example 10—RNA Stability During TFF

An mRNA containing sample (R2564; 2083 nt) was diafiltrated with WFI for several hours at room temperature using the Sartorius PES, 100 kDa membrane cassette and the TFF parameters as described above in Example 9.2. The RNA stability after transcription reaction was compared with the stability of RNA after subsequent TFF. The stability, i.e. the RNA integrity (relative area of full-length product) was determined by analytical RP-HPLC.

The results are summarized in FIG. 6.

The stability data showed that mRNA in transcription reaction mix was only stable if stored at −20° C. for up to 60 days (85-90%); at 5° C. integrity started decreasing slowly from the beginning (it sank from 85% to 61% in 61 days). A very rapid decrease in integrity was measured (decline from 81% to 51% over 14 days) if the mRNA was stored at room temperature. On the other hand, mRNA after TFF of the transcription reaction mix as described above was stable over 30 days if stored at −20° C. and at 5° C. If the mRNA was stored at room temperature it still showed high integrities for at least 7 days and then slowly decreased down to 80% integrity in 33 days. From this experiment it can be concluded, that a higher degree of RNA stability was achieved, by TFF of mRNA in WFI in comparison to the stability of RNA in the in vitro transcription reaction without purification by TFF.

Example 11—TFF of RNA Containing RP-HPLC Pool 11.1—TFF Parameters for Diafiltration of RP-HPLC Pool RP-HPLC purified RNA samples (as described in Example 5) in WFI, 0.1 M TEAA, 13% acetonitrile were used for the parameter screening.

We screened the different membranes (Hydrosart (cellulose-based membrane) from Sartorius, Omega Centramate T OS100T02, PES 100 kDa from PALL, and PES-based membranes with a MWCO of 100 kDa and 300 kDa from Sartorius) in respect to TMP vs. permeate flux and at different RNA concentrations (Table 5). The different membranes behaved similar during TMP screening experiments. In general, the higher the dp and TMP the higher the measured FLUX is (Table 5). At higher TMP values the process tends to be controlled by formation of the cake layer (maximum permeate flux reached, permeate flux independent of TMP).

TABLE 5

Results of the parameter screening

| RNA conc [µg/µl] | p1 [bar] | p2 [bar] | p3 [bar] | dp [bar] | TMP [bar] | Sartorius PES 100 kDa [l/h/m$^2$] | Hydrosart. 100 kDa [l/h/m$^2$] | Sartorius. PES 300 kDa [l/h/m$^2$] | PALL. Centramate. 100 kDa [l/h/m$^2$] |
|---|---|---|---|---|---|---|---|---|---|
| 0.1 | 0.5 | 0 | 0 | 0.5 | 0.25 | 43.2 | 73.8 | 49.2 | 94.8 |
| 0.1 | 1 | 0.5 | 0 | 0.5 | 0.75 | 104.4 | 160.2 | 120 | 182.4 |
| 0.1 | 1.5 | 1 | 0 | 0.5 | 1.25 | 118.8 | 171 | 129.6 | 204 |
| 0.1 | 1 | 0 | 0 | 1 | 0.5 | 46.8 | 126.9 | 123.6 | 127.8 |
| 0.1 | 1.5 | 0.5 | 0 | 1 | 1 | 106.8 | 200.7 | 182.4 | 207.6 |
| 0.1 | 2 | 1 | 0 | 1 | 1.5 | 130.2 | 211.5 | 194.4 | 258 |
| 0.1 | 1.5 | 0 | 0 | 1.5 | 0.75 | 68.4 | 178.2 | 144 | 154.8 |
| 0.1 | 2 | 0.5 | 0 | 1.5 | 1.25 | 118.8 | 225.9 | 204 | 242.4 |
| 0.1 | 2.5 | 1 | 0 | 1.5 | 1.75 | 151.2 | 248.4 | 219.6 | 304.8 |
| 0.1 | 2 | 0 | 0 | 2 | 1 | 86.4 | 205.2 | 169.2 | 199.2 |

TABLE 5-continued

Results of the parameter screening

| 0.1 | 2.5 | 0.5 | 0 | 2 | 1.5 | 129.6 | 260.1 | 224.4 | 282 |
| 0.1 | 3 | 1 | 0 | 2 | 2 | 165.6 | | 0 | 0 |

| RNA-conc [µg/µl] | p1 [bar] | p2 [bar] | p3 [bar] | dp [bar] | TMP [bar] | Sartorius PES 100 kDa [l/h/m²] | Hydrosart. 100 kDa [l/h/m²] | Sartorius. PES 300 kDa [l/h/m²] | PALL. Centramate. 100 kDa [l/h/m²] |
|---|---|---|---|---|---|---|---|---|---|
| 1 | 0.5 | 0 | 0 | 0.5 | 0.25 | 22.8 | 62.4 | 42 | 56.4 |
| 1 | 1 | 0.5 | 0 | 0.5 | 0.75 | 65.7 | 95.4 | 78 | 108 |
| 1 | 1.5 | 1 | 0 | 0.5 | 1.25 | 76.5 | 97.2 | 85.2 | 117.6 |
| 1 | 1 | 0 | 0 | 1 | 0.5 | 42.3 | 105.6 | 74.4 | 84 |
| 1 | 1.5 | 0.5 | 0 | 1 | 1 | 87.3 | 138 | 106.8 | 133.2 |
| 1 | 2 | 1 | 0 | 1 | 1.5 | 103.5 | 135.6 | 112.8 | 142.8 |
| 1 | 1.5 | 0 | 0 | 1.5 | 0.75 | 59.4 | 136.8 | 99.6 | 112.8 |
| 1 | 2 | 0.5 | 0 | 1.5 | 1.25 | 99.9 | 160.8 | 124.8 | 159.6 |
| 1 | 2.5 | 1 | 0 | 1.5 | 1.75 | 130.8 | 165.6 | 130.8 | 176.4 |
| 1 | 2 | 0 | 0 | 2 | 1 | 75.6 | 166.2 | 121.2 | 139.2 |
| 1 | 2.5 | 0.5 | 0 | 2 | 1.5 | 118.8 | 178.8 | 138 | 184.8 |
| 1 | 3 | 1 | 0 | 2 | 2 | | | | |
| 1.5 | 0.5 | 0 | 0 | 0.5 | 0.25 | 22.8 | 57.6 | 38.4 | 48.6 |
| 1.5 | 1 | 0.5 | 0 | 0.5 | 0.75 | 69.6 | 85.5 | 67.2 | 95.4 |
| 1.5 | 1.5 | 1 | 0 | 0.5 | 1.25 | 74.4 | 90 | 69.6 | 109.8 |
| 1.5 | 1 | 0 | 0 | 1 | 0.5 | 38.4 | 104.4 | 67.2 | 84.6 |
| 1.5 | 1.5 | 0.5 | 0 | 1 | 1 | 78 | 126 | 92.4 | 135 |
| 1.5 | 2 | 1 | 0 | 1 | 1.5 | 98.4 | 118.8 | 93.6 | 165 |
| 1.5 | 1.5 | 0 | 0 | 1.5 | 0.75 | 46.8 | 127.8 | 88.8 | 117 |
| 1.5 | 2 | 0.5 | 0 | 1.5 | 1.25 | 93.6 | 136.8 | 114 | 168 |
| 1.5 | 2.5 | 1 | 0 | 1.5 | 1.75 | 114 | | 126 | 189 |
| 1.5 | 2 | 0 | 0 | 2 | 1 | 73.2 | | 117 | 147 |
| 1.5 | 2.5 | 0.5 | 0 | 2 | 1.5 | 110.4 | | 133.2 | 180 |
| 1.5 | 3 | 1 | 0 | 2 | 2 | | | | |

Although higher dp and TMP values might lead to an increase in FLUX rates, the following parameters for large scale experiments were selected (Table 6):

TABLE 6 selected parameters for TFF of RP-HPLC pool

| Feed pressure (p1) | Retentate pressure (p2) | Permeate pressure (p3) | dp | TMP |
|---|---|---|---|---|
| 0.1-0.2 MPa | 0.05-0.1 MPa | 0MPa | 0.05-0.1 MPa | 0.075-0.15 MPa |

The ranges for TMP and dp as shown in Table 6 were selected because under these conditions the process is not completely cake layer driven. Although higher dp values (specifically higher p1 values) lead to further increase of the FLUX rate, application in large scale processes are impeded due to restrictions in pump force. Moreover, lower shear force (lower dp and TMP values) is preferred in respect to RNA stability.

11.2—Spermidine Depletion Via TFF

In first experiments, the concentrated RP-HPLC pool was diafiltrated with water (WFI). In this case a relatively high residual spermidine concentration in the final RNA solution was observed. To eliminate the spermidine an additional diafiltration step before final diafiltration into water was introduced. Different diafiltration solutions (Table 7) were screened. Approximately 5-10 mL of a RNA (R2564) containing solution after RP-HPLC purification was diafiltrated with 100-200 mL diafiltration solution, followed by diafiltration with 100-200 mL water. Here, single-use Vivaflow PES-based membrane cassettes (Sartorius) with a MWCO between 10-100 kDa were applied. Samples were analyzed after 10, 20, 30 and 40 diafiltration exchange volumes, respectively. Finally, the retentate was concentrated to approx. 0.5 g/L and the amount of spermidine was determined as described in Example 6.3. As a control, the RNA was not conditioned using TFF but precipitated by lithium chloride precipitation (see e.g. Sambrook et al., Molecular Cloning, a laboratory manual, 2nd edition, Cold Spring Harbor Laboratory Press 1989.) and the amount of contaminating spermidine was determined as described in Example 6.3.

The results are summarized in Table 7.

TABLE 7

Spermidine concentration after TFF using different diafiltration solutions

| Diafiltration buffer composition | Spermidine concentration (µg spermidine/ mg RNA) |
|---|---|
| water | 100.81 |
| 20 mM sodium phosphate pH 6.2 | 53.31 |
| 0.5 M sodium chloride | 0.01 |
| 0.2 M sodium chloride | 0.08 |
| Lithium chloride precipitation | 0.04 |

Diafiltration of the RP-HPLC pool using TFF with pure water or 20 mM sodium phosphate did not efficiently remove RNA-bound spermidine. Application of high salt diafiltration solutions, e.g. NaCl based solutions, resulted in substantially complete depletion of RNA-bound spermidine. Furthermore, salts (e.g. TEAA), organic solvents (TEA, ACN) were efficiently removed.

Subsequent optimization experiments have demonstrated that the NaCl concentration could be reduced to at least 0.2 M in order to increase permeate flow rates during diafiltration without effecting spermidine depletion efficiency.

Direct addition of NaCl to the concentrated RP-HPLC pool (final concentration~0.5 M or 0.2 M, respectively) resulted in faster spermidine depletion by TFF (less diafiltration solution is needed to reach the spermidine depletion). Application of higher concentrations of NaCl in the diafiltration solution are not advisable since this might lead to RNA precipitation and, consequently, blocking of the TFF membrane. The spermidine depletion step can be performed after RP-HPLC purification or directly after in vitro transcription.

11.3.—Test of Different Membranes for Spermidine Depletion Step:

Two membranes (Novasep mPES 100 kDa and the cellulose-based Sartorius Hydrosart 100 kDa) were further analyzed. We tested both membranes at higher sample load (approx. 2 mg RNA/cm$^2$ membrane) for diafiltration. For concentration and diafiltration the following parameters were chosen: dp=1 bar and TMP=1.5 bar, membrane load: 2.0 mg mRNA/cm$^2$ membrane. mRNA in WFI, 0.1 M TEAA, 13% acetonitrile and 0.2 M NaCl was concentrated from 0.1 g/l to 5 g/l and FLUX rates were determined. Diafiltration against 10 diafiltration volumes (dv) of 0.2 M NaCl solution and 10 dv of WFI was performed.

Results:

The overall time for concentration and diafiltration of 380 mg mRNA was very similar: NovaSet: 2.8 h, Hydrosart: 2.68 h. Respective FLUX rates for the diafiltration step are shown in FIG. 7.

Example 12—TFF of Linearization Reaction with Higher Membrane Load

For concentration and diafiltration of the linearization reaction we tested TFF membranes made from different material, with a MWCO of 100 kDa and membrane area of 200 cm$^2$ from different suppliers (The PES-based membranes Sartocon Slice 200 from Sartorius and the NovaSet-LS ProStream (Low Binding mPES) from NovaSep and the cellulose-based membrane Sartocon Slice 200, Hydrosart from Sartorius) with a high membrane load (5.6 and 6 g plasmid DNA/m$^2$). The parameters selected for TFF of the transcription reaction were applied in this step as well, as they showed good results before. Therefore dp and TMP=1 bar (P1=1.5 bar, P2=0.5 bar and P3=0 bar) were selected to concentrate pDNA (P1452.8 120 mg) from 0.2 g/l to approximately 1.5 g/l and afterwards for diafiltration against 10 diafiltration volumes WFI.

Results:

All tested membranes showed similar results. During concentration of the linearization reaction (FIG. 8A), FLUX rates decreased rapidly, but during diafiltration in WFI (FIG. 8B) the FLUX-rates increased again. Both PES-based membranes (Sartorius PES and NovaSet mPES) showed similar results, however, the Hydrosart membrane (Sartorius) showed higher permeate flow rates.

Example 13—Complete Process 13.1—Linearization of pDNA

Linearization of the plasmid DNA P1141 was conducted according to Example 2.

13.2—Concentration and Diafiltration of Linearized pDNA Using TFF

For tangential flow filtration of the linearization reaction, a Vivaflow50 filter cassette (PES membrane, MWCO 100 kDa, Sartorius) was used. Before assembling the diafiltration setup, all product contacting components (tubes, feed tank etc.) were thoroughly washed with ethanol and water. Next, the setup was washed with ultra-pure water. Then, the setup was chemically sanitized with 500 mM NaOH solution. Subsequently, the setup was washed with WFI until a pH of 7 was measured in the retentate. Then, the feed tank was filled with 150 ml linearization reaction according to Example 2.

In a first concentration step, approximately 100 ml of restriction reaction was filtered, to obtain 50 ml retentate with a higher pDNA concentration. Next, a vacuum was applied to the feed tank, and the feed tube was connected to a WFI bottle. Then, the diafiltration procedure with 10 volumes (500 ml in total) WFI was performed. Subsequently, the retentate was concentrated as much as possible. After concentration, the retentate was collected in a sterile 50 ml reaction tube. The retentate was analyzed on a DNA agarose gel (see FIG. 9). Retentate solutions were stored at −20° C. For agarose gel electrophoresis the DNA concentration was determined by measuring the absorption at 260 nm. The indicated amounts of DNA were used for gel electrophoresis.

Results

Photometrical Determination of the DNA Concentration after Concentration and Diafiltration:

The DNA concentration of the different DNA samples was determined by measuring the absorption at 260 nm:

TABLE 8

| Plasmid concentration | | |
|---|---|---|
| | Concentration [g/l] | Volume for agarose gel [µl] |
| Permeate from concentration step | n/a | 10 |
| Permeate from diafiltration step | n/a | 10 |
| Retentate from diafiltration step | 0.10 | 3 |
| Linearized plasmid | 0.17 | 1.8 |
| Plasmid control | 0.10 | 3 |

The dsDNA concentration in the retentate was photometrically determined to be 1.05 g/l in a final volume of 22 ml. The diafiltration of the linearized pDNA using TFF yielded 96.6% of input DNA.

Agarose Gel Electrophoresis:

Only a negligible amount of plasmid DNA is visible in the permeate of the concentration step and of the diafiltration step.

13.3—RNA In Vitro Transcription 800 ml of in vitro transcription mix as described in Example 4 was incubated for 3 h at 37° C. Next, CaCl$_2$ and DNase I was added and subsequently incubated for 2 h at 37° C.

13.4—Diafiltration of the Transcription Reaction

The TFF system Sartoflow 200 with two PES membranes (Sartorius, 200 cm$^2$, 100 kDa) was used to exchange the buffer of three aliquots (400 ml each) of the transcription reaction to WFI (process parameters indicated in Table 9). First, container and tubes were cleaned with ultrapure water, ethanol and WFI. Then the setup was assembled and the filter cassette was mounted on the Sartocon holder according to the manufacturer's instructions. The whole system was cleaned with ultra-pure water. Subsequently, the system was chemically sanitized by a 1 hour wash with 1 M NaOH. Then, the setup was washed with WFI until a pH of 7 was measured in the retentate and the system was equilibrated with 500 ml WFI. After that, 400 ml transcription reaction (see 13.3) were added to the retentate reservoir, pressures (dp and TMP) were set to 1 bar, and the diafiltration procedure was started against 10 diafiltration volumes (DFV) water for injection (WFI). After diafiltration by TFF the RNA concentration was measured photometrically.

TABLE 9

TFF parameters used for diafiltration of the transcription reaction

| Parameters | |
|---|---|
| Amount of RNA [mg] | 2100-2200 |
| Volume of RNA-solution [ml] | 410-430 |
| membrane | Sartorius, PES, 100 kDa |
| Number of membranes | 2 |
| pressures [bar] | P1 = 1.5 |
| | P2 = 0.5 |
| | P3 = 0 |
| | TMP und dp = 1 bar |
| Diafiltration volume WFI [l] | 4.1-4.3 |
| Membrane load [mg RNA/cm$^2$] | 5-5.6 |

Results:

The final concentration of the RNA after diafiltration was 5 g/l and the total recovery rate of the RNA after buffer exchange via diafiltration was 98%.

Example 13.5—RP-HPLC Purification of the Conditioned Transcription Reaction

The RNA solution obtained from Example 13.4 was diluted to 100 mM TEAA and a concentration of 1 g/l by addition of 1 M triethylammonium acetate (TEAA) and WFI. The RNA was step-wise purified according to Example 5. The HPLC fractions were collected, the product-containing fractions were pooled and divided in three pools I to III.

Moreover, fractions were analyzed for RNA content (UV260/280) and every fraction was analyzed for RNA integrity.

Results:

TABLE 10

Determination of RNA concentration and RNA integrity after RP-HPLC purification

| Pools | Volume | RNA conc. | RNA amount | integrity |
|---|---|---|---|---|
| Pool I | Ca. 7.2 L | 0.12 g/l | Ca. 840 mg | 97.8% |
| Pool II | Ca. 7.3 L | 0.12 g/l | Ca. 840 mg | 97.7% |
| Pool III | Ca. 6.2 L | 0.12 g/l | Ca. 744 mg | 95.7% |

Compared to the starting material (TFF conditioned RNA), the integrity could be increased by >10% (86.5% RNA integrity before RP-HPLC) by separating aborted RNA species.

Example 13.6—Concentration and Diafiltration of the RP-HPLC Pool Via TFF

The three RP-HPLC purified RNA pools were processed separately using an additional concentration and diafiltration step with TFF to further separate the RNA from impurities (e.g. spermidine contaminations) and to exchange the solvent.

First, every pool was concentrated from 0.12 g/l to approximately 5 g/l using TFF. 5M NaCl solution was added to the retentate to get a final concentration of 0.2 M NaCl. Then, a diafiltration was performed against 0.2 M NaCl (10 DFV) to remove spermidine impurities. Next, the diafiltration solution was exchanged to WFI (10 DFV). The process parameters are shown in Table 11. After TFF RNA concentration was determined by measuring the absorption at 260 nm. For agarose gel electrophoresis the indicated amounts of RNA were used for gel electrophoresis.

TABLE 11

Parameters used for TFF of the RP-HPLC pools

| | Pool 1 | Pool 2 | Pool 3 |
|---|---|---|---|
| Pressures used for concentration [bar] | P1 = 2<br>P2 = 0.5<br>P3 = 0<br>TMP = 1.2<br>dp = 1.5 | P1 = 2<br>P2 = 1<br>P3 = 0<br>TMP = 1.5<br>dp = 1.0 | P1 = 2<br>P2 = 1<br>P3 = 0<br>TMP = 1.5<br>dp = 1.0 |
| Pressures used for diafiltration [bar] | P1 = 2<br>P2 = 1<br>P3 = 0<br>TMP = 1.5<br>dp = 1.0 | P1 = 2<br>P2 = 1<br>P3 = 0<br>TMP = 1.5<br>dp = 1.0 | P1 = 2<br>P2 = 1<br>P3 = 0<br>TMP = 1.5<br>dp = 1.0 |
| TFF membrane | Hydrosart-Membrane 200 cm$^2$; 100 kDa | Hydro s art-Membrane 200 cm$^2$; 100 kDa | Hydrosart-Membrane 200 cm$^2$; 100 kDa |
| Membrane load | 2.1 mg RNA/cm$^2$ | 2.1 mg RNA/cm$^2$ | 1.9 mg RNA/cm$^2$ |
| start volume | 7.2 L | 7.3 L | 6.2 L |

Results:

The yield after the diafiltration was spectrometric ally determined to be 94.44%, 94.3% and 90.5% respectively.

Agarose Gel Electrophoresis:

Samples of the TFF diafiltration procedure after RP-HPLC purification were analyzed. Respective samples were analyzed using agarose gel electrophoresis (see FIG. 10). Loading scheme of the respective RNA agarose gel is shown in table 12.

TABLE 12

Loading scheme of permeate and retentate samples taken during TFF of the RP-HPLC pools.

| Lane | Sample | RNA conc. [µg/ul] | Volume used for agarose gel electrophoresis [µl] |
|---|---|---|---|
| 1 | RNA marker | | 8 |
| 2 | RP-HPLC Pool I | 0.12 | 9 |
| 3 | RP-HPLC Pool II | 0.12 | 9 |
| 4 | RP-HPLC Pool III | 0.12 | 9 |

TABLE 12-continued

Loading scheme of permeate and retentate samples taken during TFF of the RP-HPLC pools.

| Lane | Sample | RNA conc. [µg/ul] | Volume used for agarose gel electrophoresis [µl] |
|---|---|---|---|
| 5 | TFF permeate | n.a. | 9 |
| 6 | TFF permeate (40× concentrated) | n.a. | 9 |
| 7 | TFF retentate Pool I | 5.00 | 1 |
| 8 | TFF retentate Pool II | 5.00 | 1 |
| 9 | TFF retentate Pool III | 4.84 | 1 |
| 10 | Final product | 4.84 | 1 |
| 11 | Control | 5.00 | 1 |
| 12 | Control | 1.00 | 1 |
| 13 | empty | | |
| 14 | RNA marker | | 8 |

Results:

The TFF permeate samples did not contain detectable RNA levels (even though samples that had been concentrated 40×).

The TFF retentate samples and the final TFF conditioned RNA pool contained RNA of integrity of about 100%, all of those with a band size of 2476 bases, which was in accordance to the theoretically expected size.

Example 13.7—Determination of Protein Content Using a BCA Assay

To determine the protein content in the samples, the BCA-test was used. The total protein concentration contained in a sample was measured photometrically via absorption at 562 nm compared to a protein standard (bovine serum albumin, BSA). The test was performed using a commercially available BCA kit, according to the manufacturer's instructions.

To produce a 20 µg/ml bovine serum albumin (BSA) solution stock solution, 20 µl BSA solution [1 mg/ml] was mixed with 980 µl water for injection. This BSA stock solution was used to generate a standard curve using BSA solutions of different concentrations (50 µl each, diluted in WFI): 2.5 µg/ml; 5 µg/ml; 10 µg/ml; 15 µg/ml; 20 µg/ml The protein content was determined in samples from the TFF after linearization reaction (Example 13.2), from the transcription reaction (Example 13.3), before RP-HPLC (Example 13.4) and after RP-HPLC and TFF against 0.2 M NaCl (Examples 13.5 and 13.6).

Results:

The measurements were performed in a standard photometer. Results are displayed in Table 13.

TABLE 13

Determined protein concentrations

| Sample | A562 nm (AU) average | Dilution | protein [µg/ml] | RNA/DNA conc. [mg/ml] | protein/RNA [µg/mg] |
|---|---|---|---|---|---|
| 1 TFF retentate after linearization | 0.717 | 20 | 324.2 | 1.05 | 308.8 |
| 2 transcription reaction | 0.404 | 1000 | 6823.4 | 5.07 | 1345.8 |
| 3 TFF retentate before RP-HPLC | 0.596 | 10 | 122.9 | 4.30 | 28.6 |

TABLE 13-continued

Determined protein concentrations

| Sample | A562 nm (AU) average | Dilution | protein [µg/ml] | RNA/DNA conc. [mg/ml] | protein/RNA [µg/mg] |
|---|---|---|---|---|---|
| 4 TFF retentate before RP-HPLC | 0.632 | 10 | 136 | 5,.2 | 26.7 |
| 5 TFF retentate before RP-HPLC | 0.625 | 10 | 131.2 | 5.22 | 25.1 |
| 6 TFF retentate after RP-HPLC Pool I | 0.397 | 2 | 13.2 | 5.03 | 2.6 |
| 7 TFF retentate after RP-HPLC Pool II | 0.352 | 2 | 10.7 | 5.00 | 2.1 |
| 8 TFF retentate after RP-HPLC Pool III | 0.455 | 2 | 16.6 | 4.84 | 3.4 |

Values of the BCA-assay are shown. 1: TFF retentate of linearization reaction; 2: Transcription reaction; 3-5: TFF retentates of transcription reactions before RP-HPLC; 6-8: TFF retentates of transcription reactions after RP-HPLC A step-wise depletion of the protein content per RNA over the whole RNA purification procedure could be observed.

Figure 11:
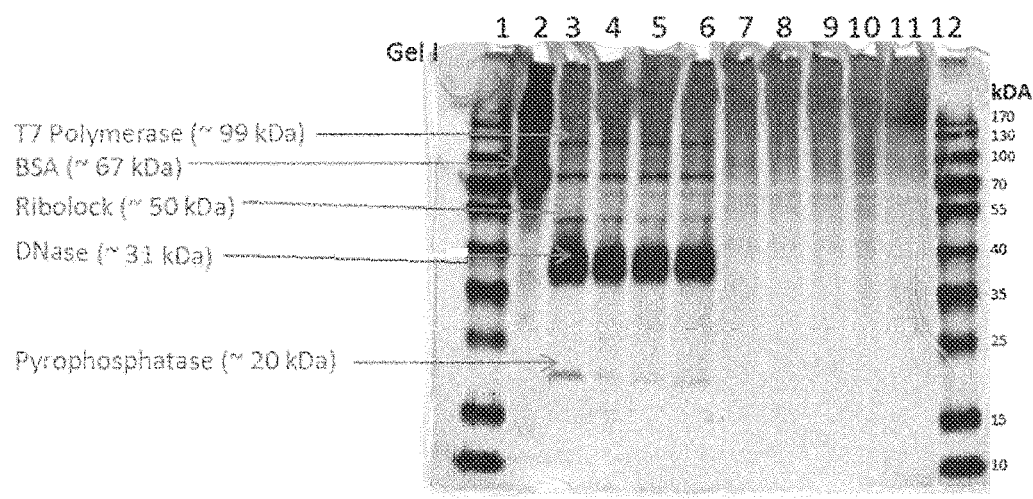
Figure 12:
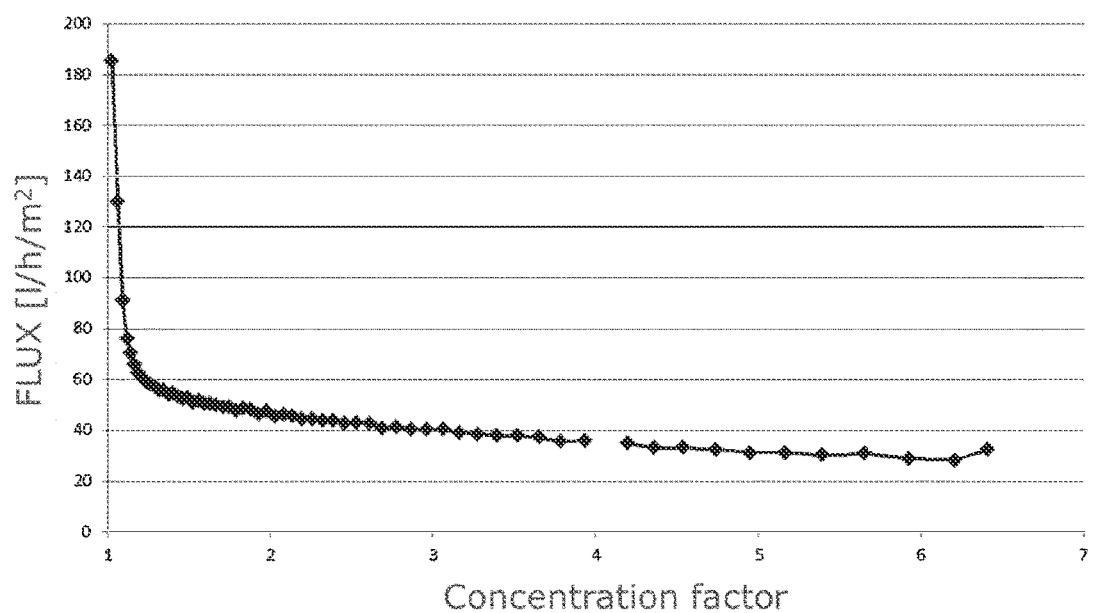

SDS-PAGE:

SDS-PAGE was used to determine the protein content in the different samples. The indicated amounts of samples were used for SDS-PAGE. The results are shown in FIG. 11.

TABLE 14

Samples used for SDS PAGE

| Lane | Sample | RNA/DNA conc. [mg/ml] | Volume [µl] |
|---|---|---|---|
| 1 | Protein Marker | | |
| 2 | TFF retentate after linearization | 1.05 | 9.5 |
| 3 | transcription reaction | 5.07 | 2.0 |
| 4 | TFF retentate before RP-HPLC | 4.30 | 2.3 |
| 5 | TFF retentate before RP-HPLC | 5,.2 | 2.0 |
| 6 | TFF retentate before RP-HPLC | 5.22 | 1.9 |
| 7 | TFF retentate after RP-HPLC Pool I | 5.03 | 2.0 |
| 8 | TFF retentate after RP-HPLC Pool II | 5.00 | 2.0 |
| 9 | TFF retentate after RP-HPLC Pool III | 4.84 | 2.1 |
| 10 | Final Product | 4.84 | 2.1 |
| 11 | control | 5.00 | 2.0 |
| 12 | Protein Marker | | |

No protein bands were detectable in samples after RP-HPLC purification.

Example 13.8—Determination of Spermidine Concentration

Spermidine concentration was measured in the TFF retentates before RP-HPLC (Example 13.4) and after RP-HPLC purification and TFF against 0.2 M NaCl (Example 13.5 and 13.6) according to Example 6.3.

Results:

TABLE 15

Spermidine concentrations in RNA samples

| Sample | RNA conc. [g/l] | Spermidin/RNA [ng/mg] |
|---|---|---|
| TFF retentate before RP-HPLC (1:20) | 0.22 | 39964.50 |
| TFF retentate before RP-HPLC (1:20) | 0.26 | 39039.21 |
| TFF retentate before RP-HPLC (1:20) | 0.26 | 37748.26 |
| RP-HPLC-Pool I | 0.12 | 1834.98 |
| RP-HPLC-Pool II | 0.12 | 30.08 |
| RP-HPLC-Pool III | 0.12 | 110.90 |
| TFF retentate after RP-Pool I | 5.03 | 1.00 |
| TFF retentate after RP-Pool II | 5.00 | 3.08 |
| TFF retentate after RP-Pool III | 4.84 | 1.48 |

Results:

Spermidine was detectable in samples of the TFF retentates before RP-HPLC purification. In the samples purified by RP-HPLC and TFF using 0.2 M NaCl only a very low amount of spermidine was detectable (see Table 15).

Example 13.9—Determination of Organic Solvents

The concentration of acetonitrile (ACN) and TEAA was determined according to Example 6.4.

Results:

The final sample after RP-HPLC purification and TFF contained less than 40 ppm ACN and less than 2 ppm TEAA.

Example 14—Overview of the Process and Key Process Parameters

In the following, a further example of the inventive method is illustrated, providing process parameters of the method for each of the individual steps including concentration of the linearization reaction and diafiltration of linearized plasmid DNA, diafiltration of RNA in vitro transcription reaction and concentration and diafiltration of an RP-HPLC RNA pool.

14.1—Concentration of the Linearization Reaction and Diafiltration of Linearized Plasmid DNA Using TFF:

Linearization of the plasmid DNA was performed as described in Example 2. For tangential flow filtration of the linearization reaction (conducted according to Example 2), a Hydrosart filter cassette (cellulose based membrane, MWCO 100 kDa, Sartorius) was used. The plasmid DNA concentration procedure as well as the diafiltration procedure was performed as explained above (see Example 13). The result of the concentration of the linearization mix is provided in FIG. 12. The result of the diafiltration of the linearized plasmid DNA is provided in FIG. 13. Relevant process parameters are summarized in Table 16.

TABLE 16

TFF process parameters of plasmid DNA concentration and diafiltration

| | Process parameter | |
|---|---|---|
| Concentration of the linearization reaction | Initial pDNA concentration [g/l] | 0.2 |
| | Pressures used for concentration of the pDNA linearization mix [bar] | P1 = 1.5<br>P2 = 0.5<br>P3 = 0<br>TMP = 1<br>dp = 1 |
| | Obtained pDNA concentration [g/l] | 1.0 or 1.5 |
| Diafiltration of the linearized pDNA in WFI | Pressures used for diafiltration of linearized pDNA [bar] | P1 = 1.5<br>P2 = 0.5<br>P3 = 0<br>TMP = 1<br>dp = 1 |
| | DFV | 10 |
| | DF buffer | WFI |
| General parameters | TFF membrane cassettes | Hydrosart membrane cassette; 200 cm$^2$; 100 kDa or NovaSet-LS ProStream (Low Binding mPES), 100 kDa |
| | Membrane load | 0.1-0.6 mg DNA/cm$^2$ |
| | Feed flowrate [l/h/m$^2$] | 750-900 |
| | Permeate flux rate [l/h/m$^2$] | 30-100 |

14.2—Diafiltration of the RNA IVT Reaction by TFF:

RNA in vitro transcription was performed as described in Example 4. For tangential flow filtration of the RNA IVT reaction (conducted according to Example 4), a Hydrosart filter cassette (cellulose based membrane, MWCO 100 kDa, Sartorius) was used. The conditioning of the RNA IVT reaction was performed as explained above (see Example 13). The result of the diafiltration of the RNA IVT reaction is provided in FIG. 14. Relevant process parameters are summarized in Table 17.

TABLE 17

TFF Process parameters of the RNA IVT reaction diafiltration

| Process parameter | |
|---|---|
| Pressures used for diafiltration of RNA IVT reaction [bar] | P1 = 1.5<br>P2 = 0.5<br>P3 = 0<br>TMP = 1-1.5<br>dp = 1 |
| DFV | 10 |
| DF buffer | WFI |
| TFF membrane cassettes | Hydrosart membrane cassette; 200 cm$^2$; 100 kDa<br>or<br>NovaSet-LS ProStream (Low Binding mPES), 100 kDa |

TABLE 17-continued

TFF Process parameters of the RNA IVT reaction diafiltration

| Process parameter | |
|---|---|
| Membrane load | 2.5-6.5 mg RNA/cm$^2$ |
| Feed flowrate [l/h/m$^2$] | 300-1050 |
| Permeate flux rate [l/h/m$^2$] | 20-120 |

14.3—Concentration and Diafiltration of the RP-HPLC RNA Pool

The in vitro transcribed RNA was purified by RP-HPLC as described in Example 5. For tangential flow filtration of the RP-HPLC RNA pool, a Hydrosart filter cassette (cellulose based membrane, MWCO 100 kDa, Sartorius) was used. The concentration of the RP-HPLC RNA pool was performed as explained above (see Example 13). The result of the concentration of the RP-HPLC RNA is provided in FIG. 15. The diafiltration of the RNA into 0.2 M NaCl and a further diafiltration of the RNA into WFI was performed as explained above (see Example 13). The result of the diafiltration of the RP-HPLC RNA pool is provided in FIG. 16. Relevant process parameters are summarized in Table 18.

TABLE 18

TFF process parameters of the RP-HPLC RNA concentration and diafiltration

| | Process parameter | |
|---|---|---|
| Concentration of the RP-HPLC RNA pool | Initial RNA concentration [g/l] | 0.1 |
| | Pressures used for concentration of the pDNA linearization mix [bar] | P1 = 1.5<br>P2 = 0.5<br>P3 = 0<br>TMP = 1<br>dp = 1 |
| | Obtained RNA concentration [g/l] | 5 +/− 0.25 |
| Diafiltration of the RP-HPLC RNA pool in NaCl buffer | Pressures used for diafiltration of RNA [bar] | P1 = 1.5<br>P2 = 0.5<br>P3 = 0<br>TMP = 1 - 1.5<br>dp = 1 |
| | DFV | 10 |
| | DF buffer | 0.2 M NaCL |
| Diafiltration of the RP-HPLC RNA pool in WFI | Pressures used for diafiltration of RNA [bar] | P1 = 1.5<br>P2 = 0.5<br>P3 = 0<br>TMP = 1 - 1.5<br>dp = 1 |
| | DFV | 10 |
| | DF buffer | WFI |
| General parameters | TFF membrane cassettes | Hydrosart membrane cassette; 200 cm$^2$; 100 kDa<br>or<br>NovaSet-LS ProStream (Low Binding mPES), 100 kDa |
| | Membrane load | 2 mg-2.5 mg RNA/cm$^2$ |
| | Feed flowrate [l/h/m$^2$] | 900-1500 |
| | Permeate flux rate [l/h/m$^2$] | 25-140 |
| | Temperature [° C.] | 17° C. or <17° C. |

Embodiment List

1. A method for producing and purifying RNA, comprising the steps of
    A) providing DNA encoding the RNA;
    B) transcription of the DNA to yield a solution comprising transcribed RNA; and
    C) conditioning and/or purifying of the solution comprising transcribed RNA by one or more steps of tangential flow filtration (TFF).
2. The method according to item 1, wherein in step A) plasmid DNA is provided as DNA encoding the RNA and the method comprises subsequently to step A) the steps:
    A1) linearization of the plasmid DNA in a linearization reaction;
    A2) optionally termination of the linearization reaction; and
    A3) conditioning and/or purifying of the linearization reaction comprising linearized plasmid DNA by one or more steps of TFF.
3. The method according to item 1 or 2, wherein step C) comprises at least one diafiltration step and/or at least one concentration step using TFF.
4. The method according to item 3, wherein the at least one diafiltration step using TFF in step C) comprises diafiltration with an aqueous salt solution.
5. The method according to item 4, wherein the aqueous salt solution is a NaCl solution, preferably an aqueous solution comprising from about 0.1 M NaCl to about 1 M NaCl, more preferably a solution comprising from about 0.2 to about 0.5 M NaCl.
6. The method according to item 3, wherein the at least one diafiltration step using TFF of step C) comprises diafiltration with water.
7. The method according to any one of items 1 to 6, wherein the method does not comprise a step of phenol/chloroform extraction and/or DNA and/or RNA precipitation.
8. The method according to any one of items 1 to 7, wherein the method does not comprise a step of using a TFF hollow fiber membrane.
9. The method according to any one of items 1 to 8, wherein the at least one or more steps of TFF comprises using a TFF membrane with a molecular weight cutoff of ≤500 kDa, preferably of ≤200 kDa and most preferably of ≤100 kDa.
10. The method according to any one of items 1 to 9, wherein the at least one or more steps of TFF comprises using a TFF membrane comprising at least one of polyethersulfone (PES), modified polyethersulfone (mPES), a cellulose derivative membrane or combinations thereof.
11. The method according to any one of items 1 to 10, wherein the at least one or more steps of TFF comprises using a TFF membrane comprising a cellulose derivative membrane with a molecular weight cutoff of about 100 kDa.
12. The method according to any one of items 1 to 11, wherein the at least one or more steps of TFF comprises using a TFF membrane cassette.
13. The method according to any one of items 1 to 12, wherein the method comprises in step C) at least one further purification method before or after the one or more steps of TFF.
14. The method according to any of items 1 to 13, wherein the method comprises in step C) the steps:
    C1) optionally termination of transcription;
    C2) conditioning and/or purifying of the solution comprising the transcribed RNA by one or more steps of TFF;
    C3) purifying the RNA by any further purification method; and
    C4) conditioning and/or optionally purifying of the solution comprising the transcribed RNA obtained after step C3) by one or more steps of TFF.
15. The method according to item 14, wherein step C2) comprises at least one step of diafiltration using TFF with water and/or diafiltration with an aqueous salt solution, preferably an aqueous NaCl solution and more preferably with an aqueous solution comprising from about 0.1 M NaCl to about 1 M NaCl, more preferably a solution comprising from about 0.2 to about 0.5 M NaCl.
16. The method according to item 14 or 15, wherein step C4) comprises at least one first diafiltration step using TFF.
17. The method according to item 16, wherein step C4) comprises at least one second diafiltration step using TFF.
18. The method according to any one of items 16 or 17, wherein the at least one first diafiltration step using TFF in step C4) comprises diafiltration with an aqueous salt solution, preferably an aqueous NaCl solution and more preferably with an aqueous solution comprising from about 0.1 M NaCl to about 1 M NaCl, more preferably a solution comprising from about 0.2 to about 0.5 M NaCl.
19. The method according to item 17 or 18, wherein the second diafiltration step using TFF of step C4) comprises diafiltration with water.
20. The method according to any one of items 13 to 19, wherein the at least one further purification method is performed by means of high performance liquid chromatography (HPLC) or low normal pressure liquid chromatography methods.
21. The method according to any one of items 13 to 20, wherein the at least one further purification method is a reversed phase chromatography method.
22. The method according to any one of items 1 to 21, wherein all steps of TFF are performed with the same TFF membrane.
23. The method according to any one of items 1 to 22, wherein the transcribed RNA is selected from the group consisting of mRNA, viral RNA, retroviral RNA and replicon RNA, small interfering RNA (siRNA), antisense RNA, CRISPR RNA, ribozymes, aptamers, riboswitches, immunostimulating RNA, transfer RNA (tRNA), ribosomal RNA (rRNA), small nuclear RNA (snRNA), small nucleolar RNA (snoRNA), microRNA (miRNA), and Piwi-interacting RNA (piRNA) or whole-cell RNA and preferably is mRNA.
24. The method according to any one of items 1 to 23, wherein the transcription of DNA in step B) is performed as in vitro transcription.

The invention claimed is:

1. A method for producing purified RNA, comprising the steps of:
    A1) providing a plasmid DNA encoding a RNA, wherein said RNA is 500 to 10000 nucleotides in length;
    A2) linearizing the plasmid DNA to produce linearized DNA;
    A3) ultrafiltering the linearized DNA by tangential flow filtration (TFF), to produce purified linearized DNA;
    B1) transcribing the purified linearized DNA to produce transcribed RNA;
    B2) treating the transcribed RNA with a DNase; and
    C1) ultrafiltering the transcribed RNA by performing at least one step of TFF using a TFF membrane cassette having a molecular weight cutoff (MWCO) of less than or equal to 500 kDa, to produce the purified RNA.
2. The method of claim 1, wherein the TFF membrane cassette has a MWCO of about 100 kDa to 300 kDa.

3. The method of claim 1, wherein the TFF membrane cassette has a MWCO of about 300 kDa.

4. The method of claim 1, wherein the TFF membrane cassette has a membrane comprising cellulose or a cellulose derivative.

5. The method of claim 1, wherein the method comprises at least one step of DNA or RNA purification using anion exchange chromatography.

6. A method for producing purified RNA, comprising the steps of:
- A1) providing a plasmid DNA encoding a RNA, wherein said RNA is 500 to 10000 nucleotides in length;
- A2) linearizing the plasmid DNA to produce linearized DNA;
- A3) ultrafiltering the linearized DNA by tangential flow filtration (TFF) to produce a purified linearized DNA;
- B1) transcribing the purified linearized DNA in the presence of a cap analog to produce a transcribed capped RNA;
- B2) treating the transcribed capped RNA with a DNase;
- C1) ultrafiltering the transcribed capped RNA by at least one step of TFF with an aqueous salt solution using a TFF membrane cassette having a molecular weight cutoff (MWCO) of less than or equal to 500 kDa; and
- C2) performing at least one further filtration using TFF, to obtain the purified RNA.

7. The method of claim 6, wherein providing the plasmid DNA comprises purifying the plasmid DNA.

8. The method of claim 6, wherein the TFF membrane cassette of step C1) has a MWCO of about 100 kDa to 300 kDa.

9. The method of claim 6, wherein the TFF membrane cassette of step C1) has a MWCO of about 300 kDa.

10. The method of claim 6, wherein the TFF membrane cassette comprises cellulose or a cellulose derivative.

11. The method of claim 7, wherein the method comprises at least one step of DNA or RNA purification using anion exchange chromatography.

12. The method of claim 6, wherein transcribing the purified linearized DNA is performed in the presence of a modified nucleotide to produce transcribed capped RNA having the modified nucleotide and wherein the modified nucleotide is 1-methyl-pseudouridine.

13. The method of claim 7, wherein the method further comprises formulating the purified RNA.

14. The method of claim 13, further comprising a filling step.

15. The method of claim 6, wherein transcribing the purified linearized DNA is performed in the presence of spermidine.

16. The method of claim 15, wherein transcribing the purified linearized DNA is performed in the presence of 0.1 mM to 10 mM spermidine.

17. The method of claim 16, wherein step C1) produces RNA with a reduced level of spermidine relative to the level of spermidine in the transcribing step.

18. The method of claim 17, comprising treating the transcribed capped RNA with DNaseI in the presence of $CaCl_2$, following by addition of EDTA.

19. The method of claim 6, wherein the TFF of step C2) is with a TFF membrane cassette.

20. The method of claim 19, wherein the membrane cassette of step C2) has a MWCO of about 100 kDa to 300 kDa.

21. The method of claim 19, wherein the membrane cassette of step C2) has a MWCO of about 300 kDa.

22. The method of claim 7, wherein the method comprises at least one step of DNA or RNA purification using anion exchange chromatography.

23. The method of claim 6, wherein the method comprises at least one further step of RNA purification or RNA concentration using TFF.

24. The method of claim 6, wherein the method does not include a step for organic solvent extraction or alcohol precipitation of the transcribed capped RNA.

25. The method of claim 6, wherein the method does not include a step for organic solvent extraction or alcohol precipitation of the plasmid DNA or the linearized DNA.

26. The method of claim 25, wherein the transcribed capped RNA comprises a Cap1 5' cap and a Poly(A) sequence of 50 to 250 nucleotides.

27. The method of claim 26, wherein the transcribed capped RNA comprises a modified nucleotide, which is 1-methyl-pseudouridine.

28. The method of claim 27, wherein linearizing the plasmid DNA is with a type II restriction endonuclease.

29. A method for producing a formulated purified mRNA, comprising the steps of:
- A1) providing a plasmid DNA encoding a mRNA, wherein said mRNA is 500 to 5000 nucleotides in length and comprises a Poly(A) sequence of 50 to 250 nucleotides;
- A2) linearizing the plasmid DNA to produce linearized DNA;
- A3) ultrafiltering the linearized DNA by tangential flow filtration (TFF) to produce a purified linearized DNA;
- B1) transcribing the purified linearized DNA in the presence of a cap analog, nucleoside triphosphates (NTPs), T7 polymerase, spermidine, salts and a buffer to produce a transcribed capped mRNA;
- B2) treating the transcribed capped mRNA with a DNase followed by addition of EDTA;
- C1) ultrafiltering the transcribed capped mRNA by at least one step of TFF with an aqueous salt solution using a TFF membrane cassette having a molecular weight cutoff (MWCO) of less than or equal to 500 kDa, thereby reducing the level of spermidine associated with the transcribed capped mRNA;
- C2) performing at least one further filtration using TFF, to obtain the purified mRNA; and
- D) formulating the purified mRNA by complexing the purified mRNA with a cationic compound, to obtain a formulated purified mRNA.

30. The method of claim 29, wherein the TFF membrane cassette has a MWCO of about 300 kDa and comprises a stabilized cellulose-based TFF membrane.

* * * * *